US008357669B2

(12) United States Patent
Ferrell et al.

(10) Patent No.: US 8,357,669 B2
(45) Date of Patent: Jan. 22, 2013

(54) METHOD OF TREATMENT FOR LYMPHEDEMA COMPRISING ADMINISTERING A POLYNUCLEOTIDE ENCODING VEGF-D

(75) Inventors: Robert E. Ferrell, Pittsburgh, PA (US); Kari Alitalo, Helsinki (FI); David N. Finegold, Pittsburgh, PA (US); Marika Karkkainen, Espoo (FI)

(73) Assignees: Vegenics Pty Limited, Toorak, Victoria (AU); University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/242,082

(22) Filed: Sep. 23, 2011

(65) Prior Publication Data

US 2012/0010276 A1    Jan. 12, 2012

Related U.S. Application Data

(60) Division of application No. 12/941,034, filed on Nov. 6, 2010, now abandoned, which is a continuation of application No. 12/366,359, filed on Feb. 5, 2009, now Pat. No. 7,829,536, which is a continuation of application No. 11/617,045, filed on (Continued)

(51) Int. Cl.
*A61K 48/00* (2006.01)
(52) U.S. Cl. .................................. 514/44 R
(58) Field of Classification Search ............ None
See application file for complete search history.

(56) References Cited

U.S. PATENT DOCUMENTS

| | | | |
|---|---|---|---|
| 5,002,867 A | 3/1991 | Macevicz |
| 5,143,854 A | 9/1992 | Pirrung et al. |
| 5,202,231 A | 4/1993 | Drmanac et al. |
| 5,521,065 A | 5/1996 | Whiteley et al. |
| 5,631,237 A | 5/1997 | Dzau et al. |
| 5,776,755 A | 7/1998 | Alitalo et al. |
| 5,792,453 A | 8/1998 | Hammond et al. |
| 5,837,832 A | 11/1998 | Chee et al. |
| 5,932,540 A | 8/1999 | Hu et al. |
| 5,935,820 A | 8/1999 | Hu et al. |
| 6,040,157 A | 3/2000 | Hu et al. |
| 6,107,046 A | 8/2000 | Alitalo et al. |
| 6,130,071 A | 10/2000 | Alitalo et al. |
| 6,171,799 B1 | 1/2001 | Skibbens et al. |
| 6,221,839 B1 | 4/2001 | Alitalo et al. |
| 6,235,713 B1 | 5/2001 | Achen et al. |
| 6,245,530 B1 | 6/2001 | Alitalo et al. |
| 6,331,302 B1 | 12/2001 | Bennett et al. |

(Continued)

FOREIGN PATENT DOCUMENTS

| | | |
|---|---|---|
| WO | WO-96/39515 | 12/1996 |
| WO | WO-97/05250 | 2/1997 |

(Continued)

OTHER PUBLICATIONS

Achen et al., Vascular endothelial growth factor D (VEGF-D) is a ligand for the tyrosine kinases VEGF receptor 2 (Flk1) and VEGF receptor 3 (Flt4), *Proc. Natl. Acad. Sci. USA*, 95: 548-53 (1998).

(Continued)

*Primary Examiner* — Robert Landsman
(74) *Attorney, Agent, or Firm* — Marshall, Gerstein & Borun LLP

(57) ABSTRACT

The present invention provides materials and methods for screening for and treating hereditary lymphedema in human subjects.

20 Claims, 9 Drawing Sheets

Related U.S. Application Data

Dec. 28, 2006, now abandoned, which is a division of application No. 10/661,740, filed on Sep. 12, 2003, now abandoned, which is a division of application No. 09/375,248, filed on Aug. 16, 1999, now Pat. No. 6,764,820, which is a continuation-in-part of application No. PCT/US99/06133, filed on Mar. 26, 1999.

(56) References Cited

U.S. PATENT DOCUMENTS

| | | |
|---|---|---|
| 6,361,946 B1 | 3/2002 | Alitalo et al. |
| 6,383,484 B1 | 5/2002 | Achen et al. |
| 6,403,088 B1 | 6/2002 | Alitalo et al. |
| 6,451,764 B1 | 9/2002 | Lee et al. |
| 6,576,608 B1 | 6/2003 | Lee et al. |
| 6,608,182 B1 | 8/2003 | Rosen et al. |
| 6,645,933 B1 | 11/2003 | Alitalo et al. |
| 6,673,343 B2 | 1/2004 | Bennett et al. |
| 6,689,580 B1 | 2/2004 | Achen et al. |
| 6,730,489 B1 | 5/2004 | Achen et al. |
| 6,730,658 B1 | 5/2004 | Alitalo et al. |
| 6,818,220 B1 | 11/2004 | Alitalo et al. |
| 6,824,777 B1 | 11/2004 | Alitalo et al. |
| 6,958,147 B1 | 10/2005 | Achen et al. |
| 7,097,986 B2 | 8/2006 | Achen et al. |
| 7,122,654 B2 | 10/2006 | Achen et al. |
| 7,125,714 B2 | 10/2006 | Alitalo et al. |
| 7,410,639 B2 | 8/2008 | Alitalo et al. |
| 7,423,125 B2 | 9/2008 | Alitalo et al. |
| 2002/0120123 A1 | 8/2002 | Rosen et al. |
| 2002/0146420 A1 | 10/2002 | Bennett et al. |
| 2002/0151489 A1 | 10/2002 | Gravereaux et al. |
| 2002/0182683 A1 | 12/2002 | Hu et al. |
| 2003/0008357 A1 | 1/2003 | Hu et al. |
| 2003/0028007 A1 | 2/2003 | Hu et al. |
| 2003/0166873 A1 | 9/2003 | Lee et al. |
| 2003/0211988 A1 | 11/2003 | Epstein |
| 2003/0232437 A1 | 12/2003 | Zhang et al. |
| 2004/0147448 A1 | 7/2004 | Alitalo et al. |
| 2004/0175730 A1 | 9/2004 | Achen et al. |
| 2004/0208879 A1 | 10/2004 | Alitalo et al. |
| 2005/0256075 A1 | 11/2005 | Alitalo et al. |
| 2006/0177428 A1 | 8/2006 | Achen et al. |
| 2006/0177901 A1 | 8/2006 | Alitalo et al. |
| 2007/0298493 A1 | 12/2007 | Achen et al. |
| 2008/0058258 A1 | 3/2008 | Achen et al. |
| 2008/0070831 A1 | 3/2008 | Achen et al. |
| 2008/0145366 A1 | 6/2008 | Achen et al. |
| 2008/0241152 A1 | 10/2008 | Alitalo et al. |
| 2008/0241153 A1 | 10/2008 | Alitalo et al. |
| 2009/0087905 A1 | 4/2009 | Achen et al. |
| 2009/0104198 A1 | 4/2009 | Alitalo et al. |

FOREIGN PATENT DOCUMENTS

| | | |
|---|---|---|
| WO | WO-98/07832 | 2/1998 |
| WO | WO-98/33917 | 8/1998 |
| WO | WO-99/46364 | 9/1999 |
| WO | WO-00/45835 | 8/2000 |
| WO | WO-01/51075 | 7/2001 |
| WO | WO-02/29087 | 4/2002 |
| WO | WO-02/083704 | 10/2002 |
| WO | WO-02/083849 | 10/2002 |

OTHER PUBLICATIONS

Ahern, Biochemical, reagent kits offer scientists good return on investment, <www.thescientist.library.upenn.edu/yr1995/july/tools_950724.html>, *The Scientist*, 9: 20 (Jul. 24, 1995).

Akane et al., Direct dideoxy sequencing of genomic DNA by ligation-mediated PCR, *Biotechniques*, 16: 238-41 (1994).

Anderson et al., Human gene therapy, *Nature*, 392: 25-30 (1998).

Aprelikova et al., FLT4, a novel class III receptor tyrosine kinase in chromosome 5q33-qter, *Cancer Res.*, 52: 746-8 (1992).

Barrowman, Gastrointestinal Lymphatics, *Lymph Stasis: Pathophysiology, Diagnosis and Treatment*, Chapter 9, CRC Press, Boca Raton, FL, pp. 211-231 (1991).

Boshart et al., A very strong enhancer Is located upstream of an immediate early gene of human cytomegalovirus, *Cell*, 41: 521-30 (1985).

Boultwood et al., Molecular mapping of uncharacteristically small 5q deletions in two patients with the 5q-syndrome: Delineation of the critical region on 5q and identification of a 5q-breakpoint, *Genomics*, 19: 425-32 (1994).

Browman et al., Comprehensive human genetic maps: Individual and sex-specific variation in recombination, *Am. J. Hum. Genet.*, 63: 861-9 (1998).

Campbell-Beggs et al., Chyloabdomen in a neonatal foal, *Veterinary Record*, 137: 96-8 (1995).

Castenholz, Structure of initial and collecting lymphatic vessels, *Lymph Stasis: Pathophysiology, Diagnosis, and Treatment*, Chapter 2, CRC Press: Boca Raton, FL, pp. 15-42 (1991).

Crystal et al., Transfer of genes to humans: early lessons and obstacles to success, *Science*, 270: 404-10 (1995).

Dale, The inheritance of primary lymphoedema, *J. Med. Genet.*, 22: 274-8 (1985).

Davis et al., Direct gene transfer into skeletal muscle in vivo: Factors affecting efficiency of transfer and stability of expression, *Hum. Gene Ther.*, 4: 151-9 (1993).

Dignam et al., Balbiani ring 3 in *Chironomus tentans* encodes a 185-kDa secretory protein which is synthesized throughout the fourth larval instar, *Gene*, 88: 133-40 (1990).

Ding et al., A single amino acid determines the immunostimulatory activity of interleukin 10, *J. Exp. Med.*, 191: 213-24 (2000).

Douglas et al., Direct sequencing of double-stranded PCR products incorporating a chemiluminescent stection procedure, *Biotechniques*, 14: 824-8 (1993).

Drmanac et al., Accurate sequencing by hybridization for DNA diagnostics and individual genomics, *Nat. Biotechnol.*, 16: 54-8 (1998).

Drmanac et al., DNA sequence determination by hybridization: A strategy for efficient large-scale sequencing, *Science*, 260: 1649-52 (1993).

Dumont et al., Cardiovascular failure in mouse embryos deficient in VEGF receptor-3, *Science*, 282: 946-9 (1998).

Evans et al., Mapping of primary congenital lymphedema to the 5q35.3 region, *Am. J. Hum. Genet.*, 64: 547-55 (1999).

Ferrell et al., Hereditary lymphedema: evidence for linkage and genetic heterogeneity, *Hum. Mol. Genetics*, 7: 2073-8 (1998).

Fischer et al., DNA fragments differing by single base-pair substitutions are separated in denaturing gradient gels: Correspondence with melting theory, *Proc. Natl. Acad. Sci., USA*, 80: 1579-83 (1983).

Fournier et al., Mutation in tyrosine residue 1337 abrogates ligand-dependent transforming capacity of the FLT4 receptor, *Oncogene*, 11: 921-31 (1995).

Fournier et al., Role of tyrosine residues and protein interaction domains of SHC adaptor in VEGF receptor 3 signaling, *Oncogene*, 18: 507-14 (1999).

Fox et al., Angiogenic gene therapy, *Circulation*, 94: 3065-6 (1996).

Galland et al., Chromosomal localization of FLT4, a novel receptor-type tyrosine kinase gene, *Genomics*, 13: 475-8 (1992).

Galland et al., The FLT4 gene encodes a transmembrane tyrosine kinase related to the vascular endothelial growth factor receptor, *Oncogene*, 8: 1233-40 (1993).

Genbank Accession No. AF014827, Rattus norvegicus vascular endothelial growth factor D (VEGF-D) mRNA, complete cds, Aug. 13, 1997.

Genbank Accession No. AJ000185, *Homo sapiens* mRNA for vascular endothelial growth factor-D, Feb. 13, 1998.

Genbank Accession No. Y15837, Coturnix coturnix mRNA for vascular endothelial growth factor C, Dec. 15, 1997.

Genbank Accession No. D89628, Mus musculus mRNA for vascular endothelial growth factor D, complete cds, Dec. 11, 1996.

Genbank Accession No. L07296, Mus musculus receptor tyrosine kinase (FLT4) mRNA, complete cds, Jun. 12, 1993.

Genbank Accession No. P35917, Vascular endothelial growth factor receptor 3 precursor (VEGFR-3) (tyrosine-protein kinase receptor FLT4), Sep. 22, 1994.

Genbank Accession No. S66407, FLT4=receptor tyrosine kinase isoform FLT4 long {3' region, alternatively spliced} [human, mRNA Partial, 216 nt], Dec. 18, 1993.
Genbank Accession No. U73620 (Locus MMU73620) Mus musculus VEGF-C mRNA, complete cds, Jan. 14, 1997.
Genbank Accession No. X68203, Homo sapiens mRNA for FLT4, class III receptor tyrosine kinase, Apr. 21, 1993.
Gene Characterization Kits, Stratagene Catalogue, pp. 39-40 (1988).
Genetic variants and strains of the laboratory mouse, 2nd ed., New York: Oxford University Press, p. 70 (1989).
Gnatenko et al., Characterization of recombinant adeno-associated vir2 as a vehicle for gene delivery and expression into vascular cells, *J. Investig. Med.*, 45: 87-98 (1997).
Greenlee et al., Developmental disorders of the lymphatic system, *Lymphology*, 26: 156-68 (1993).
Holmes et al., Hereditary late-onset lymphedema, *Pediatrics* 61: 575-9 (1978).
Isner et al., Arterial gene therapy for restenosis, *Hum. Gene Ther.*, 7: 989-1011 (1996).
Isner et al., Arterial gene therapy for therapeutic angiogenesis in patients with peripheral artery disease, *Circulation*, 91: 2687-92 (1995).
Jabs et al., A mutation in the homeodomain of the human MSX2 gene in a family affected with autosomal dominant craniosynostosis cell, 75: 443-50 (1993).
Jeltsch et al., Hyperplasia of lymphatic vessels in VEGF-C transgenic mice, *Science*, 276: 1423-5 (1997).
Joukov et al., A novel vascular endothelial growth factor, VEGF-C, is a ligand for the Flt4 (VEGFR-3) and KDR (VEGFR-2) receptor tyrosine kinases, *EMBO J.*, 15: 290-8 (1996).
Joukov et al., A recombinant mutant vascular endothelial growth factor-C that has lost vascular endothelial growth factor receptor-2 binding, activation, and vascular permeability activities, *J. Biol. Chem.*, 273: 6599-602 (1998).
Joukov et al., Proteolytic processing regulates receptor specificity and activity of VEGF-C, *EMBO J.*, 16: 3898-911 (1997).
Jussila et al., Lymphatic endothelium and Kaposi's sarcoma spindle cells detected by antibodies against the vascular endothelial growth factor recetor-3, *Cancer Res.*, 58: 1599-604 (1998).
Kaipainen et al., Expression of the fms-like tyrosine kinase 4 gene becomes restricted to lymphatic endothelium during development, *Proc. Natl. Acad. Sci., USA*, 92: 3566-70 (1995).
Kaipainen et al., The related FLT4, FLT1 and KDR receptor tyrosine kinases show distinct expression patterns in human fetal endothelial cell, *J. Exp. Med.*, 178: 2077-88 (1993).
Karkkainen et al., A model for gene therapy of human hereditary lymphedema, *Proc. Natl. Acad. Sci., USA.*, 98: 12677-82 (2001).
Kieleczawa et al., DNA sequencing by primer walking with strings of contiguous hexamers, *Science*, 258: 1787-91 (1992).
Kim et al., Minimal requirement for a lentivirus vector based on human immunodeficiency virus type 1, *J. Virol.*, 72: 811-6 (1998).
Kimak et al., Linkage and mutation in the vascular endothelial growth factor-C receptor (FLT4) gene in hereditary lymphedema, *Am. J. Hum. Genet.*, 63: A34 (1998) Abstract 180.
Kingsman et al., A new generation of gene therapy vectors, *Scrip Magazine*, 43-6 (1998).
Kinmonth (Ed), *The Lymphatics: Diseases, Lymphography and Surgery*. Edward Arnold Publishers: London, England, pp. 82-86 (1972).
Korhonen et al., Endothelial-specific gene expression directed by the tie gene promoter in vivo, *Blood*, 86: 1828-35 (1995).
Kukk et al., VEGF-C receptor binding and pattern of expression with VEGFR-3 suggests a role in lymphatic vascular development, *Development*, 122: 3829-37 (1996).
Lawrence et al., Vascular endothelial growth factor C: Genomic organization, sequence and variation. *Am. J. Hum. Genet.*, 63(Suppl. ): A185 (1998) Abstract 1053.
Lehner et al., Comparative sequence analysis of human cytomegalovirus strains, *J. Clin. Microbiol.*, 29: 2494-502 (1991).
Levinson, Linkage analysis of hereditary lymphedema to chromosome 5: Preliminary analysis for a genome scan, submitted to the graduate facility of the graduate school of public health in partial fulfillment of the requirements for the degree of Master of Science, University of Pittsburgh, pp. ii-vii and 1-54 (1996).
Lewis et al., Lymphedema praecox, *J. Pediat.*, 104: 641-8 (1984).
Lymboussaki et al., Expression of the vascular endothelial growth factor C receptor VEGFR-3 in lymphatic endothelium of the skin and in vascular tumors. *Am. J. Pathol.*, 153: 395-403 (1998).
Lyon et al., *Mouse News Lett*. 74: 96 (1986).
Lyon et al., Research News, *Mouse News Lett*. 71: 26 (1984).
Maxam et al., Sequencing end-labeled DNA with base-specific chemical cleavages, *Meth. Enzymol.*, 65: 499-560 (1977).
Miller et al., A simple salting out procedure for extracting DNA from human nucleated cells, *Nucl. Acids Res.*, 16: 1215 (1998).
Milroy, An undescribed variety of hereditary edema, *N.Y. Medical J.*, 56: 505-8 (1892).
Mirzabekov, DNA sequencing by hybridization—a megasequencing method and a diagnostic tool? *TIBTECH*, 12: 27-32 (1994).
Mohammadi et al., Structure of the FGF receptor tyrosine kinase domain reveals a novel autoinhibitory mechanism, *Cell*, 86: 577-87 (1996).
Myers et al., Detection of single base substitutions by ribonuclease cleavage at mismatches in RNA: DNA duplexes, *Science*, 230: 1242-6 (1985).
O'Connell et al., PedCheck: A program for identifying marker typing incompatibilities in linkage analysis, *Am. J. Hum. Genet.*, 61: A288 (1997) (Abstract).
O'Connell, J.R. et al., The VITESSE algorithm for rapid exact multilocus linkage analysis via genotype set-recoding and fuzzy inheritance, *Nat. Genet.*, 11: 402-8 (1995).
Offori et al., Angiosarcoma in congenital hereditary lumphoedema (Milroy's Disease)—Diagnostic beacons and a review of the literature, *Clin. Exp. Dermatol.*, 18: 174-7 (1993).
Oh et al., VEGF and VEGF-C: Specific induction of angiogenesis and lymphangiogenesis in the differentiated avian chorioallantoic membrane, *Dev. Biol.*, 188: 96-109 (1997).
Ohkuma, Dermal lymph and lymphatics, *Lymph Stasis: Pathophysiology, Diagnosis and Treatment*, Chapter 7, CRC Press, Boca Raton, FL, pp. 157-189 (1991).
Olszewski, Chemistry of Lymph, *Lymph Stasis: Pathophysiology, Diagnosis, and Treatment*, Chapter 10, CRC Press, Boca Raton, FL, pp. 235-258 (1991).
Orita et al., Detection of polymorphisms of human DNA by gel electrophoresis as single-strand conformation polymorphisms, *Proc. Natl. Acad. Sci., USA*, 86: 2766-70 (1989).
Ott, Computer-simulation methods in human linkage analysis, *Proc. Nat. Acad. Sci., USA*, 86: 4175-9 (1989).
Pajusola et al., FLT4 receptor tyrosine kinase contains seven immuoglobulin-like loops and is expressed in multiple human tissues and cell lines, *Cancer Res.*, 52: 5738-43 (1992).
Pajusola et al., Signaling properties of FLT4, a proteolytically processed receptor tyrosine kinase related to two VEGF receptors, *Oncogene*, 9: 3545-55 (1994).
Pajusola et al., Two human FLT4 receptor tyrosine kinase isoforms with distinct carboxy terminal tails are produced by alternative processing of primary transcripts, *Oncogene* 8: 2931-7 (1993).
Partanen et al., Lack of lymphatic vascular specificity of vascular endothelial growth factor receptor 3 in 185 vascular tumors. *Cancer*, 86: 2406-12 (1999).
Partanen et al., Opposite phehotypes of hypomorphic and Y766 phosphorylation site mutations reveal a function for Fgfr1 in anteroposterior patterning of mouse embryos, *Genes Dev.*, 12: 2332-44 (1998).
Pastinen et al., Minisequencing: A specific tool for DNA analysis and diagnostics on oligonucleotide arrays, *Genome Res.*, 7: 606-14 (1997).
Patterson et al., Hereditary lymphedema, comparative pathology bulletin, 3: 2 (1971).
Paulsson et al., The balbiani ring 3 gene in *Chironomous tentans* has a diverged repetitive structure split by many introns, *J. Mol. Biol.*, 211: 331-49 (1990).
Pease et al., Light-generated oligonucleotide arrays for rapid DNA sequence analysis, *Proc. Natl. Acad. Sci., USA*, 91: 5022-6 (1994).
Quantin et al., Adenovirus as an expression vector in muscle cells in vivo, *Proc. Natl. Acad. Sci., USA*, 89: 2581-4 (1992).
Ramsay, DNA chips: State-of-the-art, *Nat. Biotechnol.*, 16: 40-8 (1998).

Riesner et al., Temperature-gradient gel electrophoresis of nucleic acids: Analysis of conformational transitions, sequence variations, and protein-nucleic acid interactions, *Electrophoresis*, 10: 377-89 (1989).

Roberts et al., Potassium permanganate and tetraethylammonium chloride are a safe and effective substitute for osmium tetroxide in solid-phase fluorescent chemical cleavage of mismatch, *Nucl. Acids Res.*, 25: 3377-8 (1997).

Rosenfeld et al., In vivo transfer of the human cystic fibrosis transmembrane conductance regulator gene to the airway epithelium, *Cell*, 68: 143-55 (1992).

Rowley et al., Ultrarapid mutation detection by multiplex solid-phase chemical cleavage, *Genomics*, 30: 574-82 (1995).

Ruohola et al., Vascular endothelial growth factors are differentially regulated by steroid hormones and antiestrogens in breast cancer cells, *Mol. Cell. Endocrinol.*,149: 29-40 (1999).

Sambrook et al., *Molecular Cloning: A Laboratory Manual*, Second ed., Cold Spring Harbor, New York: Cold Spring Harbor Laboratory Press, §§ 9.47-9.51 (1989).

Sanger et al., DNA sequencing with chain-terminating inihibitors, *Proc. Natl. Acad. Sci., USA*, 74: 5463-7 (1977).

Schafer et al., DNA variation and the future of human genetics, *Nat. Biotechnol.*, 16: 33-9 (1998).

Shumaker et al., Mutation detection by solid phase primer externsion, *Hum. Mutation*, 7: 346-54 (1996).

Stratford-Perricadet et al., Widespread long-term gene transfer to mouse skeletal muscles and heart, *J. Clin. Invest.*, 90: 626-30 (1992).

Taipale et al., Vascular endothelial growth factor receptor-3, *Curr. Top. Microbiol. Immunol.*, 237: 85-96 (1999).

Thompson et al., The cloche and spadetail genes differentially affect hematopoiesis and vasculogenesis, *Dev. Biol.*, 197: 248-69 (1998).

Tsurumi et al., Direct intramuscular gene transfer of naked DNA encoding vascular endothelial growth factor augments collateral development and tissue perfusion, *Circulation*, 34: 3281-90 (1996).

Tsurumi et al., Treatment of acute limb ischemia by intramucular injection of vascular endothelial growth factor gene, *Circulation*, 96: II-382-8 (1997).

Uhley et al., Pulmonary Lymph and Lymphatics, *Lymph Stasis: Pathophysiology, Diagnosis and Treatment*, Chapter 8, CRC Press, Boca Raton, FL, pp. 191-209 (1991).

Valtola et al., VEGFR-3 and its ligand VEGF-C are associated with angoigenesis in breast cancer, *Am. J. Pathol.*, 154: 3801-90 (1999).

Van Der Geer et al., Receptor protein-tyrosine kinases and their signal transduction pathways, *Ann. Rev. Cell. Biol.*, 10: 251-337 (1994).

van der Putte, Congenital hereditary lymphedema in the pig, *Lymphol.*, 11: 1-9 (1978).

Weeks et al., SLINK: A general simulation program for linkage analysis, *Am. J. Hum. Genet.*, 47: A204 (1990) (Abstract).

Wheeler et al., Familial lymphedema praecox: Meige's disease, *Plastic Reconstruct. Surg.*, 67: 362-4 (1981).

White et al., Detecting single base substitutions as heteroduplex polymorphisms, *Genomics*, 12: 301-6 (1992).

Witte et al., Phentypic and genotypic hetherogeneity in familial Milroy lymphedema, *Lymphology*, 31: 145-55 (1998).

Yin et al., Genomic structure of the human KDR/flk-1 gene, Mamm. Genome, 9: 408-10 (1998).

FIG. 3A
```
Human   1 MQRGAALCLRLWLCLGLLDGLVSGYSMTPPTLNITEESHVIDTGDSLSIS  50
          || |||| ||||||||||| || .|||||||||||||:|:||||||||||
Mouse   1 MQPGAALNLRLWLCLGLLQGLANGYSMTPPTLNITEDSYVIDTGDSLSIS  50

H      51 CRGQHPLEWAWPGAQEAPATGDKDSEDTGVVRDCEGTDARPYCKVLLLHE 100
          ||||||||| |||||| || |||||| || |||||:|||||||||| :
M      51 CRGQHPLEWTWPGAQEVLTTGGKDSEDTRVVHDCEGTEARPYCKVLLLAQ 100

H     101 VHANDTGSYVCYYKYIKARIEGTTAASSYVFVRDFEQPFINKPDTLLVNR 150
          |||.|||| |||||||||||||||||||.|||||||.|||||||||||||
M     101 THANNTGSYHCYYKYIKARIEGTTAASTYVFVRDFKHPFINKPDTLLVNR 150

H     151 KDAMWVPCLVSIPGLNVTLRSQSSVLWPDGQEVVWDDRRGMLVSTPLLHD 200
          ||.||||||||||||:||||||||| ||||||||.|||||||| | ||| 
M     151 KDSMWVPCLVSIPGLNITLRSQSSALHPDGQEVLWDDRRGMRVPTQLLRD 200

H     201 ALYLQCETTWGDQDFLSNPFLVHITGNELYDIQLLPRKSLELLVGEKLVL 250
          |||||||||||||.|||| |.|||||||||||||| |:||:|||||||||
M     201 ALYLQCETTWGDQNFLSNLFVVHITGNELYDIQLYPKKSMELLVGEKLVL 250

H     251 NCTVWAEFNSGVTFDWDYPGKQAERGKWVPERRSQQTHTELSSILTIHNV 300
          ||||||||.|||||||||||||||| ||||||||||||||||||||||||
M     251 NCTVWAEFDSGVTFDWDYPGKQAERAKWVPERRSQQTHTELSSILTIHNV 300

H     301 SQHDLGSYVCKANNGIQRFRESTEVIVHENPFISVEWLKGPILEATAGDE 350
          ||.||| |||.|||||||||||||||||||:||||||||||||||||||
M     301 SQNDLGPYVCEANNGIQRFRESTEVIVHEKPFISVEWLKGPVLEATAGDE 350

H     351 LVKLPVKLAAYPPPEFQWYKDGKALSGRHSPHALVLKEVTEASTGTYTLA 400
          ||||||||||||||||||||||  |||.||||||||||||||| | ||||
M     351 LVKLPVKLAAYPPPEFQWYKDRKAVTGRHNPHALVLKEVTEASAGVYTLA 400

H     401 LWNSAAGLRRNISLELVVNVPPQIHEKEASSPSIYSRHSRQALTCTAYGV 450
          |||||||||.|||||||||||||||||||||||||||||||| |||||||
M     401 LWNSAAGLRQNISLELVVNVPPHIHEKEASSPSIYSRHSRQTLTCTAYGV 450

H     451 PLPLSIQWHWRPWTPCKMFAQRSLRRRQQQDLMPQCRDWRAVTTQDAVNP 500
          | |||:||||||||||| |||||||||||.|||||||||: |||||||||
M     451 PQPLSVQWHWRPWTPCKTFAQRSLRRRQQRDGMPQCRDWKEVTTQDAVNP 500

H     501 IESLDTWTEFVEGKNKTVSKLVIQNANVSAMYKCVVSNKVGQDERLIYFY 550
          |||||.||||||||||||||||||.|||||||||||||||||||||||||
M     501 IESLDSWTEFVEGKNKTVSKLVIQDANVSAMYKCVVVNKVGQDERLIYFY 550

H     551 VTTIPDGFTIESKPSEELLEGQPVLLSCQADSYKYEHLRWYRLNLSTLHD 600
          ||||||||.|||.|||: |||| |||.||.| ||||||||||||||||||
M     551 VTTIPDGFSIESEPSEDPLEGQSVRLSCRADNYTYEHLRWYRLNLSTLHD 600

H     601 AHGNPLLLDCKNVHLFATPLAASLEEVAPGARHATLSLSIPRVAPEHEGH 650
          | ||||||||||||||||||| .||| ||||||||||.||||||||| ||
M     601 AQGNPLLLDCKNVHLFATPLEANLEEAEPGARHATLSLNIPRVAPEDEGD 650

H     651 YVCEVQDRRSHDKHCHKKYLSVQALEAPRLTQNLTDLLVNVSDSLEMQCL 700
          ||||||||||.|||||||||||||||||||||||||||||||||||| |
M     651 YVCEVQDRRSQDKHCHKKYLSVQALEAPRLTQNLTDLLVNVSDSLEMRCP 700
```

```
H  701  VAGAHAPSIVWYKDERLLEEKSGVDLADSNQKLSIQRVREEDAGRYLCSV  750
        |||||  |||||||||||||..||:||||||||:||||||||||||||||
M  701  VAGAHVPSIVWYKDERLLEKESGIDLADSNQRLSIQRVREEDAGRYLCSV  750

H  751  CNAKGCVNSSASVAVEGSEDKGSMEIVILVGTGVIAVFFWVLLLLIFCNM  800
        |||||||||||||||||||||||||||||:||||||||||||||||||||
M  751  CNAKGCVNSSASVAVEGSEDKGSMEIVILIGTGVIAVFFWVLLLLIFCNM  800

H  801  RRPAHADIKTGYLSIIMDPGEVPLEEQCEYLSYDASQWEFPRERLHLGRV  850
        :|||||||||||||||||||||||||||||||||||||||||||||||||
M  801  KRPAHADIKTGYLSIIMDPGEVPLEEQCEYLSYDASQWEFPRERLHLGRV  850

H  851  LGYGAFGKVVEASAFGIHKGSSCDTVAVKMLKEGATASEHRALMSELKIL  900
        ||:||||||||||||||-||||||||||||||||||||||||||||||||
M  851  LGHGAFGKVVEASAFGINKGSSCDTVAVKMLKEGATASEHRALMSELKIL  900
             G857R

H  901  IHIGNHLNVVNLLGACTKPQGPLMVIVEFCKYGNLSNFLRAKRDAFSPCA  950
        |||||||||||||||||| ||||||||||||||||||||| ||| |.| |
M  901  IHIGNHLNVVNLLGACTKPNGPLMVIVEFCKYGNLSNFLRVKRDTFNPYA  950

H  951  EKSPEQRGRFRAMVELARLDRRRPGSSDRVLFARFSKTEGGARRASPDQE  1000
        ||||||| |||||||:||||||||||||||||||:|||||  .| |||  ||
M  951  EKSPEQRRRFRAMVEGAKADRRRPGSSDRALFTRFLMGKGSARRAPLVQE  1000

H 1001  AEDLWLSPLTMEDLVCYSFQVARGMEFLASRKCIHRDLAARNILLSESDV  1050
        |||||||||||||||||||||||||||||||||||||||||||||||||:
M 1001  AEDLWLSPLTMEDLVCYSFQVARGMEFLASRKCIHRDLAARNILLSESDI  1050
                                         R1041P  D1049N
                                         L1044P

H 1051  VKICDFGLARDIYKDPDYVRKGSARLPLKWMAPESIFDKVYTTQSDVWSF  1100
        |||||||||||||||||||||||||||||||||||||||||||||||||
M 1051  VKICDFGLARDIYKDPDYVRKGSARLPLKWMAPESIFDKVYTTQSDVWSF  1100
             I1053N (Chy mouse mutation)

H 1101  GVLLWEIFSLGASPYPGVQINEEFCQRLRDGTRMRAPELATPAIRRIMLN  1150
        |||||||||||||||||||||||||||:|||||||||||||||||  || .
M 1101  GVLLWEIFSLGASPYPGVQINEEFCQRLKDGTRMRAPELATPAIRHIMQS  1150
             P1114L

H 1151  CWSGDPKARPAFSELVEILGDLLQGRGLQEEEEVCMAPRSSQSSEEGSFS  1200
        ||||||||||||||:|||||||||| |  |||| ||  |||||||  |
M 1151  CWSGDPKARPAFSDLVEILGDLLQGGWQEEEEERMALHSSQSSEEDGFM  1200

H 1201  QVSTMALHIAQADAEDSPPSLQRHSLAARYYNWVSFPGCLARGAETRGSS  1250
        | || |||| :|||:|||||: |||||||||| |||| |||| .| |||
M 1201  QASTTALHITEADADDSPPSMHCHSLAARYYNCVSFPGRLARGTKPGSS  1250

H 1251  RMKTFEEFPMTPTTYKGSVDNQTDSGMVLASEEFEQIESRHRQESGF  1297
        |||||||  ||||||||| -|||||||||||||||::|||||  |  |
M 1251  RMKTFEELPMTPTTYKASMDNQTDSGMVLASEEFEELESRHRPEGSF  1297
```

```
1    M R S S Q S T L E R S E Q Q T R A A S S L E E L L R I T H S  VEGF-D
1    H T - - - - - - - - - - - - - - - - - - - - - V L Y P       VEGF-C
1    M S - - - - - - - - - - - - - - - - - - P L - - - - -       h VEGF-B
1    M - - - - - - - - - - - - - - - - - - - - - N F L L S       h VEGF 165
1    M P - - - - - - - - - - - - - - - - - - V H R L F P C       hPlGF

31   E D W K L W R C R L R L K S F - - - - - - T S H D S R S A   VEGF-D
7    E Y H K H Y K C Q L R K G G W Q H - N R E Q A N L N S R T - VEGF-C
5    - - - - L R R L L A A L L Q L A P A Q A P V S Q P D A       h VEGF-B
7    - - H V E H S L A L L - Y L H H A K W S Q A A P M A E G G   h VEGF 165
10   - - F L Q L L A G L A L P A V P P Q Q W A - - - - L S A G N hPlGF

54   S H R S T R F A A T F Y D I E T L K V I D E E W Q R T Q C S VEGF-D
35   - E E T I K F A A A H Y N T E I L K S I D N E H R K T Q C H VEGF-C
29   P G H - - - - - - - - - - Q R K V V S W L D V - Y T R A T C Q h VEGF-B
34   G Q N - - - - - - - - - - H H E V V K F M D V - Y Q R S Y C H h VEGF 165
34   G S S - - - - - - - - - - E V E V V P F Q E V - W G L H S Y C R hPlGF

84   P R E T C V E V A S E L G K S T N T F F K P P C V N V R C   VEGF-D
64   P R E V C I D V G K E F G V A T N T F F K P P C V S V Y R C VEGF-C
49   P R E V V V P L T V E L H G T V A K Q L V P S C V T V Q R C h VEGF-B
54   P I E T L V D I F Q E Y P D E I E Y I F K P S C V P L M R C h VEGF 165
54   A L E R L V D V V S E Y P S E V E H M F S P S C V S L L R C hPlGF

114  G G C C N E E S L I C M N T S T S Y I S K Q L F E I S V P L VEGF-D
94   G G C C N S E G L Q C M N T S T S Y L S K T L F E I T V P L VEGF-C
79   G G C C P D D G L E C V P T G Q H Q V R M Q I L M I R - - - h VEGF-B
84   G G C C N D E G L E C V P T E E S N I T M Q I M R I K P - - h VEGF 165
84   T G C C G D E N L H C V P V E T A N V T M Q L L K L R S - - hPlGF

144  T S V P E L V P V K V A N H T G C K C L P T A P - - R H P Y VEGF-D
124  S Q G P K P V T I S F A N H T S C R C M S K L D V Y R Q V H VEGF-C
106  Y P S S Q T G E M S L E E H S Q C E C - - - - - - - - - - - h VEGF-B
112  H Q G Q H I G E M S F L Q H N K C E C - - - - - - - - - - - h VEGF 165
112  G D R P S Y V E L T F S Q H V R C E C - - - - - - - - - - - hPlGF

172  S I I R R S I Q I P E E D R C S H S K K L C P I D M L W D S VEGF-D
154  S I I R R S L P - A T L P Q C Q A A N K T C P T N Y M W N N VEGF-C
125  - - - - R P K K K D S A V K P D S P R P L C P - - - - - - - h VEGF-B
131  - - - - R P K K D R - - A R Q E N P - - - C G - - - - - - - h VEGF 165
131  - - - - R P L R E K - - M K - - - - - - - - - - - - - - -   hPlGF

202  N K C K C V L Q E E N P L A G T E D - - - - - - - - - - - - VEGF-D
183  H I C R C L A Q E D F M F S S D A G D D S T D G F H D I C G VEGF-C
144  - - - R C T Q H H Q R - - - - P - - - - - - - - - - - - -   h VEGF-B
145  - - - P C S E R R K H L F V Q - - - - - - - - - - - - - -   h VEGF 165
139  - - - - P E R R R P - - - - - - - - - - - - - - - - - - - - hPlGF

220  - H S H L Q E - - - - - - - - - - - - - - - - - - - - - -   VEGF-D
213  P N K E L D E E T C Q C V C R A G L R P A S C G P H K E L D VEGF-C
153  - - - - - - - - - - - - - - - - - - - - - - - - - - - - D   h VEGF-B
157  - - - - - - - - - - - - - - - - - - - - - - - - - - - - D   h VEGF 165
145  - - - - - - - - - - - - - - - - - - - - - - - - - - - - -   hPlGF

226  - - - - - - - - - - - - P A L C G P H M M F D E D R C E C   VEGF-D
243  R N S C Q C V C K N K L F P S Q C G A N R E F D E N T C Q C VEGF-C
154  P R T C R C R C R R R S F - - - - - - - - - - - - - - - -   h VEGF-B
158  P Q T C K C S C K N T D - - - - - - - - - - - - - - - - -   h VEGF 165
145  - - - - - - - K G R G - - - - - - - - - - - - - - - - - -   hPlGF

243  V C K T P C P K D L I Q H P K N C S C F E C K E S L E T C C VEGF-D
273  Y C K R T C P R N Q P L N P G K C A C - E C T E S P Q K C L VEGF-C
167  - - - - - - - - - - - - - - - - - - - - - - L R C Q         h VEGF-B
170  - - - - - - - - - - - - - - - - - - - - - - S R C K         h VEGF 165
149  - - - - - - - - - - - - - - - - - - - - - - K R R R         hPlGF

273  Q K H K L F H P D T C S C E D R - C P F H T R P C A S G K T VEGF-D
302  L N G K K F H H Q T C S C Y R R P C T N R Q K A C E P G F S VEGF-C
171  G R G L E L N P D T C R C - - - - - - - - - - - - - - - -   h VEGF-B
174  A R Q L E L N E R T C R C - - - - - - - - - - - - - - - -   h VEGF 165
153  E K Q R P T D C H L C G D - - - - - - - - - - - - - - - -   hPlGF

302  A C A K H C R F P K E K R A A Q G P H S R K N P             VEGF-D
332  Y S E E V C R C V P S Y W - - - - - K R P Q M S             VEGF-C
184  - - - - - - - - - - - - - - - - R K L R R                   h VEGF-B
187  - - - - - - - - - - - - - - - - D K P R R                   h VEGF 165
166  - - - - - - - - - - - - - - - - A V P R R                   hPlGF
```

METHOD OF TREATMENT FOR LYMPHEDEMA COMPRISING ADMINISTERING A POLYNUCLEOTIDE ENCODING VEGF-D

This application is a divisional of U.S. patent application Ser. No. 12/941,034 filed Nov. 6, 2010, now abandoned, which is a continuation of U.S. patent application Ser. No. 12/366,359, tiled Feb. 5, 2009, now U.S. Pat. No. 7,829,536, which is a continuation of U.S. patent application Ser. No. 11/617,045 filed Dec. 28, 2006, abandoned, which is a divisional of U.S. patent application Ser. No. 10/661,740, filed Sep. 12, 2003, abandoned, which is a divisional of U.S. application Ser. No. 09/375,248, filed Aug. 16, 1999, now U.S. Pat. No. 6,764,820, which is a Continuation-in-Part of International Patent Application No. PCT/US99/06133, tiled Mar. 26, 1999, incorporated herein by reference in its entirety.

ACKNOWLEDGMENT OF GOVERNMENT SUPPORT

This invention was made with United States and Finnish government support, including support under contract R03-HD35174, awarded by the U.S. National Institutes of Health. The U.S. Government has certain rights in this invention.

FIELD OF THE INVENTION

The present invention relates generally to the fields of molecular biology and medicine; more particularly to the areas of genetic screening and the identification and treatment of hereditary disorders; and more particularly to identification and treatment of hereditary lymphedema.

DESCRIPTION OF RELATED ART

The lymphatic system is a complex structure organized in parallel fashion to the circulatory system. In contrast to the circulatory system, which utilizes the heart to pump blood throughout the body, the lymphatic system pumps lymph fluid using the inherent contractility of the lymphatic vessels. The lymphatic vessels are not interconnected in the same manner as the blood vessels, but rather form a set of coordinated structures including the initial lymphatic sinuses [Jeltsch et al., *Science*, 276:1423-1425 (1997); and Castenholz, A., in Olszewski, W. L. (ed.), *Lymph Stasis: Pathophysiology, Diagnosis, and Treatment*. CRC Press: Boca Raton, Fla. (1991), pp. 15-42] which drain into the lymphatic capillaries and subsequently to the collecting lymphatics which drain into the lymphatic trunks and the thoracic duct which ultimately drains into the venous circulation. The composition of the channels through which lymph passes is varied [Olszewski, W. L., in Olszewski, W. L. (ed), *Lymph Stasis Pathophysiology, Diagnosis, and Treatment*. CRC Press: Boca Raton, Fla. (1991), pp. 235-258; and Kinmonth, J. B., in Kinmonth, J. B. (ed), *The Lymphatics: Diseases, Lymphography and Surgery*. Edward Arnold Publishers: London, England (1972), pp. 82-86], including the single endothelial layers of the initial lymphatics, the multiple layers of the collecting lymphatics including endothelium, muscular and adventitial layers, and the complex organization of the lymph node. The various organs of the body such as skin, lung, and GI tract have components of the lymphatics with various unique features. [See Ohkuma, M., in Olszewski (1991), supra, at pp. 157-190; Uhley, H. and Leeds, S., in Olszewski (1991), supra, at pp. 191-210; and Barrowman, J. A., in Olszewski (1991), at pp. 221-234).]

Molecular biology has identified at least a few genes and proteins postulated to have roles mediating the growth and/or embryonic development of the lymphatic system. One such gene/protein is the receptor tyrosine kinase designated Flt4 (fms-like tyrosine kinase 4), cloned from human erythroleukaemia cell and placental cDNA libraries. [See U.S. Pat. No. 5,776,755; Aprelikova et al., *Cancer Res.*, 52: 746-748 (1992); Galland et al., *Genomics*, 13: 475-478 (1992); Galland et al., *Oncogene*, 8: 1233-1240 (1993); and Pajusola et al., *Cancer Res.*, 52:5738-5743 (1992), all incorporated herein by reference.] Studies showed that, in mouse embryos, a targeted disruption of the Flt4 gene leads to a failure of the remodeling of the primary vascular network, and death after embryonic day 9.5 [Dumont et al., *Science*, 282: 946-949 (1998)]. These studies suggested that Flt4 has an essential role in the development of the embryonic vasculature, before the emergence of the lymphatic vessels. However, additional studies indicated that, during further development, the expression of Flt4 becomes restricted mainly to lymphatic vessels [Kaipainen, et al., *Proc. Neal. Acad. Sci. USA*, 92: 3566-3570 (1995)].

In humans, there are two isoforms of the Flt4 protein, designated as Flt4s (short, Genbank Accession No. X68203) and Flt4l (long, Genbank Accession Nos. X68203 and S66407, SEQ ID NO: 1). The sequence of these isoforms is largely identical, except for divergence that occurs at the carboxyl terminus of the receptor as a result of alternative mRNA splicing at the 3' end. The C-terminus of the long form contains three tyrosyl residues, and one of them (Y1337 (SEQ ID NO: 2)) serves as an autophosphorylation site in the receptor [Fournier et al., *Oncogene*, 11: 921-931 (1995); and Pajusola, et al., *Oncogene*, 8: 2931-2937 (1993)]. Only the long form is detected in human erythroleukaemia (HEL) and in a megakaryoblastic cell line (the DAMI cells), and the mouse Flt4 gene (Genbank Accession No. L07296) only produces one mRNA transcript, corresponding to Flt4l [Galland et al., *Oncogene*, 8: 1233-1240 (1993); and Pajusola et al., *Cancer Res.*, 52: 5738-5743 (1992)]. These findings suggest that the long form of Flt4 may be responsible for most of the biological properties of this receptor. The Flt4 protein is glycosylated and proteolytically processed in transfected cells [Pajusola et al., *Oncogene*, 9: 3545-3555 (1994)]. During this process, the 175 kD form of the receptor matures to a 195 kD form, which is subsequently cleaved into a 125 kD C-terminal fragment, and a 75 kD extracellular domain-containing fragment, which are linked by disulphide bonding in the mature receptor.

Two growth factors, named vascular endothelial growth factors C and D (VEGF-C and VEGF-D) due to amino acid sequence similarity to earlier-discovered vascular endothelial growth factor, have been shown to bind and activate the tyrosine phosphorylation of Flt4. [Achen et al., *Proc. Natl. Acad. Sci. USA*, 95: 548-553 (1998); Joukov et al, *EMBO J.*, 16: 3898-3911; and Joukov et al., *EMBO J.*, 15: 290-298 (1996)]. Because of Flt4's growth factor binding properties and the fact that Flt4 possesses amino acid sequence similarity to two previously identified VEGF receptors (Flt1/VEGFR-1 and KDR/VEGFR-2), Flt4 has also been designated VEGFR-3, and these terms are used interchangeably herein.

When VEGF-C was intentionally over-expressed under a basal keratin promoter in transgenic mice, a hyperplastic lymphatic vessel network in the skin was observed. [Jeltsch et al. *Science*, 276:1423-1425 (1997).] The results of this study, when combined with the expression pattern of VEGFR-3 in the lymphatic vasculature, suggest that lymphatic growth may be induced by VEGF-C and mediated via VEGFR-3. Notwithstanding the foregoing insights involving one cell surface receptor and the two apparent ligands therefor, little is known about the developmental regulation of the lymphatic system.

Hereditary or primary lymphedema, first described by Milroy in 1892 [Milroy, *N.Y. Med. J.*, 56:505-508 (1892)], is a developmental disorder of the lymphatic system which leads to a disabling and disfiguring swelling of the extremities. Hereditary lymphedema generally shows an autosomal dominant pattern of inheritance with reduced penetrance, variable expression, and variable age-at-onset [Greenlee et al., *Lymphology*, 26:156-168 (1993)]. Swelling may appear in one or all limbs, varying in degree and distribution. If untreated, such swelling worsens over time. In rare instances, angiosarcoma may develop in affected tissues [Offori et al., *Clin. Exp. Dermatol.*, 18:174-177 (1993)]. Despite having been described over a century ago, little progress has been made in understanding the mechanisms causing lymphedema. A long-felt need exists for the identification of the presumed genetic variations that underlie hereditary lymphedema, to permit better informed genetic counseling in affected families, earlier diagnosis and treatment, and the development of more targeted and effective lymphedema therapeutic regimens. In addition, identification of genetic markers and high risk members of lymphedema families facilitates the identification and management of environmental factors that influence the expression and severity of a lymphedema phenotype.

SUMMARY OF THE INVENTION

The present invention provides materials and methods that address one or more of the long-felt needs identified above by identifying a genetic marker that correlates and is posited to have a causative role in the development of hereditary lymphedema. The invention is based in part on the discovery that, in several families with members afflicted with hereditary lymphedema, the lymphedema phenotype correlates with genetic markers localized to chromosome 5q34-q35; and that in at least some such families, a missense mutation in the VEGFR-3 gene (which maps to chromosome 5q34-q35) exists that appears to behave in a loss-of-function dominant negative manner to decrease tyrosine kinase signaling of the receptor. In view of the fact that VEGFR-3 acts as a high affinity receptor for vascular endothelial growth factor C. (VEGF-C), a growth factor whose effects include modulation of the growth of the lymphatic vascular network, these linkage and biochemical studies provide an important marker for determining a genetic predisposition for lymphedema in healthy individuals; and for diagnosing hereditary lymphedema in symptomatic individuals. Materials and Methods for performing such genetic analyses are considered aspects of the present invention.

Thus, the invention provides genetic screening procedures that entail analyzing a person's genome—in particular their VEGFR-3 alleles—to determine whether the individual possesses a genetic characteristic found in other individuals that are considered to be afflicted with, or at risk for, developing hereditary lymphedema.

For example, in one embodiment, the invention provides a method for determining a hereditary lymphedema development potential in a human subject comprising the steps of analyzing the coding sequence of the VEGFR-3 genes from the human subject; and determining hereditary lymphedema development potential in said human subject from the analyzing step.

In another embodiment, the invention provides a method of screening a human subject for an increased risk of developing a lymphatic disorder, comprising the steps of: (a) assaying nucleic acid of a human subject to determine a presence or an absence of a mutation altering the encoded VEGFR-3 amino acid sequence or expression of at least one VEGFR-3 allele; and (b) screening for an increased risk of developing a lymphatic disorder from the presence or absence of said mutation.

By "human subject" is meant any human being, human embryo, or human fetus. It will be apparent that methods of the present invention will be of particular interest to individuals that have themselves been diagnosed with lymphedema or have relatives that have been diagnosed with lymphedema.

By "screening for an increased risk" is meant determination of whether a genetic variation exists in the human subject that correlates with a greater likelihood of developing lymphedema than exists for the human population as a whole, or for a relevant racial or ethnic human sub-population to which the individual belongs. Both positive and negative determinations (i.e., determinations that a genetic predisposition marker is present or is absent) are intended to fall within the scope of screening methods of the invention. In preferred embodiments, the presence of a mutation altering the sequence or expression of at least one Flt4 receptor tyrosine kinase allele in the nucleic acid is correlated with an increased risk of developing a lymphatic disorder, whereas the absence of such a mutation is reported as a negative determination.

By "lymphatic disorder" is meant any clinical condition affecting the lymphatic system, including but not limited to lymphedemas, lymphangiomas, lymphangiosarcomas, lymphangiomatosis, lymphangiectasis, and cystic hygroma. Preferred embodiments are methods of screening a human subject for an increased risk of developing a lymphedema disorder, i.e., any disorder that physicians would diagnose as lymphedema and that is characterized by swelling associated with lymph accumulation, other than lymphedemas for which non-genetic causes (e.g., parasites, surgery) are known. By way of example, lymphedema disorders include Milroy-Nonne (OMIM 153100) syndrome-early onset lymphedema [Milroy, *N.Y. Med. J.*, 56:505-508 (1892); and Dale, *J. Med. Genet.*, 22: 274-278 (1985)] and lymphedema praecox (Meige syndrome, OMIM 153200)-late onset lymphedema [Lewis et al., *J. Ped.*, 104:641-648 (1984); Holmes et al., *Pediatrics* 61:575-579 (1978); and Wheeler et al., *Plastic Reconstructive Surg.*, 67:362-364 (1981)] which generally are described as separate entities, both characterized by dominant inheritance. However, there is confusion in the literature about the separation of these disorders. In Milroy's syndrome, the presence of edema, which is usually more severe in the lower extremities, is seen from birth. Lymphedema praecox presents in a similar fashion but the onset of swelling is usually around puberty. Some cases have been reported to develop in the post-pubertal period. In the particular analyses described herein, the lymphedema families showing linkage to 5q34-q35 show an early onset for most affected individuals, but individuals in these pedigrees have presented during or after puberty.

The "assaying" step of the invention may involve any techniques available for analyzing nucleic acid to determine its characteristics, including but not limited to well-known techniques such as single-strand conformation polymorphism analysis (SSCP) [Orita et al., *Proc Natl. Acad. Sci. USA*, 86: 2766-2770 (1989)]; heteroduplex analysis [White et al., *Genomics*, 12: 301-306 (1992)]; denaturing gradient gel electrophoresis analysis [Fischer et al., *Proc. Natl. Acad. Sci. USA*, 80: 1579-1583 (1983); and Riesner et al., *Electrophoresis*, 10: 377-389 (1989)]; DNA sequencing; RNase cleavage [Myers et al., *Science*, 230: 1242-1246 (1985)]; chemical cleavage of mismatch techniques [Rowley et al., *Genomics*, 30: 574-582 (1995); and Roberts et al., *Nucl. Acids Res.*, 25:

3377-3378 (1997)]; restriction fragment length polymorphism analysis; single nucleotide primer extension analysis [Shumaker et al., *Hum. Mutat.*, 7: 346-354 (1996); and Pastinen et al., *Genome Res.*, 7: 606-614 (1997)]; 5 □nuclease assays [Pease et al., *Proc. Natl. Acad. Sci. USA*, 91:5022-5026 (1994)]; DNA Microchip analysis [Ramsay, G., *Nature Biotechnology*, 16: 40-48 (1999); and Chee et al., U.S. Pat. No. 5,837,832]; and ligase chain reaction [Whiteley et al., U.S. Pat. No. 5,521,065]. [See generally, Schafer and Hawkins, *Nature Biotechnology*, 16: 33-39 (1998).] All of the foregoing documents are hereby incorporated by reference in their entirety.

In one preferred embodiment, the assaying involves sequencing of nucleic acid to determine nucleotide sequence thereof, using any available sequencing technique. [See, e.g., Sanger et al., *Proc. Natl. Acad. Sci. (USA)*, 74: 5463-5467 (1977) (dideoxy chain termination method); Mirzabekov, *TIBTECH*, 12: 27-32 (1994) (sequencing by hybridization); Dimanac et al., *Nature Biotechnology*, 16: 54-58 (1998); U.S. Pat. No. 5,202,231; and *Science*, 260: 1649-1652 (1993) (sequencing by hybridization); Kieleczawa et al., *Science*, 258: 1787-1791 (1992) (sequencing by primer walking); (Douglas et al., *Biotechniques*, 14: 824-828 (1993) (Direct sequencing of PCR products); and Akane et al., *Biotechniques* 16: 238-241 (1994); Maxam and Gilbert, *Meth. Enzymol.*, 65: 499-560 (1977) (chemical termination sequencing), all incorporated herein by reference.] The analysis may entail sequencing of the entire VEGFR-3 gene genomic DNA sequence, or portions thereof; or sequencing of the entire VEGFR-3 coding sequence or portions thereof. In some circumstances, the analysis may involve a determination of whether an individual possesses a particular VEGFR-3 allelic variant, in which case sequencing of only a small portion of nucleic acid—enough to determine the sequence of a particular codon characterizing the allelic variant—is sufficient. This approach is appropriate, for example, when assaying to determine whether one family member inherited the same allelic variant that has been previously characterized for another family member, or, more generally, whether a person's genome contains an allelic variant that has been previously characterized and correlated with heritable lymphedema. More generally, the sequencing may be focused on those portions of the VEGFR-3 sequence that encode a VEGFR-3 kinase domain, since several different and apparently causative mutations in affected individuals that have been identified correspond to residues within an intracellular VEGFR-3 kinase domain. Referring to SEQ ID NOs: 1 and 2, the two kinase domains of human wild type VEGFR-3 correspond to nucleotides 2546 to 2848 and 3044 to 3514 of SEQ ID NO: 1, which encode residues 843 to 943 and 1009 to 1165 of SEQ ID NO: 2. Such kinase domains are localized to exons 17-20 and 22-26 in the VEGFR-3 gene, so the sequencing/analysis may be focused on those exons in particular. Molecular modeling suggests that, within these domains, residues G852, G854, G857, K879, E896, H1035, D1037, N1042, D1055, F1056, G1057, E1084, D1096, and R1159 are of particular importance in comprising or shaping the catalytic pocket of the VEGFR-3 kinase domains, so the sequencing may focus on these residues (in addition to residues described herein for which mutations have already been identified).

In a related embodiment, the invention provides PCR primers useful for amplifying particular exon sequences of human VEGFR-3 genomic DNA. The Examples below identify preferred primers for amplifying Exon 17, Exon 22, and Exon 24 sequences, where specific missense mutations described herein map. In addition, the Examples below describe the Exon-Intron junctions of human VEGFR-3, which, in combination with the VEGFR-3 cDNA sequence provided herein, permit the manufacture of appropriate oligonucleotide primers for other exons. Any such primers of, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more nucleotides that are identical or exactly complementary to a human VEGFR-3 genomic sequence and that includes or is within 50 nucleotides of a VEGFR-3 exon-intron splice site is intended to be within the scope of the invention.

In another embodiment, the assaying step comprises performing a hybridization assay to determine whether nucleic acid from the human subject has a nucleotide sequence identical to or different from one or more reference sequences. In a preferred embodiment, the hybridization involves a determination of whether nucleic acid derived from the human subject will hybridize with one or more oligonucleotides, wherein the oligonucleotides have nucleotide sequences that correspond identically to a portion of the VEGFR-3 gene sequence, preferably the VEGFR-3 coding sequence set forth in SEQ ID NO: 1, or that correspond identically except for one mismatch. The hybridization conditions are selected to differentiate between perfect sequence complementarity and imperfect matches differing by one or more bases. Such hybridization experiments thereby can provide single nucleotide polymorphism sequence information about the nucleic acid from the human subject, by virtue of knowing the sequences of the oligonucleotides used in the experiments.

Several of the techniques outlined above involve an analysis wherein one performs a polynucleotide migration assay, e.g., on a polyacrylamide electrophoresis gel, under denaturing or non-denaturing conditions. Nucleic acid derived from the human subject is subjected to gel electrophoresis, usually adjacent to one or more reference nucleic acids, such as reference VEGFR-3 sequences having a coding sequence identical to all or a portion of SEQ ID NO: 1, or identical except for one known polymorphism. The nucleic acid from the human subject and the reference sequence(s) are subjected to similar chemical or enzymatic treatments and then electrophoresed under conditions whereby the polynucleotides will show a differential migration pattern, unless they contain identical sequences. [See generally Ausubel et al. (eds.), *Current Protocols in Molecular Biology*, New York: John Wiley & Sons, Inc. (1987-1999); and Sambrook et al., (eds.), Molecular Cloning, *A Laboratory Manual*, Cold Spring Harbor, N.Y.: Cold Spring Harbor Laboratory Press (1989), both incorporated herein by reference in their entirety.]

In the context of assaying, the term "nucleic acid of a human subject" is intended to include nucleic acid obtained directly from the human subject (e.g., DNA or RNA obtained from a biological sample such as a blood, tissue, or other cell or fluid sample); and also nucleic acid derived from nucleic acid obtained directly from the human subject. By way of non-limiting examples, well known procedures exist for creating cDNA that is complementary to RNA derived from a biological sample from a human subject, and for amplifying (e.g., via polymerase chain reaction (PCR)) DNA or RNA derived from a biological sample obtained from a human subject. Any such derived polynucleotide which retains relevant nucleotide sequence information of the human subject [s own DNA/RNA is intended to fall within the definition of "nucleic acid of a human subject" for the purposes of the present invention.

In the context of assaying, the term "mutation" includes addition, deletion, and/or substitution of one or more nucleotides in the VEGFR-3 gene sequence. The invention is demonstrated by way of non-limiting examples set forth below that identify several mutations in VEGFR-3, including single nucleotide polymorphisms that introduce missense mutations into the VEGFR-3 coding sequence (as compared to the VEGFR-3 cDNA sequence set forth in SEQ ID NO: 1) and other polymorphisms that occur in introns and that are identifiable via sequencing, restriction fragment length polymorphism, or other techniques. Example 2 provides an assay to determine whether a VEGFR-3 mutation inhibits VEGFR-3 signaling. Additional assays to study both ligand binding and signaling activities of VEGFR-3 are disclosed, e.g., in U.S. Pat. No. 5,776,755 and International Patent Publication No. WO 98/33917, published 6 Aug. 1998, both of which are incorporated herein by reference in their entirety. Evidence that a VEGFR-3 mutation inhibits VEGFR-3 signaling is evidence that the mutation may have a causative role in lymphedema phenotype. However, even mutations that have no apparent causative role may serve as useful markers for heritable lymphedema, provided that the appearance of the mutation correlates reliably with the appearance of lymphedema.

In a related embodiment, the invention provides a method of screening for a VEGFR-3 hereditary lymphedema genotype in a human subject, comprising the steps of: (a) providing a biological sample comprising nucleic acid from a human subject; (b) analyzing the nucleic acid for the presence of a mutation or mutations in a VEGFR-3 allele in the nucleic acid of the human subject; (c) determining a VEGFR-3 genotype from said analyzing step; and (d) correlating the presence of a mutation in a VEGFR-3 allele with a hereditary lymphedema genotype. In a preferred embodiment, the biological sample is a cell sample containing human cells that contain genomic DNA of the human subject.

Although more time consuming and expensive than methods involving nucleic acid analysis, the invention also may be practiced by assaying protein of a human subject to determine the presence or absence of an amino acid sequence variation in VEGFR-3 protein from the human subject. Such protein analyses may be performed, e.g., by fragmenting VEER-3 protein via chemical or enzymatic methods and sequencing the resultant peptides; or by Western analyses using an antibody having specificity for a particular allelic variant of VEGFR-3.

The invention also provides materials that are useful for performing methods of the invention. For example, the present invention provides oligonucleotides useful as probes in the many analyzing techniques described above. In general, such oligonucleotide probes comprise 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides that have a sequence that is identical, or exactly complementary, to a portion of a human VEGFR-3 gene sequence, or that is identical or exactly complementary except for one nucleotide substitution. In a preferred embodiment, the oligonucleotides have a sequence that corresponds in the foregoing manner to a human VEGFR-3 coding sequence, and in particular, the VEGFR-3 coding sequence set forth in SEQ ID NO: 1. In one variation, an oligonucleotide probe of the invention is purified and isolated. In another variation, the oligonucleotide probe is labeled, e.g., with a radioisotope, chromophore, or fluorophore. In yet another variation, the probe is covalently attached to a solid support. [See generally Ausubel et al. And Sambrook et al., supra.]

In preferred embodiments, the invention comprises an oligonucleotide probe useful for detecting one or more of several mutations that have been characterized herein in affected individuals, including:
(1) a missense mutation at nucleotide 3360 of SEQ ID NO: 1, causing a proline to leucine change at residue 1114 in SEQ ID NO: 2;
(2) a missense mutation at nucleotide 2588 of SEQ ID NO: 1, causing a glycine to arginine change at residue 857 in SEQ ID NO: 2;
(3) a missense mutation at nucleotide 3141 of SEQ ID NO: 1, causing an arginine to proline change at residue 1041 in SEQ ID NO: 2;
(4) a missense mutation at nucleotide 3150 in SEQ ID NO: 1, causing a leucine to proline change at residue 1044 in SEQ ID NO: 2; and
(5) a missense mutation at nucleotide 3164 of SEQ ID NO: 1, causing an aspartic acid to asparagine change at residue 1049 in SEQ ID NO: 2.

For example, the invention provides oligonucleotides comprising anywhere from 6 to 50 nucleotides that have a sequence that is identical to, or exactly complementary to, a portion of the human VEGFR-3 coding sequence set forth in SEQ ID NO: 1, except for a nucleotide substitution corresponding to nucleotide 3360 of SEQ ID NO: 1. Such oligonucleotides may be generically described by the formula $X_n Y Z_m$ or its complement; where n and m are integers from 0 to 49; where $5 \leq (n+m) \leq 49$; where $X_n$ is a stretch of n nucleotides identical to a first portion of SEQ ID NO: 1 and $Z_m$ is a stretch of m nucleotides identical to a second portion of SEQ ID NO: 1, wherein the first and second portions are separated in SEQ ID NO: 1 by one nucleotide; and wherein Y represents a nucleotide other than the nucleotide that separates the first and second portions of SEQ ID NO: 1. For example, where $X_n$, represents 0 to 49 nucleotides immediately upstream (5') of nucleotide 3360 of SEQ ID NO: 1 and $Z_m$ represents 0 to 49 nucleotides immediately downstream (3') of nucleotide 3360 of SEQ ID NO: 1, Y represents a nucleotide other than cytosine, since a cytosine nucleotide is found at position 3360 of SEQ ID NO: 1. In a preferred embodiment, Y is a thymine nucleotide. Similar examples are contemplated for the other specific mutations identified immediately above.

In a related embodiment, the invention provides a kit comprising at least two such oligonucleotide probes. Preferably, the two or more probes are provided in separate containers, or attached to separate solid supports, or attached separately to the same solid support, e.g., on a DNA microchip.

In still another related embodiment, the invention provides an array of oligonucleotide probes immobilized on a solid support, the array having at least 4 probes, preferably at least 100 probes, and preferably up to 100,000, 10,000, or 1000 probes, wherein each probe occupies a separate known site in the array. In a preferred embodiment, the array includes probe sets comprising two to four probes, wherein one probe is exactly identical or exactly complementary to a human VEGFR-3 coding sequence, and the other one to three members of the set are exactly identical to the first member, but for at least one different nucleotide, which different nucleotide is located in the same position in each of the one to three additional set members. In one preferred embodiment, the array comprises several such sets of probes, wherein the sets correspond to different segments of the human VEGFR-3 gene sequence. In a highly preferred embodiment, the array comprises enough sets of oligonucleotides of length N to correspond to every particular N-mer sequence of the VEGFR-3 gene, where N is preferably 6 to 25 and more preferably 9 to 20. Materials and methods for making such probes are known in the art and are described, for example, in U.S. Pat. Nos. 5,837,832, 5,202,231, 5,002,867, and 5,143,854.

Moreover, the discoveries which underlie the present invention identify a target for therapeutic intervention in cases of hereditary lymphedema. The causative mutations in the families that have been studied in greatest detail are mutations that appear to result in VEGFR-3 signaling that is reduced in heterozygous affected individuals, but not completely eliminated. This data supports a therapeutic indication for administration of agents, such as VEGFR-3 ligand polypeptides, that will induce VEGFR-3 signaling in the lymphatic endothelia of affected individuals to effect improvement in the structure and function of the lymphatic vasculature of such individuals. In addition, therapeutic gene therapy, to replace defective VEGFR-3 alleles or increase production of VEGFR-3 ligand polypeptides in vivo, is envisioned as an aspect of the invention.

Thus, in yet another aspect, the invention provides a therapeutic or prophylactic method of treatment for lymphedema, comprising the step of administering to a mammalian subject in need of therapeutic or prophylactic treatment for lymphedema a composition comprising a compound effective to induce intracellular signaling of VEGFR-3 in lymphatic endothelial cells that express said receptor. In a preferred embodiment, the compound comprises a polypeptide ligand for VEGFR-3, or a polynucleotide encoding such a ligand, wherein the polynucleotide is administered in a form that results in transcription and translation of the polynucleotide in the mammalian subject to produce the ligand in vivo. In another preferred embodiment, the compound comprises any small molecule that is capable of binding to the VEGFR-3 receptor extracellular or intracellular domain and inducing intracellular signaling.

For example, the invention provides a therapeutic or prophylactic method of treatment for lymphedema, comprising the step of administering to a mammalian subject in need of therapeutic or prophylactic treatment for lymphedema a composition comprising a polynucleotide, the polynucleotide comprising a nucleotide sequence that encodes a vascular endothelial growth factor C (VEGF-C) polypeptide. In a preferred embodiment, the subject is a human subject.

While it is contemplated that the VEGF-C polynucleotide could be administered purely as a prophylactic treatment to prevent lymphedema in subjects at risk for developing lymphedema, it is contemplated in a preferred embodiment that the polynucleotide be administered to subjects afflicted with lymphedema, for the purpose of ameliorating its symptoms (e.g., swelling due to the accumulation of lymph). The polynucleotide is included in the composition in an amount and in a form effective to promote expression of a VEGF-C polypeptide in or near the lymphatic endothelia of the mammalian subject, to stimulate VEGFR-3 signaling in the lymphatic endothelia of the subject.

In a preferred embodiment, the mammalian subject is a human subject. Practice of methods of the invention in other mammalian subjects, especially mammals that are conventionally used as models for demonstrating therapeutic efficacy in humans (e.g., primate, porcine, canine, equine, murine, or rabbit animals), also is contemplated. Several potential animal models for hereditary lymphedema have been described in the literature. [See, e.g., Lyon et al., *Mouse News Lett.* 71: 26 (1984), *Mouse News Lett.* 74: 96 (1986), and *Genetic variants and strains of the laboratory mouse*, 2nd ed., New York: Oxford University Press (1989), p. 70 (*Chylous ascites* mouse); Dumont et al., *Science,* 282: 946-949 (1998) (heterozygous VEGFR-3 knockout mouse); Patterson et al., "Hereditary Lymphedema," *Comparative Pathology Bulletin,* 3: 2 (1971) (canine hereditary lymphedema model); van der Putte, "Congenital Hereditary Lymphedema in the Pig," *Lympho,* 11: 1-9 (1978); and Campbell-Beggs et al., "Chyloabdomen in a neonatal foal," *Veterinary Record,* 137: 96-98 (1995).] Those models which are determined to have analogous mutations to the VEGFR-3 gene, such as the *Chylous ascetei* (Chy) mouse, are preferred. The present inventors have analyzed the VEGFR-3 genes of the Chy mouse and determined that affected mice contain a missense mutation that results in a phenylalanine (rather than an isoleucine) in the VEGFR-3 sequence at a position corresponding to the isoleucine at position 1053 of SEQ ID NO: 2. This mutation maps to the catalytic pocket region of the tyrosine kinase domain of the VEGFR-3 protein, and may represent a viable model for identical mutations in human (if discovered) or other mutations in humans that similarly affect the tyrosine kinase catalytic domain. The Chy mouse has peripheral swelling (oedema) after birth and chyle ascites. In another embodiment, "knock in" homologous recombination genetic engineering strategies are used to create an animal model (e.g., a mouse model) having a VEGFR-3 allelic variation analogous to the human variations described herein. [See, e.g., Partanen et al., *Genes & Development,* 12: 2332-2344 (1998) (gene targeting to introduce mutations into a receptor protein (FGFR-1) in mice).] Such mice can also be bread to the heterozygous VEGFR-3 knockout mice or Chy mice described above to further modify the phenotypic severity of the lymphedema disease.

For the practice of methods of the invention, the term "VEGF-C polypeptide" is intended to include any polypeptide that has a VEGF-C or VEGF-C analog amino acid sequence (as defined elsewhere herein in greater detail) and that is able to bind the VEGFR-3 extracellular domain and stimulate VEGFR-3 signaling in vivo. The term "VEGF-C polynucleotide" is intended to include any polynucleotide (e.g., DNA or RNA, single- or double-stranded) comprising a nucleotide sequence that encodes a VEGF-C polypeptide. Due to the well-known degeneracy of the genetic code, multiple VEGF-C polynucleotide sequences exist that encode any selected VEGF-C polypeptide. Preferred VEGF-C polynucleotides, polypeptides, and VEGF-C variants and analogs for use in this invention are disclosed in International Patent Application No. PCT/US98/01973, published as WO 98/33917, incorporated herein by reference in its entirety.

For treatment of humans, VEGF-C polypeptides with an amino acid sequence of a human VEGF-C are highly preferred, and polynucleotides comprising a nucleotide sequence of a human VEGF-C cDNA are highly preferred. By "human VEGF-C" is meant a polypeptide corresponding to a naturally occurring protein (prepro-protein, partially-processed protein, or fully-processed mature protein) encoded by any allele of the human VEGF-C gene, or a polypeptide comprising a biologically active fragment of a naturally-occurring mature protein. By way of example, a human VEGF-C comprises a continuous portion of the amino acid sequence set forth in SEQ ID NO: 4 sufficient to permit the polypeptide to bind and stimulate VEGFR-3 phosphorylation in cells that express such receptors. A polypeptide comprising amino acids 131-211 of SEQ ID NO: 4 is specifically contemplated. For example, polypeptides having an amino acid sequence comprising a continuous portion of SEQ ID NO: 4, the continuous portion having, as its amino terminus, an amino acid selected from the group consisting of positions 30-131 of SEQ ID NO: 4, and having, as its carboxyl terminus, an amino acid selected from the group consisting of positions 211-419 of SEQ ID NO: 4 are contemplated. An amino terminus selected from the group consisting of positions 102-131 of SEQ ID NO: 4 is preferred, and an amino terminus selected from the group consisting of positions 103-113 of SEQ ID NO: 4 is highly preferred. Likewise, a carboxyl terminus selected from the group consisting of positions 211-227 of SEQ ID NO: 4 is preferred. As stated above, the term "human VEGF-C" also is intended to encompass polypeptides encoded by allelic variants of the human VEGF-C characterized by the sequences set forth in SEQ ID NOs: 3 & 4.

Moreover, since the therapeutic VEGF-C is to be administered as recombinant VEGF-C or indirectly via somatic gene therapy, it is within the skill in the art to make and use analogs of human VEGF-C (and polynucleotides that encode such analogs) wherein one or more amino acids have been added, deleted, or replaced with other amino acids, especially with conservative replacements, and wherein the VEGFR-3-stimulatory biological activity has been retained. Analogs that retain VEGFR-3-stimulatory VEGF-C biological activity are contemplated as VEGF-C polypeptides for use in the present invention. In a preferred embodiment, analogs having 1, 2, 3, 4, 5, 6, 7, 8, 9, 10, 11, 12, 13, 14, 15, 16, 17, 18, 19, 20, 21, 22, 23, 24, or 25 such modifications and that retain VEGFR-3-stimulatory VEGF-C biological activity are contemplated as VEGF-C polypeptides for use in the present invention. Analogs having a deletion of or substitution for the cysteine residue at position 156 of SEQ ID NO: 4 and that retain VEGFR-3 stimulatory activity, but have reduced activity toward the receptor VEGFR-2, which is expressed in blood vessels, are specifically contemplated. See. WO 98/33917. Polynucleotides encoding such analogs are generated using conventional PCR, site-directed mutagenesis, and chemical synthesis techniques.

Also contemplated as VEGF-C polypeptides are non-human mammalian or avian VEGF-C polypeptides and polynucleotides. By "mammalian VEGF-C" is meant a polypeptide corresponding to a naturally occurring protein (preproprotein, partially-processed protein, or fully-processed mature protein) encoded by any allele of a VEGF-C gene of any mammal, or a polypeptide comprising a biologically active fragment of a mature protein. The term "mammalian VEGF-C polypeptide" is intended to include analogs of mammalian VEGF-C's that possess the in vivo VEGFR-3-stimulatory effects of the mammalian VEGF-C.

Irrespective of which encoded VEGF-C polypeptide is chosen, any VEGF-C polynucleotide gene therapy pharmaceutical encoding it preferably comprises a nucleotide sequence encoding a secretory signal peptide fused in-frame with the VEGF-C polypeptide sequence. The secretory signal peptide directs secretion of the VEGF-C polypeptide by the cells that express the polynucleotide, and is cleaved by the cell from the secreted VEGF-C polypeptide. For example, the VEGF-C polynucleotide could encode the complete prepro-VEGF-C sequence set forth in SEQ ID NO: 4; or could encode the VEGF-C signal peptide fused in-frame to a sequence encoding a fully-processed VEGF-C (e.g., amino acids 103-227 of SEQ ID NO: 4) or VEGF-C analog. Moreover, there is no requirement that the signal peptide be derived from VEGF-C. The signal peptide sequence can be that of another secreted protein, or can be a completely synthetic signal sequence effective to direct secretion in cells of the mammalian subject.

In one embodiment, the VEGF-C polynucleotide of the invention comprises a nucleotide sequence that will hybridize to a polynucleotide that is complementary to the human VEGF-C cDNA sequence specified in SEQ ID NO: 3 under the following exemplary stringent hybridization conditions: hybridization at 42° C. in 50% formamide, 5×SSC, 20 mM NaP O$_4$, pH 6.8; and washing in 1×SSC at 55° C. for 30 minutes; and wherein the nucleotide sequence encodes a polypeptide that binds and stimulates human VEGFR-3. It is understood that variation in these exemplary conditions occur based on the length and GC nucleotide content of the sequences to be hybridized. Formulas standard in the art are appropriate for determining appropriate hybridization conditions. [See Sambrook et al., *Molecular Cloning: A Laboratory Manual* (Second ed., Cold Spring Harbor, N.Y.: Cold Spring Harbor Laboratory Press, 1989) §§9.47-9.51.]

In preferred embodiments, the VEGF-C polynucleotide further comprises additional sequences to facilitate the VEGF-C gene therapy. In one embodiment, a "naked" VEGF-C transgene (i.e., a transgene without a viral, liposomal, or other vector to facilitate transfection) is employed for gene therapy. In this embodiment, the VEGF-C polynucleotide preferably comprises a suitable promoter and/or enhancer sequence (e.g., cytomegalovirus promoter/enhancer [Lehner et al., *J. Clin. Microbiol.*, 29:2494-2502 (1991); Boshart et al., *Cell*, 41:521-530 (1985)]; Rous sarcoma virus promoter [Davis et al., *Hum. Gene Ther.*, 4:151 (1993)]; Tie promoter [Korhonen et al., *Blood*, 86(5): 1828-1835 (1995)]; or simian virus 40 promoter) for expression in the target mammalian cells, the promoter being operatively linked upstream (i.e., 5') of the VEGF-C coding sequence. The VEGF-C polynucleotide also preferably further includes a suitable polyadenylation sequence (e.g., the SV40 or human growth hormone gene polyadenylation sequence) operably linked downstream (i.e., 3') of the VEGF-C coding sequence. The polynucleotide may further optionally comprise sequences whose only intended function is to facilitate large-scale production of the vector, e.g., in bacteria, such as a bacterial origin of replication and a sequence encoding a selectable marker. However, in a preferred embodiment, such extraneous sequences are at least partially cleaved off prior to administration to humans according to methods of the invention. One can manufacture and administer such polynucleotides to achieve successful gene therapy using procedures that have been described in the literature for other transgenes. See, e.g., Isner et al., *Circulation*, 91: 2687-2692 (1995); and Isner et al., *Human Gene Therapy*, 7: 989-1011 (1996); incorporated herein by reference in the entirety.

Any suitable vector may be used to introduce the VEGF-C transgene into the host. Exemplary vectors that have been described in the literature include replication-deficient retroviral vectors, including but not limited to lentivirus vectors [Kim et al., *J. Virol.*, 72(1): 811-816 (1998); Kingsman & Johnson, *Scrip Magazine*, October, 1998, pp. 43-46.]; adeno-associated viral vectors [Gnatenko et al., *J. Investig. Med.*, 45: 87-98 (1997)]; adenoviral vectors [See, e.g., U.S. Pat. No. 5,792,453; Quantin et al., *Proc. Natl. Acad. Sci. USA*, 89: 2581-2584 (1992); Stratford-Perricadet et al., *J. Clin. Invest.*, 90: 626-630 (1992); and Rosenfeld et al., *Cell*, 68: 143-155 (1992)]; Lipofectin-mediated gene transfer (BRL); liposomal vectors [See, e.g., U.S. Pat. No. 5,631,237 (Liposomes comprising Sendai virus proteins)]; and combinations thereof. All of the foregoing documents are incorporated herein by reference in the entirety. Replication-deficient adenoviral vectors constitute a preferred embodiment.

In embodiments employing a viral vector, preferred polynucleotides still include a suitable promoter and polyadenylation sequence as described above. Moreover, it will be readily apparent that, in these embodiments, the polynucleotide further includes vector polynucleotide sequences (e.g., adenoviral polynucleotide sequences) operably connected to the sequence encoding a VEGF-C polypeptide.

Thus, in one embodiment the composition to be administered comprises a vector, wherein the vector comprises the VEGF-C polynucleotide. In a preferred embodiment, the vector is an adenovirus vector. In a highly preferred embodiment, the adenovirus vector is replication-deficient, i.e., it cannot replicate in the mammalian subject due to deletion of essential viral-replication sequences from the adenoviral genome. For example, the inventors contemplate a method wherein the vector comprises a replication-deficient adenovirus, the adenovirus comprising the VEGF-C polynucleotide operably connected to a promoter and flanked on either end by adenoviral polynucleotide sequences.

The composition to be administered according to methods of the invention preferably comprises (in addition to the polynucleotide or vector) a pharmaceutically-acceptable carrier solution such as water, saline, phosphate-buffered saline, glucose, or other carriers conventionally used to deliver therapeutics intravascularly. Multi-gene therapy is also contemplated, in which case the composition optionally comprises both the VEGF-C polynucleotide/vector and another polynucleotide/vector. As described in greater detail below, a VEGF-D transgene is a preferred candidate for co-administration with the VEGF-C transgene.

The "administering" that is performed according to the present method may be performed using any medically-accepted means for introducing a therapeutic directly or indirectly into a mammalian subject to reach the lymph or the lymphatic system, including but not limited to injections; oral ingestion; intranasal or topical administration; and the like. In a preferred embodiment, administration of the composition comprising the VEGF-C polynucleotide is performed intravascularly, such as by intravenous or intra-arterial injection, or by subcutaneous injection or local depot administration. In a highly preferred embodiment, the composition is administered locally, e.g., to the site of swelling.

In still another variation, endothelial cells or endothelial progenitor cells are transfected ex vivo with a wild type VEGFR-3 transgenc, and the transfected cells are administered to the mammalian subject.

In another aspect, the invention provides a therapeutic or prophylactic method of treating for lymphedema, comprising the step of administering to a mammalian subject in need of treatment for lymphedema a composition comprising a VEGF-C polypeptide, in an amount effective to treat or prevent swelling associated with lymphedema. Administration via one or more intravenous or subcutaneous injections is contemplated. Co-administration of VEGF-C polynucleotides and VEGF-C polypeptides is also contemplated.

In yet another embodiment, the invention provides the use of a VEGF-C polynucleotide or VEGF-C polypeptide for the manufacture of a medicament for the treatment or prevention of lymphedema.

In still another embodiment, the invention provides a therapeutic or prophylactic method of treatment for lymphedema, comprising the step of administering to a mammalian subject in need of therapeutic or prophylactic treatment of lymphedema a composition comprising a polynucleotide, the polynucleotide comprising a nucleotide sequence that encodes a vascular endothelial growth factor D (VEGF-D) polypeptide. Such methods are practiced essentially as described herein with respect to VEGF-C-encoding polynucleotides, except that polynucleotides encoding VEGF-D are employed. A detailed description of the human VEGF-D gene and protein are provided in Achen, et al., Proc. Nat'l Acad. Sci. U.S.A., 95(2): 548-553 (1998); International Patent Publication No. WO 98/07832, published 26 Feb. 1998; and in Genbank Accession No. AJ000185, all incorporated herein by reference. A cDNA and deduced amino acid sequence for prepro-VEGF-D is set forth herein in SEQ ID NOs: 5 and 6. Of course, due to the well-known degeneracy of the genetic code, multiple VEGF-D encoding polynucleotide sequence exist, any of which may be employed according to the methods taught herein.

As described herein in detail with respect to VEGF-C, the use of polynucleotides that encode VEGF-D fragments, VEGF-D analogs, VEGF-D allelic and interspecies variants, and the like which possess in vivo stimulatory effects of human VEGF-D are all contemplated as being encompassed by the present invention.

In one aspect, described herein is an isolated and purified nucleic acid molecule which encodes a novel polypeptide, designated VEGF-D, which is structurally homologous to VEGF, VEGF-B and VEGF-C. In a preferred embodiment, the nucleic acid molecule is a cDNA which comprises the sequence set out in SEQ ID NO: 5. This aspect also encompasses DNA molecules of sequence such that the hybridize under stringent conditions with DNA of SEQ ID NO: 5. Preferably the DNA molecule able to hybridize under stringent conditions encodes the portion of VEGF-D from amino acid residue 93 to amino acid residue 201, optionally operatively linked to a DNA sequence encoding a FLAG™ peptide.

In one aspect, described herein is a purified and isolated nucleic acid encoding a polypeptide or polypeptide fragment described herein. The nucleic acid may be DNA, genomic DNA, cDNA or RNA, and may be single-stranded or double-stranded. The nucleic acid may be isolated from a cell or tissue source, or of recombinant or synthetic origin. Because of the degeneracy of the genetic code, the person skilled in the art will appreciate that many such coding sequences are possible, where each sequence encodes the amino acid sequence shown in SEQ ID NO: 6, an active fragment or analog thereof, or a receptor-binding but otherwise inactive or partially active variant thereof.

In another aspect, described herein are vectors comprising a VEGF-D cDNA or a VEGF-D nucleic acid as described herein, and host cells transformed or transfected with nucleic acids or vectors. These cells are particularly suitable for expression of the VEGF-D polypeptide, and include insect cells such as Sf9 cells, obtainable from the American Type Culture Collection (ATCC SRL-171), transformed with a baculovirus vector, and the human embryo kidney cell line 293EBNA transfected by a suitable expression plasmid. Preferred vectors are expression vectors in which a nucleic acid described herein is operatively connected to one or more appropriate promoters and/or other control sequences, such that appropriate host cells transformed or transfected with the vectors are capable of expression the VEGF-D polypeptide. Other preferred vectors are those suitable for transfection of mammalian cells, or for gene therapy, such as adenovirus or retrovirus vectors or liposomes. A variety of such vectors are known in the art.

Also described herein is a method of making a vector capable of expression a polypeptide encoded by a nucleic acid described herein, comprising the steps of operatively connecting to the nucleic acid one or more appropriate promoters and/or other control sequences, as described above.

In one aspect, the VEGF-D polypeptide possesses the characteristic amino acid sequence:

Pro-Xaa-Cys-Val-Xaa-Xaa-Xaa-Arg-Cys-Xaa-Gly-Cys-Cys (SEQ ID NO. 29), said polypeptide having the ability to stimulate proliferation of endothelial cells, and said polypeptide comprising a sequence of amino acids substantially corresponding to the amino acid sequence set out in SEQ ID NO. 6, or a fragment or analogue thereof which has the ability to stimulate one or more of endothelial cell proliferation, differentiation, migration or survival. These abilities are referred to herein as "biological activities of VEGF-D" and can readily be tested by methods known in the art. Preferably the polypeptide has the ability to stimulate endothelial cell proliferation or differentiation, including, but not limited to, proliferation or differentiation of vascular endothelial cells and/or lymphatic endothelial cells. More preferably the polypeptide has the sequence set out in SEQ ID NO: 6.

The deduced amino acid sequence for VEGF-D includes a central region which is similar in sequence to all other members of the VEGF family (approximately residues 101 to 196 of the human VEGF-D amino acid sequence (SEQ ID NO: 6) as shown in the alignment in FIG. 5. It was predicted that the mature VEGF-D sequence would be derived from a fragment contained within residues 92-205, with cleavage at FAA^TFY (amino acids 89-94 of SEQ ID NO: 6) and IIRR^SIQI (amino acids 202-209 of SEQ ID NO: 6). Immunoprecipitation analysis of VEGF-DfullFLAG expressed in COS cells produced species consistent with the internal proteolytic cleavage of the VEGF-D polypeptide at these sites.

VEGF-D polypeptides comprising conservative substitutions, insertions, or deletions, but which still retain the biological activity of VEGF-D, are clearly to be understood to be within the scope of the invention. The person skilled in the art will be well aware of methods which can readily be used to generate such polypeptides, for example the use of site-directed mutagenesis or specific enzymic cleavage and ligation. The skilled person will also be aware that pepticlomimetic compounds or compounds in which one or more amino acid residues are replaced by a non-naturally occurring amino acid or an amino acid analogue may retain the required aspects of the biological activity of VEGF-D. Such compounds can readily be made and tested by methods known in the art, and are also within the scope of the invention.

In addition, variant forms of the VEGF-D polypeptide which result from alternative splicing, as are known to occur with VEGF, and naturally-occurring allelic variants of the nucleic acid sequence encoding VEGF-D are encompassed within the scope of the invention. Allelic variants are well known in the art, and represent alternative forms or a nucleic acid sequence which comprise substitution, deletion or addition of one or more nucleotides, but which do not result in any substantial functional alteration of the encoded polypeptide.

Such variant forms of VEGF-D can be prepared by targeting non-essential regions of the VEGF-D polypeptide for modification. These non-essential regions are expected to fall outside the strongly-conserved regions indicated in the FIG. 4 and FIG. 5. In particular, the growth factors of the PDGF family, including VEGF, are dimeric, and VEGF-B, VEGF-C, P1GF, PDGF-A and PDGF-B show complete conservation of 8 cysteine residues in the N-terminal domains, ie. the PDGF-like domains (Olofsson et al, 1996: Joukov et al, 1996). These cysteines are thought to be involved in intra- and inter-molecular disulphide bonding. In addition there are further strongly, but not completely, conserved cysteine residues in the C-terminal domains. Loops 1, 2 and 3 of each subunit, which are formed by intra-molecular disulphide bonding. are involved in binding to the receptors for the PDGF/VEGF family of growth factors (Andersson et al : Growth Factors, 1995 .12. 159-164). As shown herein, the cysteines conserved in previously known members of the VEGF family are also conserved in VEGF-D.

The person skilled in the art thus is well aware that these cysteine residues should be preserved in any proposed variant form, and that the active sites present in loops 1, 2 and 3 also should be preserved. However, other regions of the molecule can be expected to be of lesser importance for biological function, and therefore offer suitable targets for modification. Modified polypeptides can readily be tested for their ability to show the biological activity of VEGF-D by routine activity assay procedures such as cell proliferation tests.

Construction of VEGF-D Variants and Analogues

VEGF-D is a member of the PDGF family of growth factors which exhibits a high degree of homology to the other members of the PDGF family. VEGF-D contains eight conserved cysteine residues which are characteristic of this family of growth factors. These conserved cysteine residues form intra-chain disulfide bonds which produce the cysteine knot structure, and inter-chain disulfide bonds that form the protein dimers which are characteristic of members of the PDGF family of growth factors. VEGF-D will interact with protein tyrosine kinase growth factor receptors.

In contrast to proteins where little or nothing is known about the protein structure and active sites needed for receptor binding and consequent activity, the design of active mutants of VEGF-D is greatly facilitated by the fact that a great deal is known about the active sites and important amino acids of the members of the PDGF family of growth factor. Published articles elucidating the structure/activity relationships of members of the PDGF family of growth factors include for PDGF: Oestman et al, J. Biol. Chem., 1991 266 10073-10077; Andersson et al, J. Biol. Chem., 1992 267 11260-1266; Oefner et al, EMBO J., 1992 1 3921-3926; Flemming et al, Molecular and Cell Biol., 1993 11 4066-4076 and Andersson et al, Growth Factors, 1995 12. 159-164; and for VEGF: Kim et al, Growth Factors, 1992 1 53-64; Pδtgens et al, J. Biol. Chem., 1994 269 32879-32885 and Claffey et al, Biochem. Biophys. Acta, 1995 1246 1-9. From these publications it is apparent that because of the eight conserved cysteine residues, the members of the PDGF family of growth factors exhibit a characteristic knotted folding structure and dimerization, which result in formation of three exposed loop regions at each end of the dimerized molecule, at which the active receptor binding sites can be expected to be located. Based on this information, a person skilled in the biotechnology arts can design VEGF-D mutants with a very high probability of retaining VEGF-D activity by conserving the eight cysteine residues responsible for the knotted folding arrangement and for dimerization, and also by conserving, or making only conservative amino acid substitutions in the likely receptor sequences in the loop 1, loop 2 and loop 3 region of the protein structure. The formation of desired mutations at specifically targeted sites in a protein structure is considered to be a standard technique in the arsenal of the protein chemist (Kunkel et al, Methods in Enzymol., 1987 154 367-382). Examples of such site-directed mutagenesis with VEGF can be found in Pδtgens et al, J. Biol. Chem., 1994 269 32879-32885 and Claffey et al, Biochim. Biophys. Acta, 1995 1246 1-9. Indeed, site-directed mutagenesis is so common that kits are commercially available to facilitate such procedures (eg. Promega 1994-1995 Catalog., Pages 142-145).

The endothelial cell proliferating activity of VEGF-D mutants can be readily confirmed by well established screening procedures. For example, a procedure analogous to the endothelial cell mitotic assay described by Claffey et al, (Biochim. Biophys. Acta., 1995 1246 1-9) can be used. Similarly the effects of VEGF-D on proliferation of other cell types, on cellular differentiation and on human metastasis can be tested using methods which are well known in the art.

In yet another embodiment, the invention provides a therapeutic or prophylactic method of treatment for lymphedema, comprising the step of administering to a mammalian subject in need of treatment for lymphedema a composition comprising a VEGF-D polypeptide, in an amount effective to treat or prevent swelling associated with lymphedema. Administration via one or more intravenous or subcutaneous injections is contemplated.

The VEGFR-3 allelic variant polynucleotides and polypeptides described herein that were discovered and characterized by the present inventors are themselves considered aspects of the invention. Such polynucleotides and polypeptides are useful, for example, in screening assays (e.g., cell-based assays or assays involving transgenic mice that express the polynucleotide in lieu of a native VEGF-3 allele) to study the biological activities of VEGFR-3 variant alleles and identify compounds that are capable of modulating that activity, e.g., to identify therapeutic candidates for treatment of lymphedema. Such screening assays are also considered aspects of the invention.

The polypeptides of the invention are intended to include complete VEGFR-3 polypeptides with signal peptide (e.g., approximately residues 1 to 20 of SEQ ID NO: 2), mature VEGFR-3 polypeptides lacking any signal peptide, and recombinant variants wherein a foreign or synthetic signal peptide has been fused to the mature VEGFR-3 polypeptide. Polynucleotides of the invention include all polynucleotides that encode all such polypeptides. It will be understood that for essentially any polypeptide, many polynucleotides can be constructed that encode the polypeptide by virtue of the well known degeneracy of the genetic code. All such polynucleotides are intended as aspects of the invention.

Thus, in yet another aspect, the invention provides a purified polynucleotide comprising a nucleotide sequence encoding a human VEGFR-3 protein variant, wherein said polynucleotide is capable of hybridizing to the complement of SEQ ID NO: 1 under stringent hybridization conditions, and wherein the encoded VEGFR-3 protein variant has an amino acid sequence that differs at position 1114, 857, 1041, 1044 or 1049 from the amino acid sequence set forth in SEQ ID NO: 1. Exemplary conditions are as follows: hybridization at 42° C. in 50% formamide, 5×SSC, 20 mM NaIP O4, pH 6.8; and washing in 0.2×SSC at 55° C. It is understood by those of skill in the art that variation in these conditions occurs based on the length and GC nucleotide content of the sequences to be hybridized. Formulas standard in the art are appropriate for determining appropriate hybridization conditions. [See Sambrook et al. (1989), supra, §§9.47-9.51.]

In a related embodiment, the invention provides a purified polynucleotide comprising a nucleotide sequence encoding a VEGFR-3 protein of a human that is affected with heritable lymphedema or other lymphatic disorder; wherein the polynucleotide is capable of hybridizing to the complement of SEQ ID NO: 1 under stringent hybridization conditions, and wherein the encoded polynucleotide has an amino acid sequence that differs from SEQ ID NO: 1 at least one codon. It will be understood that conventional recombinant techniques can be used to isolate such polynucleotides from individuals affected with heritable lymphedema or their relatives. The wildtype VEGFR-3 cDNA sequence set forth in SEQ ID NO: 1 (or its complement, or fragments thereof) is used as a probe to identify and isolate VEGFR-3 sequences from nucleic acid derived from the individuals. Alternatively, PCR amplification primers based on the wildtype VEGFR-3 sequence are generated and used to amplify either VEGFR-3 genomic DNA or VEGFR-3 mRNA from the human subject. The resultant amplified genomic DNA or cDNA is sequenced to determine the variations that characterize the VEGFR-3 lymphedema allele of the individual. Preferred VEGFR-3 lymphedema alleles include, but are not limited to the P1114L, G857R, R1041P, L1044P and D1049N alleles described in detail herein.

In addition, the invention provides vectors that comprise the polynucleotides of the invention. Such vectors are useful for amplifying and expressing the VEGFR-3 proteins encoded by the polynucleotides, and for creating recombinant host cells and/or transgenic animals that express the polynucleotides. The invention further provides a host cell transformed or transfected with polynucleotides (including vectors) of the invention. In a preferred embodiment, the host cell expresses the encoded VEGFR-3 protein on its surface. Such host cells are useful in cell-based screening assays for identifying modulators that stimulate or inhibit signaling of the encoded VEGFR-3. Modulators that stimulate VEGFR-3 signaling have utility as therapeutics to treat lymphedemas, whereas modulators that are inhibitory have utility for treating hyperplastic lymphatic conditions mediated by the allelic variant VEGFR-3. In a preferred embodiment, host cells of the invention are co-transfected with both a wildtype and an allelic variant VEGFR-3 polynucleotide, such that the cells express both receptor types on their surface. Such host cells are preferred for simulating a heterozygous VEGFR-3 genotype of many individuals affected with lymphedema.

In yet another aspect, the invention provides a transgenic mammal, e.g., mouse, characterized by a non-native VEGFR-3 allele that has been introduced into the mouse, and the transgenic progeny thereof. Preferred allelic variants include allelic variants that correlate with hereditary lymphedema in human subjects, such as an allelic variant wherein a P1114L, G857R, R1041P, L1044P or D1049N missense mutation has been introduced into the murine VEGFR-3 gene, or wherein the human P1114L, G857R, R1041P, L1044P or D1049N allelic variant has been substituted for a murine VEGFR-3 allele. Such mice are produced using standard methods. [See, e.g., Hogan et al. (eds.), *Manipulating the Mouse Embryo*, Cold Spring Harbor, N.Y.: Cold Spring Harbor Laboratory (1986).] The introduction of the human-like mutations into non-human sequences is readily achieved with standard techniques, such as site-directed mutagenesis. The determination of which residues in a non-human sequence to alter to mimic the foregoing human mutations is routine since the foregoing mutations all occur in regions of the VEGFR-3 sequence that contain residues that are highly conserved between species. See FIGS. 3A-3B.

In yet another aspect, the invention provides assays for identifying modulators of VEGFR-3 signaling, particularly modulators of the signaling of allelic variants of VEGFR-3 that correlate with lymphatic disorders such as heritable lymphedema. For example, the invention provides a method for identifying a modulator of intracellular VEGFR-3 signaling, comprising the steps of: contacting a cell expressing at least one mutant mammalian VEGFR-3 polypeptide in the presence and in the absence of a putative modulator compound; b) detecting VEGFR-3 signaling in the cell; and c) identifying a putative modulator compound in view of decreased or increased signaling in the presence of the putative modulator, as compared to signaling in the absence of the putative modulator.

By "mutant mammalian VEGFR-3 polypeptide" is meant a VEGFR-3 polypeptide that varies from a wildtype mammalian VEGFR-3 polypeptide (e.g., by virtue of one or more amino acid additions, deletions, or substitutions), wherein the variation is reflective of a naturally occurring variation that has been correlated with a lymphatic disorder, such as lymphedema. By way of example, the previously described substitution variations of human VEGFR-3, such as P1114L, have been correlated with heritable lymphedema. Any of the human allelic variants described above, or analogous human allelic variants having a different substitution at the indicated amino acid positions, or a non-human VEGFR-3 into which a mutation at the position corresponding to any of the described positions has been introduced are all examples of mutant mammalian VEGFR-3 polypeptides.

The detecting step can entail the detection of any parameter indicative of VEGFR-3 signaling. For example, the detecting step can entail a measurement of VEGFR-3 autophosphorylation, or a measurement of VEGFR-3-mediated cell growth, or a measurement of any step in the VEGFR-3 signaling cascade between VEGFR-3 autophosphorylation and cell growth.

In a preferred embodiment, the method is practiced with a cell that expresses the mutant mammalian VEGFR-3 polypeptide and a wildtype mammalian VEGFR-3 polypeptide. Such cells are thought to better mimic the conditions in heterozygous individuals suffering from a VEGFR-3-mediated lymphatic disorder. In a highly preferred embodiment, the mutant and wildtype VEGFR-3 polypeptides are human. In the preferred embodiments, the mutant VEGFR-3 polypeptide comprises a leucine amino acid at the position corresponding to position 1114 of SEQ ID NO: 2; an arginine at the position corresponding to position 857 of SEQ ID NO: 2; a proline amino acid at the position corresponding to position 1041 of SEQ ID NO: 2; a proline amino acid at the position corresponding to position 1044 of SEQ ID NO: 2; or an asparagine at the position corresponding to position 1049 of SEQ ID NO: 2.

Additional features and variations of the invention will be apparent to those skilled in the art from the entirety of this application, including the drawing and detailed description, and all such features are intended as aspects of the invention. Likewise, features of the invention described herein can be re-combined into additional embodiments that are also intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 3A-3B depict an alignment of portions of the human (top line, SEQ ID NO: 2) and murine (bottom line, GenBank Acc. No. P35917, SEQ ID NO: 19) VEGFR-3 amino acid sequences to demonstrate similarity. Identical residues are marked with a line, and highly conserved and less conserved differences are marked with two dots or a single dot, respectively. The location of various mutations that have been observed to correlate with a heritable lymphedema phenotype are indicated immediately beneath the aligned sequences.

FIG. 4 shows sequence alignments between the sequences of human VEGF-D (SEQ ID NO: 6), human $VEGF_{165}$ (SEQ ID NO: 30), human VEGF-B (SEQ ID NO: 31), human VEGF-C (SEQ ID NO: 4) and human P1GF (SEQ ID NO: 32). The boxes indicate residues that match VEGF-D exactly.

FIG. 5 shows sequence alignments between the amino acid sequences of human VEGF-D (SEQ ID NO: 6), human $VEGF_{165}$, (SEQ ID NO: 30) human VEGF-B (SEQ ID NO: 31), human VEGF-C (SEQ ID NO: 4), and human P1GF (SEQ ID NO: 32).

DETAILED DESCRIPTION OF THE INVENTION

Figure 1A:
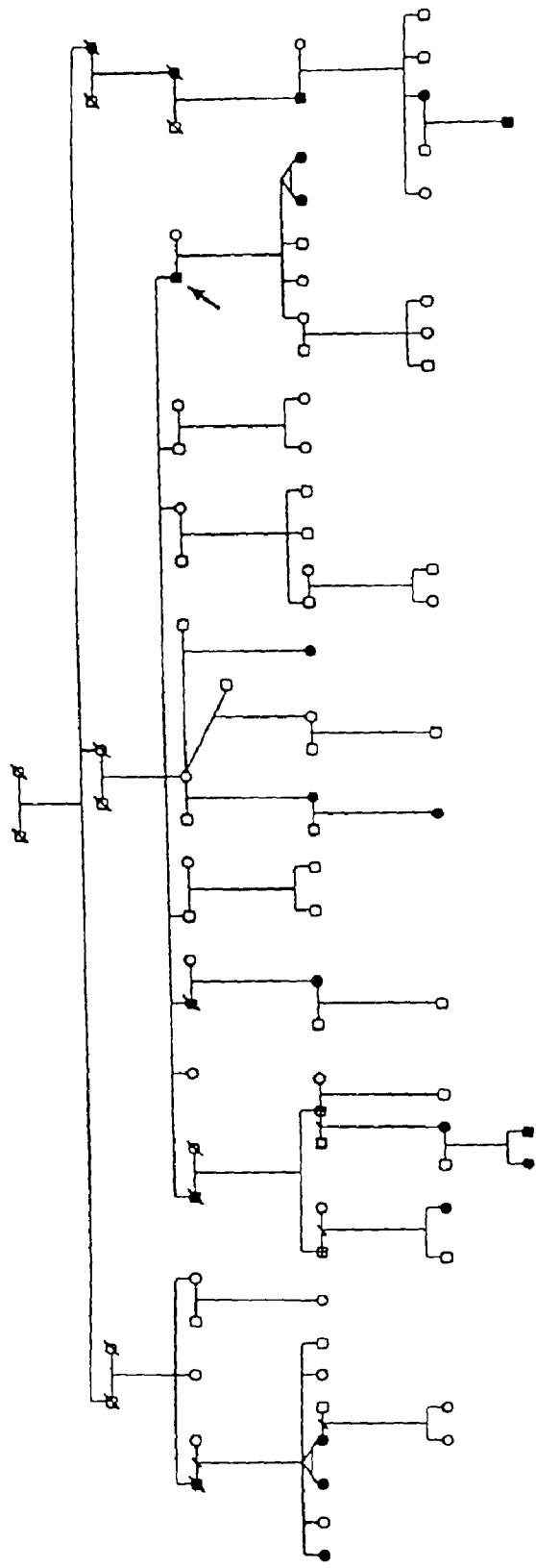
FIGS. 1A-1F depict pedigrees of six hereditary lymphedema families (Families 101, 106, 111, 135, 105, and 127, respectively) informative for linkage. Filled symbols represent individuals with clinically documented lymphedema. Crossed symbols represent individuals with an ambiguous phenotype. An ambiguous phenotype is defined as self-reported swelling of the limbs with no known cause, without a clinical diagnosis of lymphedema. Individuals of ambiguous phenotype were coded as disease status unknown for the linkage analysis. The proband in each family is indicated by an arrow.
Figure 1C:
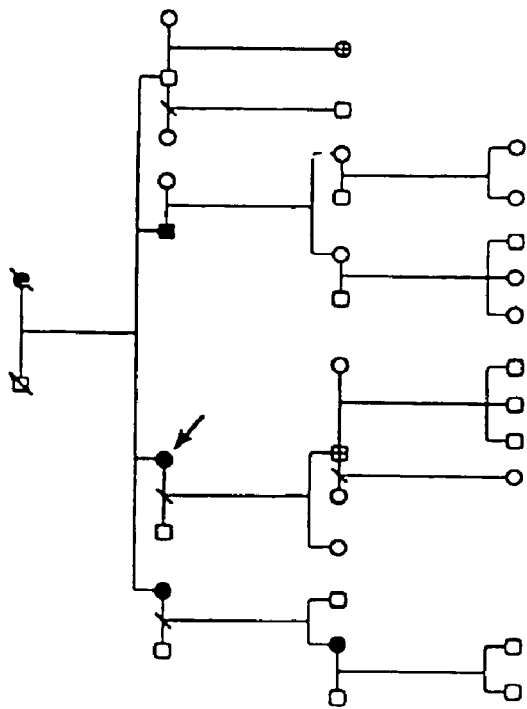
Figure 1B:
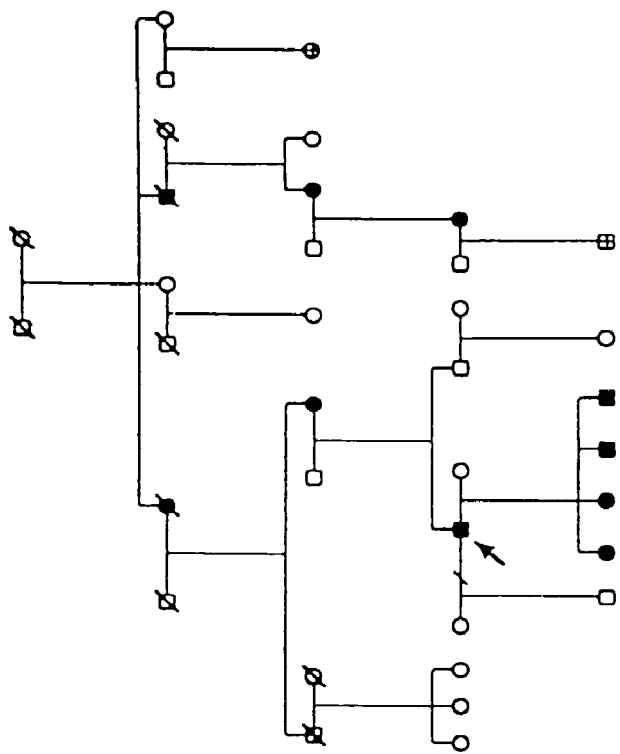
Figure 1E:
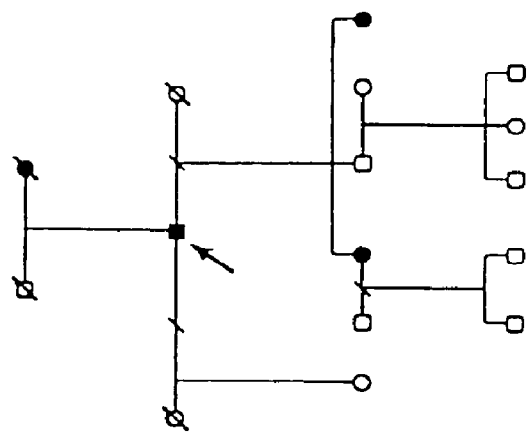
Figure 1D:
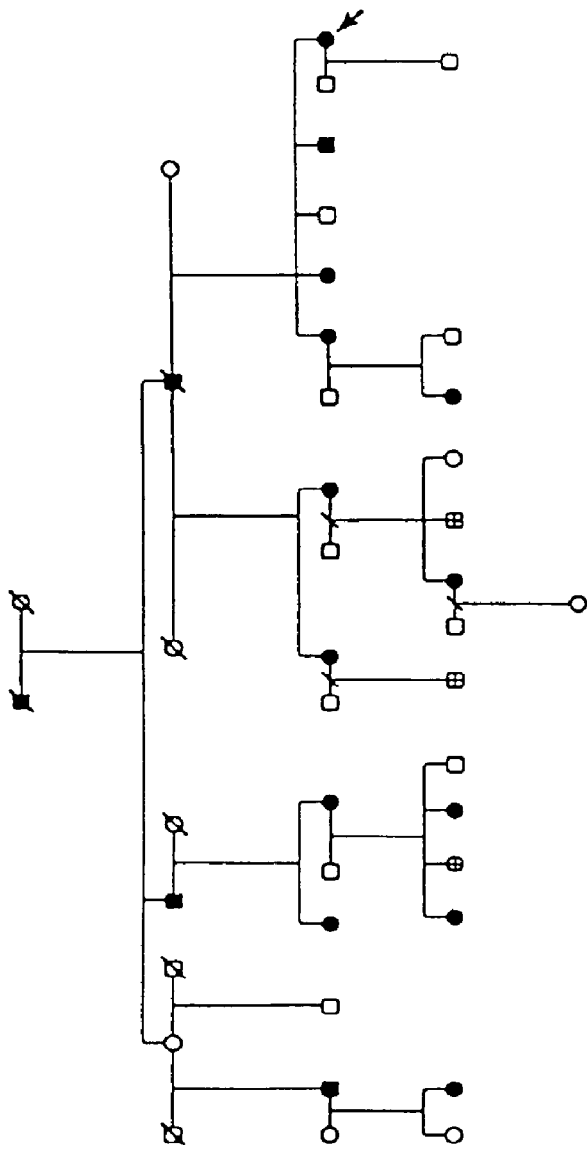
Figure 1F:
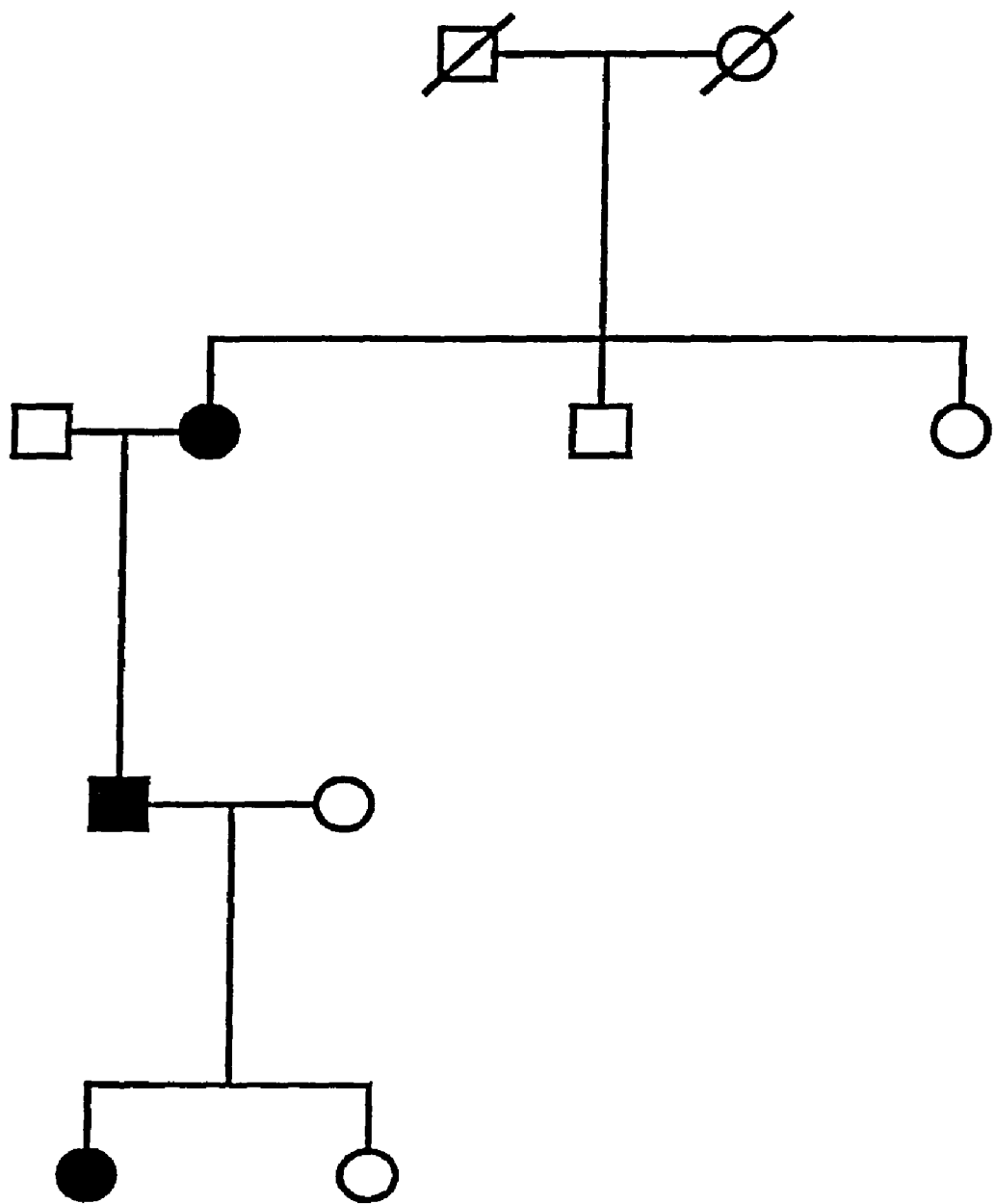

Certain therapeutic aspects of the present invention involve the administration of Vascular Endothelial Growth Factor C or D polynucleotides and polypeptides. The growth factor VEGF-C, as well as native human, non-human mammalian, and avian polynucleotide sequences encoding VEGF-C, and VEGF-C variants and analogs, have been described in detail in International Patent Application Number PCT/US98/01973, filed 2 Feb. 1998 and published on 6 Aug. 1998 as International Publication Number WO 98/33917; in Joukov et al., *J. Biol. Chem.*, 273(12): 6599-6602 (1998); and in Joukov et al., *EMBO J.*, 16(13): 3898-3911 (1997), all of which are incorporated herein by reference in the entirety. As explained therein in detail, human VEGF-C is initially produced in human cells as a prepro-VEGF-C polypeptide of 419 amino acids. A cDNA and deduced amino acid sequence for human prepro-VEGF-C are set forth in SEQ ID NOs: 3 and 4, respectively, and a cDNA encoding human VEGF-C has been deposited with the American Type Culture Collection (ATCC), 10801 University Blvd., Manassas, Va. 20110-2209 (USA), pursuant to the provisions of the Budapest Treaty (Deposit date of 24 Jul. 1995 and ATCC Accession Number 97231). VEGF-C sequences from other species have also been reported. See Genbank Accession Nos. MMU73620 (*Mus musculus*); and CCY15837 (*Coturnix coturnix*) for example, incorporated herein by reference.

The prepro-VEGF-C polypeptide is processed in multiple stages to produce a mature and most active VEGF-C polypeptide of about 21-23 kD (as assessed by SDS-PAGE under reducing conditions). Such processing includes cleavage of a signal peptide (SEQ ID NO: 4, residues 1-31); cleavage of a carboxyl-terminal peptide (corresponding approximately to amino acids 228-419 of SEQ ID NO: 4 and having a pattern of spaced cysteine residues reminiscent of a Balbiani ring 3 protein (BR3P) sequence [Dignam et al., Gene, 88:133-40 (1990); Paulsson et al., J. Mol. Biol., 211:331-49 (1990)]) to produce a partially-processed form of about 29 kD; and cleavage (apparently extracellularly) of an amino-terminal peptide (corresponding approximately to amino acids 32-103 of SEQ ID NO: 4) to produce a fully-processed mature form of about 21-23 kD. Experimental evidence demonstrates that partially-processed forms of VEGF-C (e.g., the 29 kD form) are able to bind the VEGFR-3 receptor, whereas high affinity binding to VEGFR-2 occurs only with the fully processed forms of VEGF-C.

Moreover, it has been demonstrated that amino acids 103-227 of SEQ ID NO: 4 are not all critical for maintaining VEGF-C functions. A polypeptide consisting of amino acids 113-213 (and lacking residues 103-112 and 214-227) of SEQ ID NO: 2 retains the ability to bind and stimulate VEGFR-3, and it is expected that a polypeptide spanning from about residue 131 to about residue 211 will retain VEGF-C biological activity. The cysteine residue at position 156 has been shown to be important for VEGFR-2 binding ability. However, VEGF-C $\Delta C_{156}$ polypeptides (i.e., analogs that lack this cysteine due to deletion or substitution) remain potent activators of VEGFR-3, and are therefore considered to be among the preferred candidates for treatment of lymphedema. (It has been shown that a VEGF-C C156S serine substitution analog promotes lymphatic growth when over-expressed in the skin of transgenic mice behind the K14 promotee, in a manner analogous to what was described in Jeltsch et al., Science, 276:1423 (1997), incorporated herein by reference.) The cysteine at position 165 of SEQ ID NO: 4 is essential for binding to either receptor, whereas analogs lacking the cysteines at positions 83 or 137 compete with native VEGF-C for binding with both receptors and are able to stimulate both receptors.

An alignment of human VEGF-C with VEGF-C from other species (performed using any generally accepted alignment algorithm) suggests additional residues wherein modifications can be introduced (e.g., insertions, substitutions, and/or deletions) without destroying VEGF-C biological activity. Any position at which aligned VEGF-C polypeptides of two or more species have different amino acids, especially different amino acids with side chains of different chemical character, is a likely position susceptible to modification without concomitant elimination of function. An exemplary alignment of human, murine, and quail VEGF-C is set forth in FIG. 5 of PCT/US98/01973.

Apart from the foregoing considerations, it will be understood that innumerable conservative amino acid substitutions can be performed to a wildtype VEGF-C sequence which are likely to result in a polypeptide that retains VEGF-C biological activities, especially if the number of such substitutions is small. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine). Addition or deletion of one or a few internal amino acids without destroying VEGF-C biological activities also is contemplated.

Without intending to be limited to a particular theory, the mechanism behind the efficacy of VEGF-C in treating or preventing lymphedema is believed to relate to the ability of VEGF-C to stimulate VEGFR-3 signaling. Administration of VEGF-C in quantities exceeding those usually found in interstitial fluids is expected to stimulate VEGFR-3 in human subjects who, by virtue of a dominant negative heterozygous mutation, have insufficient VEGFR-3 signaling.

The growth factor named Vascular Endothelial Growth Factor D (VEGF-D), as well as human sequences encoding VEGF-D, and VEGF-D variants and analogs, have been described in detail in International Patent Application Number PCT/US97/14696, filed 21 Aug. 1997 and published on 26 Feb. 1998 as International Publication Number WO 98/07832; and in Achen, et al., Proc. Nat'l Acad. Sci. U.S.A., 95(2): 548-553 (1998), both incorporated herein by reference in the entirety. As explained therein in detail, human VEGF-D is initially produced in human cells as a prepro-VEGF-D polypeptide of 354 amino acids. A cDNA and deduced amino acid sequence for human prepro-VEGF-D are set forth in SEQ ID Nos: 5 and 6, respectively. VEGF-D sequences from other species also have been reported. See Genbank Accession Nos. D89628 (Mus musculus); and AF014827 (Rattus norvegicus), for example, incorporated herein by reference.

The prepro-VEGF-D polypeptide has a putative signal peptide of 21 amino acids and is apparently proteolytically processed in a manner analogous to the processing of prepro-VEGF-C. A "recombinantly matured" VEGF-D lacking residues 1-92 and 202-354 of SEQ ID NO: 6 retains the ability to activate receptors VEGFR-2 and VEGFR-3, and appears to associate as non-covalently linked dimers. Thus, preferred VEGF-D polynucleotides include those polynucleotides that comprise a nucleotide sequence encoding amino acids 93-201 of SEQ ID NO: 6.

The subject matter of the invention is further described and demonstrated with reference to the following examples.

EXAMPLE 1

Demonstration that Hereditary Lymphedema is Linked to the VEGFR-3 Locus

The following experiments, conducted to identify a gene or genes contributing to susceptibility to develop lymphedema, demonstrated that hereditary lymphedema correlates, in at least some families, to the chromosomal locus for the VEGFR-3 gene.

Overview

Families with inherited lymphedema were identified for the purpose of conducting a linkage and positional candidate gene analysis. Thirteen distinct families from the United States and Canada were identified through referrals from lymphedema treatment centers, lymphedema support groups, and from interne correspondence (worldwide web site at www.pittedu/~genetics/lymph/). The study protocol was approved by the Institutional Review Board of the University of Pittsburgh and participants gave written informed consent. All members of the families were of western European ancestry. Forty members of one family ("Family 101") were examined during a family reunion by a physiatrist experienced in lymphedema treatment. Family members were considered affected with hereditary lymphedema if they exhibited asymmetry or obvious swelling of one or both legs. Members of the other 12 families were scored as affected if they had received a medical diagnosis of lymphedema, or if there were personal and family reports of extremity swelling or asymmetry. Medical records were obtained to verify status whenever possible. For the purpose of linkage analysis, individuals with very mild or intermittent swelling, heavyset legs, obesity, or a history of leg infections as the only symptom were considered to have indeterminate disease status.

In the 13 families, 105 individuals were classified as affected, with a male:female ratio of 1:2.3. The age of onset of lymphedema symptoms ranged from prenatal (diagnosed by ultrasound) to age 55. When affected by normal matings were analyzed, 76 of 191 children were affected, yielding a penetrance of 80%. First degree relatives of affected individuals were considered at risk.

Biological samples were obtained from members of the thirteen families to conduct the genetic analyses. DNA was isolated from the EDTA-anticoagulated whole blood by the method of Miller et al., *Nucleic Acids Res.*, 16: 1215 (1998), and from cytobrush specimens using the Puregene DNA isolation kit (Gentra Systems, Minneapolis, Minn.). Analysis of the markers used in the genome scan were performed by methods recognized in the art. [See Browman et al., *Am. J. Hum. Genetic.*, 63:861-869 (1998); see also the NHLBI Mammalian Genotyping Service world-wide web sites (www.marshmed.org/genetics/methods/per.htm; and www.marshmed.org/genetics/methods/gel.htm).

Two-point linkage analysis was conducted using an autosomal dominant model predicting 80% penetrance in the heterozygous state, 99% penetrance in the homozygous state, and a 1% phenocopy rate. The frequency of the disease allele was set at 1/10,000. Microsatellite marker allele frequencies were calculated by counting founder alleles, with the addition of counts of non-transmitted alleles. Multipoint analysis was carried out using distances obtained from the Location Database (LDB-http://cedar.genetics.soton.ac.ukipublic html). Multipoint and 2-point analyses were facilitated using the VITESSE (v1.1) program. [O'Connell, J. R. and Weeks, D. E., (1995), *Nature Genet.*, 11:402-408].

DETAILED DESCRIPTION OF METHODS AND RESULTS

The first family studied, Family 101, was a large, multi-generational family demonstrating early onset lymphedema. (See FIG. 1.) Forty individuals of this family were examined and DNA sampled. In addition, blood was obtained from another 11 members from mailing kits. Linkage simulation was performed using SLINK [Weeks et al., *Am. J. Hum. Genet.* 47:A204 (1990)] and linkage was analyzed using MSIM [Ott, J., *Proc. Nat. Acad. Sci. USA*, 86:4175-4178 (1989)] to estimate the potential power of two point linkage analysis in the family. Marker genotypes were simulated for a marker with heterozygosity of 0.875 under a linked ($\theta=0$) and unlinked ($\theta=0.5$) model using the 51 available individuals. The simulation showed that the power to detect linkage was greater than 90% for a LOD score threshold of $Z(\theta)$ 2.0. The false positive rate was less than 5%.

Shortly thereafter, two additional families (designated Families 106 and 111) segregating for autosomal dominant lymphedema were identified. These three families (FIGS. 1A-1C, Families 101, 106 and 111) were genotyped for 366 autosomal markers by the NHLBI Mammalian Genotyping Service (www.marshmed.org/genetics). Genotypes were checked for consistency using Pedcheck [O'Connell, J. R. and Weeks, D. E., *Am. J. Hum. Genet.*, 61:A288 (1997)]. Two point linkage analysis was performed using VITESSE [O'Connell, J. R. and Weeks, D. E., *Nature Genet.*, 11:402-408 (1995)]. The model for linkage assumed an autosomal dominant model of inheritance, a disease allele frequency of 0.0001 and a penetrance of 0.80.

The results from the genomic scan can be briefly summarized as follows. A summed LOD score of greater than 4.0 was observed from distal chromosome 5, markers D5S1456, D5S817 and D5S488. The markers on distal chromosome 5q were the only markers having Z>3.0, the criteria established for statistical significance. LOD scores greater than 2.0 ($\theta=0$-0.15) were also detected for chromosome 12 (D12S391 Z=2.03, all families), and chromosome 21 (D21S1440 Z=2.62, all families). The largest two-point LOD (Z=4.3; $\theta=0$) was observed for marker D5S408, localized to chromosome 5q34-q35.

Figure 2:
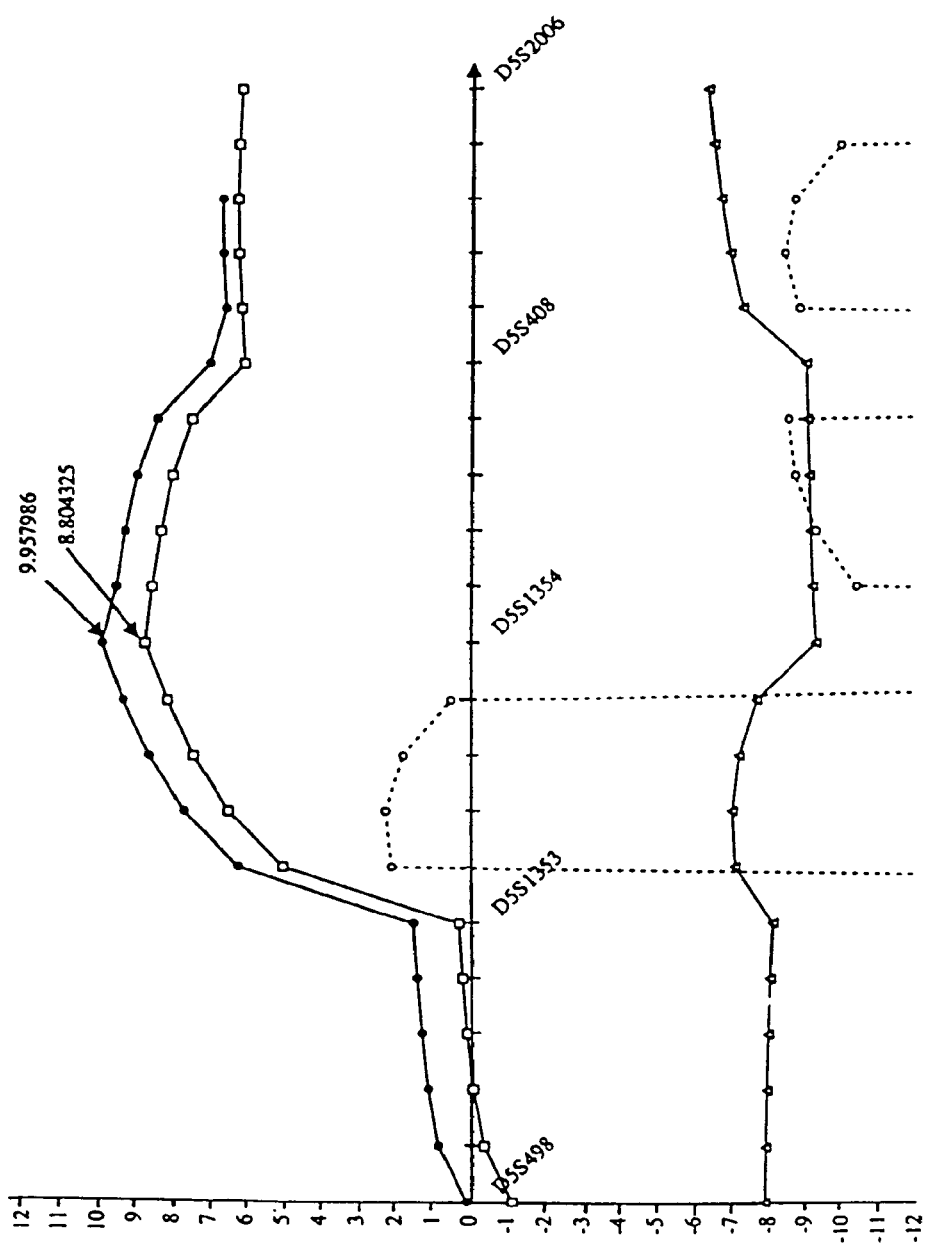
FIG. 2 is a graph summarizing VITESSE analysis of lymphedema families with markers localized to chromosome 5q34-q35. In the graph, filled circles represent analyses for Families 101, 105, 106, and 111; open boxes represent analyses for Families 101, 106, and 111; open circles represent the VEGFR-3 gene; and open triangles represent Family 135. The one LOD confidence interval lies completely within the interval flanked by markers D5S1353 and D5S408 and overlaps the most likely location of Flt4 (VEGFR-3). Linkage is excluded for the entire region for family 135.

This initial chromosomal mapping was further refined by genotyping the three affected families for eight additional markers localized to region 5q34-q35. Six of these were informative for linkage (D5S653, D5S498, D5S408, D5S2006, D5S1353 and D5S1354). Linkage analysis of these markers using VITESSE yielded a 2-point LOD score of 6.1 at $\theta=0$ for marker D5S1354 (Table 1) and a maximum multipoint LOD score of 8.8 at marker D5S1354 (FIG. 2). These findings supported the localization of a gene within chromosome band 5q34-q35 that is a predisposing factor in hereditary lymphedema.

TABLE 1

LOD scores for individual families estimated over the interval defined by markers D5S498 and D5S2006.

|  | $Z(\theta)$ 0.0 | $Z(\theta)$ 0.01 | $Z(\theta)$ 0.05 | $Z(\theta)$ 0.1 | $Z(\theta)$ 0.2 |
|---|---|---|---|---|---|
| Locus D5S498 | | | | | |
| Family 101 | −3.18 | −2.33 | −0.45 | 0.42 | 0.88 |
| Family 106 | 1.08 | 1.07 | 1.05 | 0.99 | 0.81 |
| Family 111 | −0.85 | −0.77 | −0.53 | −0.34 | −0.13 |
| Family 105 | 1.22 | 1.20 | 1.11 | 0.98 | 0.72 |
| Family 135 | −2.48 | −1.85 | −1.12 | −0.75 | −0.38 |
| Locus D5S1353 | | | | | |
| Family 101 | −2.99 | −2.48 | −1.21 | −0.63 | −0.18 |
| Family 106 | 0.28 | 0.29 | 0.35 | 0.38 | 0.38 |
| Family 111 | −1.06 | −1.02 | −0.88 | −0.72 | −0.42 |
| Family 105 | 0.72 | 0.71 | 0.65 | 0.56 | 0.39 |
| Family 135 | −8.03 | −4.18 | −2.09 | −1.13 | −0.30 |
| Locus D5S1354 | | | | | |
| Family 101 | 6.09 | 6.02 | 5.69 | 5.21 | 4.07 |
| Family 106 | 1.42 | 1.40 | 1.32 | 1.20 | 0.96 |
| Family 111 | 0.21 | 0.22 | 0.23 | 0.24 | 0.22 |

TABLE 1-continued

LOD scores for individual families estimated over
the interval defined by markers D5S498 and D5S2006.

| | Z(θ) 0.0 | Z(θ) 0.01 | Z(θ) 0.05 | Z(θ) 0.1 | Z(θ) 0.2 |
|---|---|---|---|---|---|
| Family 105 | 0.43 | 0.42 | 0.40 | 0.36 | 0.28 |
| Family 135 | −6.88 | −4.91 | −3.20 | −2.16 | −1.07 |
| Locus D5S408 | | | | | |
| Family 101 | 2.80 | 2.74 | 2.50 | 2.20 | 1.56 |
| Family 106 | 0.66 | 0.68 | 0.73 | 0.76 | 0.71 |
| Family 111 | −1.70 | −1.40 | −0.80 | −0.44 | −0.10 |
| Family 105 | 0.42 | 0.41 | 0.38 | 0.35 | 0.27 |
| Family 135 | −5.22 | −4.24 | −2.58 | −1.67 | −0.80 |
| Locus D5S2006 | | | | | |
| Family 101 | 4.51 | 4.70 | 4.85 | 4.66 | 3.80 |
| Family 106 | 1.17 | 1.16 | 1.11 | 1.03 | 0.83 |
| Family 111 | −1.32 | −1.18 | −0.82 | −0.56 | −0.25 |
| Family 105 | 0.43 | 0.42 | 0.40 | 0.36 | 0.28 |
| Family 135 | −3.86 | −3.20 | −2.11 | −1.45 | −0.73 |

During the completion of the genome scan, an additional ten lymphedema families were ascertained. Two of these families (Families 105 and 135, see FIGS. 1E and 1D), were potentially informative for linkage and were genotyped for markers in the linked region. Examination of the two point LOD scores for the five informative families for markers in the linked region (Table 1) shows that four of the families (101, 105, 106 and 111) are consistent with linkage to chromosome 5q while family 135 excluded linkage across the entire region with LOD scores Z=<−2.0 for all markers. Multipoint linkage analysis of Families 101, 105, 106 and 111 (FIG. 2) yielded a peak LOD score of Z=10 at marker D5S1354. These findings support the existence of at least two loci which predispose to hereditary lymphedema.

The order of markers D5S1353, D5S1354 and D5S408 with respect to each other was uncertain. Multipoint linkage analysis using alternative orders for these markers gave similar results. Marker D5S498 is a framework marker and marker D5S408 is mapped 11.2 centimorgans distal to D5S498, based on the CHLC chromosome 5 sex averaged, recombination minimized map, version 3 (www.chlc.org). The physical distance between D5S498 and D5S408 is estimated as 1.45 megabases based on the Genetic Location Database (LDB) chromosome 5 summary map (cedar.genetics.soton.ac.uk/public_html/).

Database analysis identified sixteen genes within this region. Two of these genes have been identified as having roles in development (MSX2 and VEGFR-3). MSX2 was considered an unlikely candidate gene for lymphedema because of its known involvement in craniofacial development [Jabs et al., Cell, 75: 443-450 (1993)]. VEGFR-3, the gene encoding a receptor for VEGF-C, was selected as a better candidate gene for initial further study for the following reasons.

(1) VEGFR-3 is expressed in developing lymphatic endothelium in the mouse [Kukk et al., Development, 122: 3829-3837 (1996); and Kaipainen et al., Proc. Nat. Acad. Sci. USA, 92: 3566-3570 (1995)];

(2) expression of VEGFR-3 is induced in differentiating avian chorioallantoic membrane [Oh et al., Dev. Biol., 188:96-109 (1997)]; and (3) overexpression of VEGF-C, a ligand of VEGFR-3, leads to hyperplasia of the lymphatic vessels in transgenic mice [Jeltsch et al., Science, 276: 1423-1425 (1997)].

To explore the potential role of VEGFR-3 in lymphedema, probands from the thirteen lymphedema families were screened for variation by direct sequencing of portions of the VEGFR-3 gene. The sequencing strategy used amplification primers generated based upon the VEGFR-3 cDNA sequence (SEQ ID NO: 1) and information on the genomic organization of the related vascular endothelial growth factor receptor-2 (VEGFR-2/KDR/flk-1) [Yin et al., Mammalian Genome, 9: 408-410 (1998)]. Variable positions (single nucleotide polymorphisms), the unique sequence primers used to amplify sequences flanking each variable site, and the method of detecting each variant are summarized in Table 2.

TABLE 2

Location, amplification primer sequences, amplification conditions, and detection methods for five intragenic single nucleotide polymorphisms in the human VEGFR-3 gene

| Position in VEGFR-3 gene | Primer 1 sequence | Primer 2 sequence | Ann. temp | Base [MgCl$_2$] | Detection change Method |
|---|---|---|---|---|---|
| Exon 12, amino acid 641 | tcaccatcgatccaagc (SEQ ID NO: 7) | agttctgcgtgagccgag (SEQ ID NO: 8) | 56° C. | 1.0 mM | C→T Sequencing |
| Exon 24, amino acid 1114 | caggacgggtgacttga (SEQ ID NO: 9) | gcccaggcctgtctactg (SEQ ID NO: 10) | 56° C. | 1.0 mM | C→T Sequencing |
| Exon 3, amino acid 175 | ccagctcctacgtgttcg (SEQ ID NO: 11) | ggcaacagctggatgtca (SEQ ID NO: 12) | 56° C. | 1.0 mM | C→T HhaI |
| 65 bp 3' to Exon 6 | ctgtgagggcgtgggagt (SEQ ID NO: 13) | gtcctttgagccactgga (SEQ ID NO: 14) | 54° C. | 1.5 mM | G→A StyI |
| 55 bp 3' to Exon 2 | cacacgtcatcgacaccggtg (SEQ ID NO: 15) | ggcaacagctggatgtca (SEQ ID NO: 16) | 56° C. | 1.5 mM | C→T ApaI |

All amplifications were done for 35 cycles with denaturation at 94° for 30 seconds, annealing as above for 30 seconds, and extension at 72° for 30 seconds.

Amplification and sequencing primers were synthesized by the DNA Synthesis Facility, University of Pittsburgh. Amplification primers were tagged at the 5' end with the forward or reverse M13 universal sequence to facilitate direct sequencing. Amplimers were subjected to cycle sequencing using the dRhodamine terminator ready reaction kit or the Dye Primer ready reaction kit for −M13 and M13 Rev primers (Perkin Elmer) and analyzed on the Prism ABI 377 fluorescent sequencer. Sequences were aligned for further analysis using SEQUENCHER 3.0 (Gene Codes).

Genomic sequence from approximately 50% of the VEGFR-3 gene was determined in this manner, and five single nucleotide variants were observed. Two of the variants occurred in introns, and a third was a silent substitution in predicted exon 3. These intragenic polymorphisms were used to map the VEGFR-3 gene. As shown in FIG. 2, VEGFR-3 maps within the region of chromosome 5q linked to the lymphedema phenotype, consistent with it being selected as a candidate gene. In two families, (Family 127, pedigree not shown, and Family 135), a C→T transition was identified at nucleotide position 1940 of the VEGFR-3 cDNA (SEQ ID NO: 1). This nucleotide substitution is predicted to lead to a non-conservative substitution of serine (codon TCC) for proline (codon CCC) at residue 641 (putative exon 12, within the sixth immunoglobulin-like region of the receptorL extracellular domain) of the amino acid sequence of the receptor (SEQ ID NO: 2). However, this sequence change was observed in 2 of 120 randomly selected individuals from the general population (240 alleles). Also, in one of the two families in which this variant was initially detected, family 135, linkage between lymphedema and chromosome 5q markers was excluded (Table 1 and FIG. 2). In probands from the other ten families, wild type sequence was observed at nucleotide position 1940. Collectively, these results suggest that this P641 S variant is not causative.

In one nuclear family (Family 127, pedigree shown in FIG. 1F) a C→T transition was observed at nucleotide position 3360 (SEQ ID NO: 1) of the VEGFR-3 cDNA. This nucleotide substitution is predicted to lead to a non-conservative substitution of leucine (codon CTG) for proline (codon CCG) at residue 1114 of the amino acid sequence of the receptor (SEQ ID NO: 2). This P1114L mutation is predicted to lie in the intracellular tyrosine kinase domain II involved in intracellular signaling [Pajusola et al., *Cancer Res.,* 52:5738-5743 (1992)]. Direct sequencing of predicted exon 24 of the VEGFR-3 gene alleles from members of this family identified this substitution only in affected and at-risk family members. This sequence change was not observed in 120 randomly selected individuals of mixed European ancestry from the general population (240 alleles). In probands from the other 11 families, wild type sequence was observed at nucleotide position 3360.

Collectively, this data demonstrates that a missense mutation that causes a non-conservative substitution in a kinase domain of the VEGFR-3 protein correlates strongly with a heritable lymphedema in one family, and suggests that other mutations in the same gene may exist that correlate with heritable lymphedema in other families. As explained above, only a portion of the VEGFR-3 gene sequence was analyzed to identify this first mutant of interest. Additional sequencing, using standard techniques and using the known VEGFR-3 gene sequence for guidance, is expected to identify additional mutations of interest that are observed in affected and at-risk members of other families studied.

EXAMPLE 2

Demonstration that a C→T Missense Mutation at Position 3360 in the VEGFR-3 Coding Sequence Results in a Tyrosine Kinase Negative Mutant The results set forth in Example 1 identified two missense mutations in the VEGFR-3 coding sequence, one of which (C→T at position 3360) appeared to correlate with heritable lymphedema and one of which (C→T transition at position 1940) did not. The following experiments were conducted to determine the biochemical significance of these mutations on VEGFR-3 biological activity.

To analyze how the two single amino acid substitutions affect the VEGFR-3-mediated signaling, the corresponding mutant receptor expression vectors were generated using site-directed mutagenesis procedures and expressed in 293T cells by transient transfection. The long form of human VEGFR-3 cDNA (SEQ ID NO: 1) was cloned as a Hind III-Bam HI fragment from the LTR-FLT41 plasmid [Pajusola et al., *Oncogene* 8: 2931-2937 (1993)] into pcDNA3.1/Z(+) (Invitrogen). The P641S and P1114L mutants of VEGFR-3 were generated from this construct with the GeneEditor™ in vitro Site-Directed Mutagenesis System (Promega) using the following oligonucleotides (the C→T mutations are indicated with bold letters):

5'-CCTGAGTATCTCCCGCGTCGC-3' (SEQ ID NO: 17) for P641S mutation; and

5'-GGTGCCTCCCTGTACCCTGGG-3' (SEQ ID NO: 18) for P1114L mutation.

For the transient expression studies, 293T cells were grown in Dulbecco's modified Eagle's medium (DMEM) supplemented with 10% fetal calf serum (GIBCO BRL, Life Technologies, Gaithersburg, Md.), glutamine, and antibiotics. Cells were transfected with 20 μg of plasmid encoding the wild type or mutant VEGFR-3 forms using the calcium phosphate method, and harvested 36 hours after transfection for immunoprecipitation and Western blotting. Under these conditions, RTK overexpression results in ligand-independent activation, thus allowing the receptor phosphorylation to be studied. An empty vector was used for mock (control) transfections. (It will be appreciated that ligand stimulation assays of VEGFR-3 forms also can be employed, e.g., as described in U.S. Pat. No. 5,776,755, incorporated herein by reference, using VEGF-C or VEGF-D ligands.)

In order to investigate the effect of the two VEGFR-3 mutants on the tyrosine phosphorylation of the VEGFR-3, Western blotting analysis was performed using anti-phosphotyrosine antibodies. The cell monolayers were washed three times with cold phosphate-buffered saline (PBS, containing 2 mM vanadate and 2 mM PMSF) and scraped into RIPA buffer (150 mM NaCl, 1% Nonidet P40, 0.5% deoxycholic acid sodium salt, 0.1% SDS, 50 mM Tris-HCl, pH 8.0) containing 2 mM Vanadate, 2 mM PMSF, and 0.07 U/ml Aprotinin.

The cell lysates were sonicated and centrifuged for 10 minutes at 19,000×g, and the supernatants were incubated for 2 hours on ice with 2 μg/ml of monoclonal anti-VEGFR-3 antibodies (9D9f9) [Jussila et al., *Cancer Res.,* 58: 1599-604 (1998)]. Thereafter, Protein A sepharose (Pharmacia) beads were added and incubation was continued for 45 minutes with rotation at +4° C. The sepharose beads were then washed three times with ice-cold RIPA buffer and twice with PBS (both containing 2 mM vanadate, 2 mM PMSF), analyzed by 7.5% SDS-PAGE and transferred to a nitrocellulose filter (Protran Nitrocellulose, Schleicher & Schuell, No. 401196) using semi-dry transfer apparatus. After blocking the filter with 5% BSA in TBS-T buffer (10 mM Tris, pH 7.5, 150 mM NaCl, 0.05% Tween 20), the filters were incubated with the phosphotyrosine-specific primary antibodies (Upstate Biotechnology, #05-321), followed by biotinylated goat-anti-mouse immunoglobulins (Dako, E0433) and Biotin-Streptavidin HRP complex (Amersham, RPN1051). The bands were visualized by the enhanced chemiluminescence (ECL) method.

After analysis for phosphotyrine-containing proteins, the filters were stripped by washing for 30 minutes at +50° C. in 100 mM 2-mercaptoethanol, 2% SDS, 62.5 mM Tris-HCl, pH 6.7, with occasional agitation. The filters were washed with TBS-T, blocked again with BSA as described above, and analyzed for the presence of VEGFR-3 using the 9D9f9 antibodies and HRP-conjugated rabbit-anti-mouse immunoglobulins (Dako, P0161).

The Western analyses revealed that the P641S mutant receptor was phosphorylated normally, i.e., in a manner similar to the wild type control. However, the proteolytic processing of the P641S receptor protein may be affected, as the 175 kD and 125 kD polypeptides seemed to have a higher relative density when compared to the 195 kD form.

In contrast, no phosphorylated P1114L mutant protein was detected using the phosphotyrosine antibodies. The expression of similar amounts of the VEGFR-3 protein (normal and both mutants) was confirmed using the monoclonal 9D9f9 antibody, which is directed towards the extracellular domain of the VEGFR-3. Both the P641S and the P1114L mutant VEGFR-3 migrated slightly faster than the wild type VEGFR-3 in the gel electrophoresis.

In order to analyze the possible dominant negative effect of the P1114L mutant on the wild-type receptor, a second, similar set of experiments were performed wherein the 293T cells were transfected with an increasing amount of the P1114L expression vector in combination with decreasing amounts of the wild type vector. Wild type to mutant ratios of 1:0, 3:1, 1:1, 1:3 and 0:1 were used. The cells were lysed 48 hours after transfection and the lysates were analyzed by immunoprecipitation and Western blotting as described above. These experiments permitted evaluation of whether the mutant protein interferes with wild type protein phosphorylation and estimation of the minimal amount of the WT protein needed for observable tyrosyl autophosphorylation. Immunoprecipitates from cells transfected with only the WT plasmid revealed WT protein that was strongly phosphorylated in this experiment (lane 2), whereas immunoprecipitates from cells transfected with only the mutant plasmid were again inactive (unphosphorylated).

Interestingly, when transfection was made using 75% of WT and 25% of mutant plasmid, the phosphorylation of the receptors was decreased by about 90%. This result strongly suggests that the P1114L mutant receptor forms heterodimers with the WT receptor, but cannot phosphorylate the WT receptor, thus failing to activate it. Under this theory, the WT receptor monomers in the heterodimers would also remain inactive, causing a disproportionate decrease of the total amount of activated receptor, when co-transfected with the mutant. Wildtype-wildtype homodimers would remain active and be responsible for the observed signaling. When the wild type and mutant receptor expression vectors were transfected at a 1:1 ratio, the VEGFR-3 phosphorylation was about 4% of the wild type alone, whereas at a 1:3 ratio, no tyrosine phosphorylation of VEGFR-3 was observed.

The foregoing results are consistent with the linkage analyses in Example 1: the mutation at position 641 that did not appear to correlate with lymphedema also did not appear to be disfunctional, whereas the mutation at position 1114 appeared to cause a dominant negative mutation that shows no tyrosine phosphorylation alone and that drastically reduces VEGFR-3 signaling in cells expressing both the mutant and wild type VEGFR-3 genes.

Collectively, these data indicate that the P1114L VEGFR-3 mutant is unable to act as a part of the signaling cascade, and also acts in a dominant negative manner, thus possibly interfering partially with the activation of the wild type VEGFR-3. Such effects of the mutation may eventually lead to lymphedema.

EXAMPLE 3

Treatment of Lymphedema with a VEGFR-3 Ligand

The data from Examples 1 and 2 collectively indicate a causative role in heritable lymphedema for a mutation in the VEGFR-3 gene that interferes with VEGFR-3 signaling. Such a mutation behaves in an autosomal dominant pattern, due to the apparent necessity for receptor dimerization in the signaling process. However, the data from Example 2 suggests that some residual signaling may still occur in heterozygous affected individuals, presumably through pairing of VEGFR-3 proteins expressed from the wild type allele. The following experiments are designed to demonstrate the efficacy of VEGFR-3 ligand treatment in such affected individuals, to raise VEGFR-3 signaling to levels approaching normal and thereby ameliorate/palliate the symptoms of hereditary lymphedema.

Initially, an appropriate animal model is selected. Several potential animal models have been described in the literature. [See, e.g., Lyon et al., *Mouse News Lett.* 71: 26 (1984), *Mouse News Lett.* 74: 96 (1986), and *Genetic variants and strains of the laboratory mouse,* 2nd ed., New York: Oxford University Press (1989), p. 70 (Chylous ascites mouse); Dumont et al., *Science,* 282: 946-949 (1998) (heterozygous VEGFR-3 knockout mouse); Patterson et al., "Hereditary Lymphedema," *Comparative Pathology Bulletin,* 3: 2 (197)) (canine hereditary lymphedema model); van der Putte, "Congenital Hereditary Lymphedema in the Pig," *Lympho,* 11: 1-9 (1978); and Campbell-Beggs et al., "Chyloabdomen in a neonatal foal," *Veterinary Record,* 137: 96-98 (1995).] Those models which are determined to have analogous mutations to the VEGFR-3 gene are preferred. Analogous mutations would include mutations affecting corresponding residues and also mutations affecting different residues but causing similar functional alterations. The *Chylous ascites* mouse VEGFR-3 gene contains a missense mutation at a position corresponding to residue 1053 of SEQ ID No. 2, which maps to the catalytic pocket region of the tyrosine kinase catalytic domain. Thus, the "Chy" mouse is expected to display similar functional alterations to human mutations affecting tyrosine kinase activity, a prediction which can be confirmed by functional assays such as those described in Example 2. In a preferred embodiment, "knock in" homologous recombination genetic engineering strategies are used to create an animal model (e.g., a mouse model) having a VEGFR-3 allelic variation analogous to the human variations described herein. [See, e.g., Partanen et al., *Genes & Development,* 12: 2332-2344 (1998) (gene targeting to introduce mutations into another receptor protein (FGFR-1) in mice).] For example, the P1114L mutation in human VEGFR-3 occurs in a VEGFR-3 region having highly conserved amino acid identity with murine VEGFR-3 (Genbank Accession No. L07296). Thus, a corresponding P1114L can be introduced into the murine VEGFR-3 by "knock-in" homologous recombination. Optionally, such mice can be bred to the heterozygous VEGFR-3 knockout mice or Chy mice described above to further modify the phenotypic severity of the lymphedema disease.

The mice as described above are treated with a candidate therapeutic, e.g., a recombinant mature form of VEGF-C, at various dosing schedules, e.g., once daily by intravenous (IV) or intramuscular (IM) injection at a dose of 1-1000 ng/g body weight, preferably 10-100 ng/g, which should result in a peak level saturating VEGFR-3 ($K_d$ about 150 µM) but not VEGFR-2 ($K_d$ around 400 pM). For VEGFR-3-specific forms, such as VEGF-C$\Delta$C$_{156}$, even higher dosing is contemplated, to sustain VEGFR-3-saturating physiological concentrations for longer periods. Direct IM injection at multiple sites in the muscles of affected extremities is a preferred route of administration. The dosing is adjusted according to the efficacy of the treatment and the presence of possible side effects due to the lowering of blood pressure, which has been observed in response to VEGF administration IV. The efficacy of treatment is measured via NMRI imaging of the water content and volume of swelling of the abdomen and the extremities of the animals. The amount of fluid in the abdominal cavity is estimated and the animals are weighed during the follow-up.

In studies using VEGFR-3−/+x Chy mice progeny, the animals will also have the β-galactosidase marker in their lymphatic endothelium. After a successful treatment, the treated and non-treated experimental animals and VEGFR-3−/+controls are killed and their lymphatic vessels are visualized by β-gal and antibody staining. The staining patterns of experimental and control animals are compared for vessel diameter, numbers of endothelial cells, density of blood and lymphatic vessels, and nuclear density/section surface area for the estimation of tissue oedema.

Such experiments are repeated with various candidate therapeutics (e.g., VEGF-C or VEGF-D recombinant polypeptides; VEGF-C and VEGF-D gene therapy vectors; and combinations thereof) at various dosing schedules to determine an optimum treatment regimen.

EXAMPLE 4

Chromosomal Structure of the Human VEGFR-3 Gene

Sequencing and mapping of human DNA corresponding to the VEGFR-3 locus has indicated that this gene consists of thirty exons separated by twenty-nine introns of varying size. The exon intron organization is summarized as follows

| EXON NUMBER | Bp of SEQ ID NO: 1 size (bp) | INTRON SIZE |
|---|---|---|
| 1 | 20-77 58 bp | unknown |
| 2 | 78-174 97 bp | >1 kb |
| 3 | 175-419 245 bp | 218 bp |
| 4 | 420-532 113 bp | 120 bp |
| 5 | 533-695 163 bp | 107 bp |
| 6 | 696-835 140 bp | 269 bp |
| 7 | 836-1004 169 bp | 261 bp |
| 8 | 1005-1122 118 bp | >1 kb |
| 9 | 1123-1277 155 bp | unknown |
| 10 | 1278-1440 163 bp | >1 kb |
| 11 | 1441-1567 127 bp | unknown |
| 12 | 1568-1676 109 bp | unknown |
| 13 | 1677-2039 363 bp | 293 bp |
| 14 | 2040-2186 147 bp | 99 bp |
| 15 | 2187-2318 132 bp | approx. 160 bp |
| 16 | 2319-2425 107 bp | 301 bp |
| 17 | 2426-2561 139 bp | >464 bp |
| 18 | 2562-2666 105 bp | unknown |
| 19 | 2667-2780 114 bp | 143 bp |
| 20 | 2781-2869 89 bp | >1 kb |
| 21 | 2870-3020 151 bp | unknown |
| 22 | 3021-3115 95 bp | unknown |
| 23 | 3116-3238 123 bp | unknown |
| 24 | 3239-3350 112 bp | 974 bp |
| 25 | 3351-3450 100 bp | 400 bp |
| 26 | 3451-3557 107 bp | unknown |
| 27 | 3558-3705 148 bp | >1 kb |
| 28 | 3706-3826 121 bp | unknown |
| 29 | 3827-3912 86 bp | unknown |
| 30a (Flt4 short) | 3913-4111 199 bp | 3.7 kb |
| 30b (Flt4long) | 3913-4416 >504 bp | (CDS 504 bp) |

The foregoing information permits rapid design of oligonucleotides for amplifying select portions of the VEGFR-3 gene from genomic DNA, or RNA, or cDNA, to facilitate rapid analysis of an individual's VEGFR-3 coding sequence, to determine whether the individual possesses a mutation that correlates with a lymphedema phenotype.

EXAMPLE 5

Identification of Additional Non-conservative Missense Mutants

Using procedures essentially as described in Example 1, the VEGFR-3 coding sequences from additional affected and unaffected individuals from families having members suffering from heritable lymphedema were studied. The analysis focused on families with statistical linkage to chromosome 5q as described in Example 1. The additional analysis included the PCR amplification and sequencing of Exon 17. Exon 22, and Exon 23 sequences with the following PCR primers:

Exon 17-1   5'-CATCAAGACGGGCTACCT-3'   (SEQ ID NO: 23)

Exon 17-2   5'-CCGCTGACCCCACACETT-3'   (SEQ ID NO: 24)

Exon 22-1   5'-GAGTTGACCTCCCAAGGT-3'   (SEQ ID NO: 25)

Exon 22-2   5'-TCTCCTGGACAGGCAGTC-3'   (SEQ ID NO: 26)

Exon 23-1   5'-GAGTTGACCTCCCAAGGT-3'   (SEQ ID NO. 27)

Exon 23-2   5'-TCTCCTGGACAGGCAGTC-3'   (SEQ ID NO. 28)

These additional studies identified four additional non-conservative missense mutations in evolutionarily conserved amino acids in kinase domains I and II of human VEGFR-3. Each mutation, shown in Table 3 below, was observed in a single independently ascertained family, and in each family, the mutation co-segregates with individuals suffering from, or considered at risk for developing, lymphedema. None of these mutations were observed in the VEGFR-3 genes in a random sample of more than 300 chromosomes from individuals from families unafflicted with heritable lymphedema.

TABLE 3

Mutations in VEGFR-3 causing Hereditary Lymphedema*

| Exon | Nucleotide Substitution** | Amino Acid Substitution | Functional Domain |
|---|---|---|---|
| 24 | C3360T | P1114L | Kinase 2 |
| 17 | G2588A | G857R | Kinase 1 |
| 23 | G3141C | R1041P | Kinase 2 |
| 23 | T3150C | L1044P | Kinase 2 |
| 23 | G3164A | D1049N | Kinase 2 |

*Numbers indicate nucleotide or amino acid positions in SEQ ID NOs: 1 and 2.
**It will be appreciated that, since DNA is double-stranded, each mutation could be characterized in two equivalent ways, depending on whether reference is being made to the coding or the non-coding strand.

Referring to SEQ ID NO: 2, the kinase domains of VEGFR-3 comprise approximately residues 843-943 and residues 1009-1165. Within these domains, molecular modeling suggests that residues G852, G854, G857, K879, E896, H1035, D1037, N1042, D1055, F1056, G1057, E1084, D1096 and R1159 are of particular importance in comprising or shaping the catalytic pocket within the kinase domains. See van Der Geer and Hunter, *Ann. Rev. Cell. Biol.*, 10: 251-337 (1994); and Mohammadi et al., *Cell* 86: 577-587 (1996). Thus, this data identifying additional mutations implicate missense mutations within a kinase domain of the VEGFR-3 protein as correlating strongly with a risk for developing a heritable lymphedema phenotype. Mutations which affect residues in and around the catalytic pocket appear particularly likely to correlate with lymphedema. The P1114L mutation, though not situated within the catalytic pocket, is postulated to cause a conformational alteration that affects the catalytic pocket. The G857R mutation is postulated to block the catalytic pocket and/or the ATP binding site of the kinase domain.

EXAMPLE 6

Functional Analysis of Additional VEGFR-3 Missense Mutations

Using procedures essentially as described above in Example 2, the functional state of the G857R, L1044P, and D1049N mutations were analyzed. (PLCLB buffer, comprising 150 mm NaCl, 5% glycerol, 1% Triton X-100, 1.5M MgCl$_2$, 50 mm HEPES, pH 7.5, was substituted for RIPA buffer described in Example 2 for immunoprecipitation and Western blotting protocols.) A VEGFR-3-encoding construct comprising the G857R mutation was generated from the long form of human VEGFR-3 cDNA using the oligonucleotide:

5'-CGG CGC TTT CAG GAA GGT GGT-3'    (SEQ ID NO: 20)

A construct comprising the L1044P mutation was generated from the long form of human VEGFR-3 cDNA using the oligonucleotide:

5'-CGG AAC ATT CCG CTG TCG GAA-3'    (SEQ ID NO: 21)

A construct comprising the D1049N mutation was generated from the long form of human VEGFR-3 cDNA using the oligonucleotide:

5'-GTC GGA AAG CAA CGT GGT GAA-3'.   (SEQ ID NO: 22)

The constructs were transiently transfected into 293T cells and harvested for Western blotting essentially as described in Example 2, except for the buffer substitution described above. In contrast to wild type VEGFR-3 and VEGFR-3 containing the P641S mutation, no phosphorylated G857R or L1044P mutant protein was detected using the phosphotyrosine antibodies, consistent with the results that had been observed for P1114L. The expression of similar amounts of the VEGFR-3 protein was confirmed using the monoclonal 9D9f9 antibody, which is directed towards the extracellular domain of the VEGFR-3 in the Western blotting. This data suggested that these observed mutations did indeed affect VEGFR-3 kinase function. The D1049N mutant appeared to retain at least some tyrosine kinase activity. It is also noteworthy that VEGFR-1 and VEGFR-2 contain an asparagine residue at the position in their tyrosine kinase domains which corresponds to position 1049 of VEGFR-3. Together, these data suggest that the D1049N variation may only be an allelic variant that correlates with hereditary lymphedema, rather than a causative mutation.

To determine whether the VEGFR-3 mutants function in a dominant negative manner, each construct was co-transfected at varying ratios with wild type receptor into 293T cells essentially as described in Example 2. Unlike the results observed for P1114L and described in Example 2, neither the G857R mutant nor the L1044P mutant seemed to interfere with phosphorylation of the co-transfected wild type receptor.

The absence of a dominant negative effect in these experiments does not foreclose a conclusion that the mutations described above are causative. It has been found that a significant fraction of ligand-activated receptor tyrosine kinases traffic to the lysosomal compartment after internalization, where they are degraded. However, receptors which are not ligand-activated preferentially recycle back to the cell surface after internalization. Thus, it is possible that the turnover time of the weakly phosphorylated mutant receptor is significantly longer than that of the wild type receptor protein. If this were true, the amount of the mutant receptor on the endothelial cell surface could be considerably higher than the amount of the phosphorylated and rapidly internalized wild type receptor, and any available ligand would thus bind a disproportionally high number of mutant receptors. Both a possible dominant negative effect of the mutant receptor and an abnormally long half-life of the tyrosine kinase negative mutant receptor could eventually lead to lymphedema. Alternatively, a mutation that merely decreases (but does not eliminate) VEGFR-3 tyrosine kinase activity may display a constitutive low level of internalization and degradation that is insufficient to trigger sufficient downstream signalling, but decreases the effective concentration of VEGFR-3 on cell surfaces for ligand binding and effective activation, leading eventually to lymphedema.

EXAMPLE 7

Expression of VEGF-D in COS Cells

A fragment of the human cDNA for VEGF-D, spanning from nucleotide 1 to 1520 of the sequence shown in FIG. 4 and containing the entire coding region, was inserted into the mammalian expression vector pcDNA1-amp. The vector was used to transiently transfect COS cells by the DEAE-Dextran method as described previously (Aruffo and Seed, 1987) and the resulting conditioned cell culture media, collected after 7 days of incubation, were concentrated using Amicon concentrators (Centricon 10 with a 10,000 molecular weight cut off) according to the manufacturer. The plasmids used for transfections were the expression construct for human VEGF-D and, as positive control, a construct made by insertion of mouse VEGF-A cDNA into pcDNA1-amp. The conditioned media were tested in two different bioassays, as described below, and the results demonstrate that the COS cells did in fact express and secrete biologically-active VEGF-D.

EXAMPLE 8

Bioactivities of Internal VEGF-D Polypeptides

Figure 5:
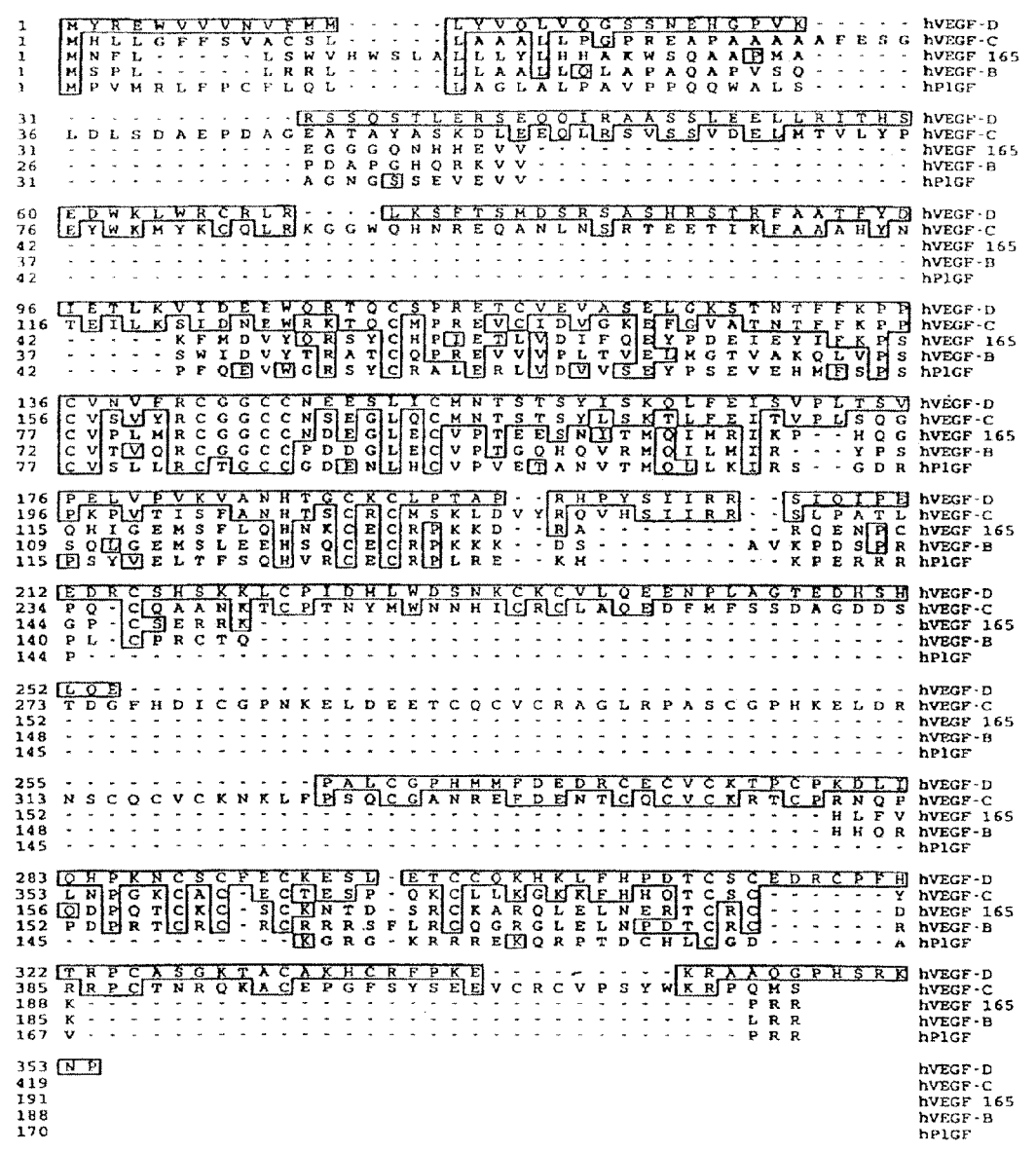

The deduced amino acid sequence for VEGF-D includes a central region which is similar in sequence to all other members of the VEGF family (approximately residues 101 to 196 of the human VEGF-D amino acid sequence as shown in the alignment in FIG. 5). Therefore. it was thought that the bioactive portion of VEGF-D might reside in the conserved region. In order to test this hypothesis, the biosynthesis of VEGF-D was studied, and the conserved region of human VEGF-D was expressed in mammalian cells, purified, and tested in bioassays as described below.

Plasmid Construction

A DNA fragment encoding the portion of human VEGF-D from residue 93 to 201 of SEQ ID NO: 6, ie. with N- and C-terminal regions removed, was amplified by polymerase chain reaction with Pfu DNA polymerase, using as template a plasmid comprising full-length human VEGF-D cDNA. The amplified DNA fragment, the sequence of which was confirmed by nucleotide sequencing, was then inserted into the expression vector pEFBOSSFLAG to give rise to a plasmid designated pEFBOSVEGFDΔNΔC. The pEFBOSSFLAG vector contains DNA encoding the signal sequence for protein secretion from the interleukin-3 (IL-3) gene and the FLAG™ octapeptide. The FLAG™ octapeptide can be recognized by commercially available antibodies such as the M2 monoclonal antibody (IBI/Kodak). The VEGF-D PCR fragment was inserted into the vector such that the IL-3 signal sequence was immediately upstream from the FLAG™ sequence, which was in turn immediately upstream from the VEGF-D sequence. All three sequences were in the same reading frame, so that translation of mRNA resulting from transfection of pEFBOSVEGFDΔNΔC into mammalian cells would give rise to a protein which would have the IL-3 signal sequence at its N-terminus, followed by the FLAG™ octapeptide and the VEGF-D sequence. Cleavage of the signal sequence and subsequent secretion of the protein from the cell would give rise to a VEGF-D polypeptide which is tagged with the FLAG™ octapeptide adjacent to the N-terminus. This protein was designated VEGFDΔNΔC.

In addition, a second plasmid was constructed, designated pEFBOSVEGFDfullFLAG, in which the full-length coding sequence of human VEGF-D was inserted into pEFBOSIFLAG such that the sequence for the FLAG™ octapeptide was immediately downstream from, and in the same reading frame as, the coding sequence of VEGF-D. The plasmid pEFBOSIFLAG lacks the IL-3 signal sequence, so secretion of the VEGF-D/FLAG fusion protein was driven by the signal sequence of VEGF-D. pEFBOSVEGFDfullFLAG was designed to drive expression in mammalian cells of full-length VEGF-D which was C-terminally tagged with the FLAG™ octapeptide. This protein is designated VEGFDfull-FLAG, and is useful for the study of VEGF-D biosynthesis.

Analysis of the Post-Translational Processing of VEGF-D

To examine whether the VEGF-D polypeptide is processed to give a mature and fully active protein, pEFBOSVEGFDfullFLAG was transiently transfected into COS cells (Aruffo and Seed, 1987). Expression in COS cells followed by biosynthetic labeling with .sup.35 S-methionine/cysteine and immunoprecipitation with M2 gel has demonstrated species of approximately 43 kD (fA) and 25 kD(fB). These bands are consistent with the notion that VEGF-D is cleaved to give a C-terminal fragment (FLAG™ tagged) and an internal peptide (corresponding approximately to the VEGFDΔNΔC protein). Reduction of the immunoprecipitates (M2*) gives some reduction of the fA band, indicating the potential for disulphide linkage between the two fragments.

Expression and Purification of Internal VEGF-D Polypeptide

Plasmid pEFBOSVEGFDΔNΔC was used to transiently transfect COS cells by the DEAE-Dextran method as described previously (Aruffo and Seed, 1987). The resulting conditioned cell culture medium (approximately 150 ml), collected after 7 days of incubation, was subjected to affinity chromatography using a resin to which the M2 monoclonal antibody had been coupled. In brief, the medium was run batch-wise over a 1 ml M2 antibody column for approximately 4 hours at 4° C. The column was then washed extensively with 10 mM Tris-HCl, pH 8.0, 150 mM NaCl before elution with free FLAG™ peptide at 25 g/ml in the same buffer. The resulting material was used for the bioassays described below.

In order to detect the purified VEGFDΔNΔC, fractions eluted from the M2 affinity column were subjected to Western blot analysis. Aliquots of the column fractions were combined with 2×SDS-PAGE sample buffer, boiled and loaded onto a 15% SDS polyacrylamide gel. The resolved fractions were transferred to nitrocellulose membrane and non-specific binding sites blocked by incubation in Tris/NaCETween 20 (TST) and 10% skim milk powder (BLOTTO). Membranes were then incubated with monoclonal antibody M2 or control antibody at 3 µg/ml for 2 h at room temperature, followed by extensive washing in TST. Membranes were then incubated with a secondary goat anti-mouse HRP-conjugated antiserum for 1 h at room temperature, followed by washing in TST buffer. Detection of the protein species was achieved using a chemiluminescent reagent (ECL. Amersham).

Under non-reducing conditions a species of molecular weight approximately 23 kD (VEGFDΔNΔC) was detected by the M2 antibody. This is consistent with the predicted molecular weight for this internal fragment (12,800) plus N-linked glycosylation; VEGFDΔNΔC contains two potential N-linked glycosylation sites. A species of approximately 40 kD was also detected, and may represent a non-covalent dimer of the 23 kD protein (VEGFDΔNΔC).

Summary

Two factors have led us to explore internal fragments of VEGF-D for enhanced activity. Firstly, it is the central region of VEGF-D which exhibits amino acid homology with all other members of the VEGF family. Secondly, proteolytic processing which gives rise to internal bioactive polypeptides occurs for other growth factors such as PDGF-BB. In addition, the activity seen with the full length VEGF-D protein in COS cells was lower than for the corresponding conditioned medium from VEGF-A transfected COS cells.

It was predicted that the mature VEGF-D sequence would be derived from a fragment contained within residues 92-205, with cleavage at FAA TFY (residues 60-65 of SEQ ID NO: 6) and IIRR SIQI (residues 173-180 of SEQ ID NO: 6). Immunoprecipitation analysis of VEGF-DfullFLAG expressed in COS cells produced species consistent with the internal proteolytic cleavage of the VEGF-D polypeptide at these sites. Therefore a truncated form of VEGF-D, with the N- and C-terminal regions removed VEGFDΔNΔC), was produced and expressed in COS cells. This protein was identified and purified using the M2 antibody. The VEGFDΔNΔC protein was also detected by the A2 antibody, which recognizes a peptide within the 92-205 fragment of VEGF-D (not shown).

EXAMPLE 9

VEGF-D Binds to and Activates VEGFR-3

The human VEGF-D cDNA was cloned into baculovirus shuttle vectors for the production of recombinant VEGF-D. In addition to baculoviral shuttle vectors, which contained the unmodified cDNA (referred to as "full length VEGF-D") two baculoviral shuttle vectors were assembled, in which the VEGF-D cDNA was modified in the following ways.

In one construct (referred to as "full length VFGF-D-H$_6$") a C-terminal histidine tag was added. In the other construct the putative N- and C-terminal propeptides were removed, the melittin signal peptide was fused in-frame to the N-terminus, and a histidine tag was added to the C-terminus of the remaining VEGF homology domain (referred to as "ΔNAc-MELsp-VEGF-D-H$_6$").

For each of the three constructs baculoviral clones of two or three independent transfections were amplified. The supernatant of High Five (HF) cells was harvested 48 h post infection with high titre virus stocks. The supernatant was adjusted to pH 7 with NaOH and diluted with one volume of D-MEM (0.2% FCS).

The samples were tested for their ability to stimulate tyrosine phosphorylation of VEGFR-3 (Flt-4 receptor) on NIH3T3 cells, as described by Joukov et al, 1996. The supernatant of uninfected cells and the supernatant of cells infected with the short splice variant of VEGF-C, which does not stimulate tyrosine phosphorylation of VEGFR-3, were used as negative controls. VEGF-C modified in the same way as ΔNΔC-meISP-VEGF-D-H$_6$ was used as positive control. The appearance of new bands at 125 and 195 kD indicates phosphorylation, and hence activation, of the receptor.

While the present invention has been described in terms of specific embodiments, it is understood that variations and modifications will occur to those in the art, all of which are intended as aspects of the present invention. Accordingly, only such limitations as appear in the claims should be placed on the invention.

What is claimed:

1. A method of treatment for lymphedema, comprising: administering to a patient with lymphedema a therapeutically effective amount of a polynucleotide that comprises a nucleotide sequence that encodes a vascular endothelial growth factor D (VEGF-D) protein that binds and stimulates wild-type VEGFR-3; and wherein said therapeutically effective amount of said polynucleotide is administered locally at a site of edema in the patient.

2. The method of claim 1, wherein the VEGF-D protein comprises amino acids 92-205 of SEQ ID NO: 6.

3. The method of claim 1, wherein the VEGF-D protein comprises amino acids 101-196 of SEQ ID NO: 6.

4. The method of claim 1, wherein said VEGF-D protein comprises a member selected from the group consisting of: (a) a polypeptide comprising the amino acid sequence of SEQ ID NO: 6; and (b) a polypeptide that comprises an amino acid sequence that comprises a continuous portion of SEQ ID NO: 6 sufficient to permit the polypeptide to bind and stimulate wild-type human VEGFR-3.

5. The method of claim 1, wherein the VEGF-D protein comprises amino acids 93-201 of SEQ ID NO: 6.

6. The method according to claim 5, wherein the polynucleotide further includes a nucleotide sequence encoding a secretory signal peptide fused in-frame with the nucleotide sequence encoding the VEGF-D protein.

7. The method according to claim 5, wherein the polynucleotide further includes a promoter and/or enhancer sequence operatively linked upstream of the nucleotide sequence that encodes the VEGF-D protein.

8. The method according to claim 6, wherein the polynucleotide further includes a promoter and/or enhancer sequence operatively linked upstream of the nucleotide sequence that encodes the secretory signal peptide and the VEGF-D protein.

9. The method according to claim 7, wherein the polynucleotide further includes a polyadenylation sequence operatively linked downstream of the nucleotide sequence that encodes the VEGF-D protein.

10. The method according to claim 8, wherein the polynucleotide further includes a polyadenylation sequence operatively linked downstream of the nucleotide sequence that encodes the secretory signal peptide and the VEGF-D protein.

11. The method according to claim 1, comprising administering a vector to the patient, wherein the vector comprises the polynucleotide.

12. The method according to claim 4, comprising administering a vector to the patient, wherein the vector comprises the polynucleotide.

13. The method according to claim 12, wherein the vector is a replication-deficient retroviral vector.

14. The method according to claim 12, wherein the vector is selected from the group consisting of replication-deficient lentivurus vectors, adeno-associated viral vectors, adenoviral vectors, and combinations thereof.

15. The method according to claim 12, wherein the vector further includes at least one sequence operatively linked to the polynucleotide selected from the group consisting of:
   a nucleotide sequence encoding a secretory signal peptide fused in-frame with the nucleotide sequence encoding the VEGF-D protein;
   a promoter and/or enhancer sequence operatively linked upstream of the nucleotide sequence that encodes the VEGF-D protein, or operatively linked upstream of the nucleotide sequence that encodes the secretory signal peptide and the VEGF-D protein; and
   a polyadenylation sequence operatively linked downstream of the nucleotide sequence that encodes the VEGF-D protein.

16. The method of claim 12, wherein said administering of said therapeutically effTective amount of said polynucleotide induces VEGFR-3 signaling in the lymphatic endothelia of the patient.

17. The method of claim 12, wherein said administering of said therapeutically effecTive amount of said polynucleotide reduces edema in a limb of said patient.

18. The method of claim 12, wherein said administering of said therapeutically effective amount of said polynucleotide reduces accumulation of lymph fluids in said patient.

19. The method of claim 12. wherein said polynucleotide is administered via intravenous injection.

20. The method of claim 12, wherein said polynucleotide is administered via intramuscular injection.

* * * * *

SEQUENCE LISTING

```
<160> NUMBER OF SEQ ID NOS: 32

<210> SEQ ID NO 1
<211> LENGTH: 4111
<212> TYPE: DNA
<213> ORGANISM: Homo sapiens
<220> FEATURE:
<221> NAME/KEY: misc_feature
<223> OTHER INFORMATION: Human Flt4 (VEGFR-3) long form cDNA
<220> FEATURE:
<221> NAME/KEY: CDS
<222> LOCATION: (20)..(4111)

<400> SEQUENCE: 1
ccacgcgcag cggccggag atg cag cgg ggc gcc gcg ctg tgc ctg cga ctg        52
                     Met Gln Arg Gly Ala Ala Leu Cys Leu Arg Leu
                     1               5                   10 tgg ctc tgc ctg gga ctc ctg gac ggc ctg gtg agt ggc tac tcc atg       100
Trp Leu Cys Leu Gly Leu Leu Asp Gly Leu Val Ser Gly Tyr Ser Met
                15                  20                  25 acc ccc ccg acc ttg aac atc acg gag gag tca cac gtc atc gac acc       148
Thr Pro Pro Thr Leu Asn Ile Thr Glu Glu Ser His Val Ile Asp Thr
            30                  35                  40 ggt gac agc ctg tcc atc tcc tgc agg gga cag cac ccc ctc gag tgg       196
Gly Asp Ser Leu Ser Ile Ser Cys Arg Gly Gln His Pro Leu Glu Trp
        45                  50                  55 gct tgg cca gga gct cag gag gcg cca gcc acc gga gac aag gac agc       244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc       292
Glu Asp Thr Gly Val Val Arg Asp Cys Glu Gly Thr Asp Ala Arg Pro
                80                  85                  90 tac tgc aag gtg ttg ctg ctg cac gag gta cat gcc aac gac aca ggc       340
```

```
                Tyr Cys Lys Val Leu Leu His Glu Val His Ala Asn Asp Thr Gly
                                 95                 100                 105 agc tac gtc tgc tac tac aag tac atc aag gca cgc atc gag ggc acc          388
Ser Tyr Val Cys Tyr Tyr Lys Tyr Ile Lys Ala Arg Ile Glu Gly Thr
        110                 115                 120 acg gcc gcc agc tcc tac gtg ttc gtg aga gac ttt gag cag cca ttc          436
Thr Ala Ala Ser Ser Tyr Val Phe Val Arg Asp Phe Glu Gln Pro Phe
    125                 130                 135 atc aac aag cct gac acg ctc ttg gtc aac agg aag gac gcc atg tgg          484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg          532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac          580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac          628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc          676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg          724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac          772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac          820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc          868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac          916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc          964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc         1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca         1060
Phe Ile Ser Val Glu Trp Leu Lys Gly Pro Ile Leu Glu Ala Thr Ala
            335                 340                 345 gga gac gag ctg gtg aag ctg ccc gtg aag ctg gcg gcg tac ccc ccg         1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac         1156
Pro Glu Phe Gln Trp Tyr Lys Asp Gly Lys Ala Leu Ser Gly Arg His
    365                 370                 375 agt cca cat gcc ctg gtg ctc aag gag gtg aca gag gcc agc aca ggc         1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac         1252
Thr Tyr Thr Leu Ala Leu Trp Asn Ser Ala Ala Gly Leu Arg Arg Asn
                400                 405                 410 atc agc ctg gag ctg gtg gtg aat gtg ccc ccc cag ata cat gag aag         1300
```

```
                Ile Ser Leu Glu Leu Val Val Asn Val Pro Pro Gln Ile His Glu Lys
                            415                 420                 425 gag gcc tcc tcc ccc agc atc tac tcg cgt cac agc cgc cag gcc ctc          1348
Glu Ala Ser Ser Pro Ser Ile Tyr Ser Arg His Ser Arg Gln Ala Leu
            430                 435                 440 acc tgc acg gcc tac ggg gtg ccc ctg cct ctc agc atc cag tgg cac          1396
Thr Cys Thr Ala Tyr Gly Val Pro Leu Pro Leu Ser Ile Gln Trp His
            445                 450                 455 tgg cgg ccc tgg aca ccc tgc aag atg ttt gcc cag cgt agt ctc cgg          1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg          1492
Arg Arg Gln Gln Gln Asp Leu Met Pro Gln Cys Arg Asp Trp Arg Ala
                480                 485                 490 gtg acc acg cag gat gcc gtg aac ccc atc gag agc ctg gac acc tgg          1540
Val Thr Thr Gln Asp Ala Val Asn Pro Ile Glu Ser Leu Asp Thr Trp
                495                 500                 505 acc gag ttt gtg gag gga aag aat aag act gtg agc aag ctg gtg atc          1588
Thr Glu Phe Val Glu Gly Lys Asn Lys Thr Val Ser Lys Leu Val Ile
                510                 515                 520 cag aat gcc aac gtg tct gcc atg tac aag tgt gtg gtc tcc aac aag          1636
Gln Asn Ala Asn Val Ser Ala Met Tyr Lys Cys Val Val Ser Asn Lys
525                 530                 535 gtg ggc cag gat gag cgg ctc atc tac ttc tat gtg acc acc atc ccc          1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc          1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat          1780
Gln Pro Val Leu Leu Ser Cys Gln Ala Asp Ser Tyr Lys Tyr Glu His
                575                 580                 585 ctg cgc tgg tac cgc ctc aac ctg tcc acg ctg cac gat gcg cac ggg          1828
Leu Arg Trp Tyr Arg Leu Asn Leu Ser Thr Leu His Asp Ala His Gly
                590                 595                 600 aac ccg ctt ctg ctc gac tgc aag aac gtg cat ctg ttc gcc acc cct          1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg          1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat          1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag          2020
Val Cys Glu Val Gln Asp Arg Arg Ser His Asp Lys His Cys His Lys
                655                 660                 665 aag tac ctg tcg gtg cag gcc ctg gaa gcc cct cgg ctc acg cag aac          2068
Lys Tyr Leu Ser Val Gln Ala Leu Glu Ala Pro Arg Leu Thr Gln Asn
                670                 675                 680 ttg acc gac ctc ctg gtg aac gtg agc gac tcg ctg gag atg cag tgc          2116
Leu Thr Asp Leu Leu Val Asn Val Ser Asp Ser Leu Glu Met Gln Cys
685                 690                 695 ttg gtg gcc gga gcg cac gcg ccc agc atc gtg tgg tac aaa gac gag          2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag          2212
Arg Leu Leu Glu Glu Lys Ser Gly Val Asp Leu Ala Asp Ser Asn Gln
                720                 725                 730 aag ctg agc atc cag cgc gtg cgc gag gag gat gcg gga cgc tat ctg          2260
```

-continued

```
                Lys Leu Ser Ile Gln Arg Val Arg Glu Glu Asp Ala Gly Arg Tyr Leu
                                735                 740                 745 tgc agc gtg tgc aac gcc aag ggc tgc gtc aac tcc tcc gcc agc gtg         2308
Cys Ser Val Cys Asn Ala Lys Gly Cys Val Asn Ser Ser Ala Ser Val
            750                 755                 760 gcc gtg gaa ggc tcc gag gat aag ggc agc atg gag atc gtg atc ctt         2356
Ala Val Glu Gly Ser Glu Asp Lys Gly Ser Met Glu Ile Val Ile Leu
        765                 770                 775 gtc ggt acc ggc gtc atc gct gtc ttc ttc tgg gtc ctc ctc ctc             2404
Val Gly Thr Gly Val Ile Ala Val Phe Phe Trp Val Leu Leu Leu Leu
780                 785                 790                 795 atc ttc tgt aac atg agg agg ccg gcc cac gca gac atc aag acg ggc         2452
Ile Phe Cys Asn Met Arg Arg Pro Ala His Ala Asp Ile Lys Thr Gly
                800                 805                 810 tac ctg tcc atc atc atg gac ccc ggg gag gtg cct ctg gag gag caa         2500
Tyr Leu Ser Ile Ile Met Asp Pro Gly Glu Val Pro Leu Glu Glu Gln
            815                 820                 825 tgc gaa tac ctg tcc tac gat gcc agc cag tgg gaa ttc ccc cga gag         2548
Cys Glu Tyr Leu Ser Tyr Asp Ala Ser Gln Trp Glu Phe Pro Arg Glu
        830                 835                 840 cgg ctg cac ctg ggg aga gtg ctc ggc tac ggc gcc ttc ggg aag gtg         2596
Arg Leu His Leu Gly Arg Val Leu Gly Tyr Gly Ala Phe Gly Lys Val
    845                 850                 855 gtg gaa gcc tcc gct ttc ggc atc cac aag ggc agc agc tgt gac acc         2644
Val Glu Ala Ser Ala Phe Gly Ile His Lys Gly Ser Ser Cys Asp Thr
860                 865                 870                 875 gtg gcc gtg aaa atg ctg aaa gag ggc gcc acg gcc agc gag cac cgc         2692
Val Ala Val Lys Met Leu Lys Glu Gly Ala Thr Ala Ser Glu His Arg
                880                 885                 890 gcg ctg atg tcg gag ctc aag atc ctc att cac atc ggc aac cac ctc         2740
Ala Leu Met Ser Glu Leu Lys Ile Leu Ile His Ile Gly Asn His Leu
            895                 900                 905 aac gtg gtc aac ctc ctc ggg gcg tgc acc aag ccg cag ggc ccc ctc         2788
Asn Val Val Asn Leu Leu Gly Ala Cys Thr Lys Pro Gln Gly Pro Leu
        910                 915                 920 atg gtg atc gtg gag ttc tgc aag tac ggc aac ctc tcc aac ttc ctg         2836
Met Val Ile Val Glu Phe Cys Lys Tyr Gly Asn Leu Ser Asn Phe Leu
    925                 930                 935 cgc gcc aag cgg gac gcc ttc agc ccc tgc gcg gag aag tct ccc gag         2884
Arg Ala Lys Arg Asp Ala Phe Ser Pro Cys Ala Glu Lys Ser Pro Glu
940                 945                 950                 955 cag cgc gga cgc ttc cgc gcc atg gtg gag ctc gcc agg ctg gat cgg         2932
Gln Arg Gly Arg Phe Arg Ala Met Val Glu Leu Ala Arg Leu Asp Arg
                960                 965                 970 agg cgg ccg ggg agc agc gac agg gtc ctc ttc gcg cgg ttc tcg aag         2980
Arg Arg Pro Gly Ser Ser Asp Arg Val Leu Phe Ala Arg Phe Ser Lys
            975                 980                 985 acc gag ggc gga gcg agg cgg gct tct cca gac caa gaa  gct gag gac        3028
Thr Glu Gly Gly Ala Arg Arg Ala Ser Pro Asp Gln Glu  Ala Glu Asp
        990                 995                 1000 ctg tgg ctg agc ccg ctg acc  atg gaa gat ctt gtc  tgc tac agc           3073
Leu Trp Leu Ser Pro Leu Thr  Met Glu Asp Leu Val  Cys Tyr Ser
    1005                 1010                 1015 ttc cag gtg gcc aga ggg atg  gag ttc ctg gct tcc  cga aag tgc           3118
Phe Gln Val Ala Arg Gly Met  Glu Phe Leu Ala Ser  Arg Lys Cys
    1020                 1025                 1030 atc cac aga gac ctg gct gct  cgg aac att ctg ctg  tcg gaa agc           3163
Ile His Arg Asp Leu Ala Ala  Arg Asn Ile Leu Leu  Ser Glu Ser
    1035                 1040                 1045 gac gtg gtg aag atc tgt gac  ttt ggc ctt gcc cgg  gac atc tac           3208
```

```
           Asp Val Val Lys Ile Cys Asp Phe Gly Leu Ala Arg Asp Ile Tyr
               1050                1055                1060 aaa gac cct gac tac gtc cgc aag ggc agt gcc cgg ctg ccc ctg        3253
Lys Asp Pro Asp Tyr Val Arg Lys Gly Ser Ala Arg Leu Pro Leu
1065                1070                1075 aag tgg atg gcc cct gaa agc atc ttc gac aag gtg tac acc acg        3298
Lys Trp Met Ala Pro Glu Ser Ile Phe Asp Lys Val Tyr Thr Thr
    1080                1085                1090 cag agt gac gtg tgg tcc ttt ggg gtg ctt ctc tgg gag atc ttc        3343
Gln Ser Asp Val Trp Ser Phe Gly Val Leu Leu Trp Glu Ile Phe
1095                1100                1105 tct ctg ggg gcc tcc ccg tac cct ggg gtg cag atc aat gag gag        3388
Ser Leu Gly Ala Ser Pro Tyr Pro Gly Val Gln Ile Asn Glu Glu
1110                1115                1120 ttc tgc cag cgg ctg aga gac ggc aca agg atg agg gcc ccg gag        3433
Phe Cys Gln Arg Leu Arg Asp Gly Thr Arg Met Arg Ala Pro Glu
    1125                1130                1135 ctg gcc act ccc gcc ata cgc cgc atc atg ctg aac tgc tgg tcc        3478
Leu Ala Thr Pro Ala Ile Arg Arg Ile Met Leu Asn Cys Trp Ser
1140                1145                1150 gga gac ccc aag gcg aga cct gca ttc tcg gag ctg gtg gag atc        3523
Gly Asp Pro Lys Ala Arg Pro Ala Phe Ser Glu Leu Val Glu Ile
    1155                1160                1165 ctg ggg gac ctg ctc cag ggc agg ggc ctg caa gag gaa gag gag        3568
Leu Gly Asp Leu Leu Gln Gly Arg Gly Leu Gln Glu Glu Glu Glu
1170                1175                1180 gtc tgc atg gcc ccg cgc agc tct cag agc tca gaa gag ggc agc        3613
Val Cys Met Ala Pro Arg Ser Ser Gln Ser Ser Glu Glu Gly Ser
1185                1190                1195 ttc tcg cag gtg tcc acc atg gcc cta cac atc gcc cag gct gac        3658
Phe Ser Gln Val Ser Thr Met Ala Leu His Ile Ala Gln Ala Asp
    1200                1205                1210 gct gag gac agc ccg cca agc ctg cag cgc cac agc ctg gcc gcc        3703
Ala Glu Asp Ser Pro Pro Ser Leu Gln Arg His Ser Leu Ala Ala
1215                1220                1225 agg tat tac aac tgg gtg tcc ttt ccc ggg tgc ctg gcc aga ggg        3748
Arg Tyr Tyr Asn Trp Val Ser Phe Pro Gly Cys Leu Ala Arg Gly
    1230                1235                1240 gct gag acc cgt ggt tcc tcc agg atg aag aca ttt gag gaa ttc        3793
Ala Glu Thr Arg Gly Ser Ser Arg Met Lys Thr Phe Glu Glu Phe
1245                1250                1255 ccc atg acc cca acg acc tac aaa ggc tct gtg gac aac cag aca        3838
Pro Met Thr Pro Thr Thr Tyr Lys Gly Ser Val Asp Asn Gln Thr
    1260                1265                1270 gac agt ggg atg gtg ctg gcc tcg gag gag ttt gag cag ata gag        3883
Asp Ser Gly Met Val Leu Ala Ser Glu Glu Phe Glu Gln Ile Glu
1275                1280                1285 agc agg cat aga caa gaa agc ggc ttc agc tgt aaa gga cct ggc        3928
Ser Arg His Arg Gln Glu Ser Gly Phe Ser Cys Lys Gly Pro Gly
1290                1295                1300 cag aat gtg gct gtg acc agg gca cac cct gac tcc caa ggg agg        3973
Gln Asn Val Ala Val Thr Arg Ala His Pro Asp Ser Gln Gly Arg
1305                1310                1315 cgg cgg cgg cct gag cgg ggg gcc cga gga ggc cag gtg ttt tac        4018
Arg Arg Arg Pro Glu Arg Gly Ala Arg Gly Gly Gln Val Phe Tyr
    1320                1325                1330 aac agc gag tat ggg gag ctg tcg gag cca agc gag gag gac cac        4063
Asn Ser Glu Tyr Gly Glu Leu Ser Glu Pro Ser Glu Glu Asp His
1335                1340                1345 tgc tcc ccg tct gcc cgc gtg act ttc ttc aca gac aac agc tac        4108
```

```
Cys Ser Pro Ser Ala Arg Val Thr Phe Phe Thr Asp Asn Ser Tyr
    1350                1355                1360 taa                                                                    4111
```

<210> SEQ ID NO 2
<211> LENGTH: 1363
<212> TYPE: PRT
<213> ORGANISM: Homo sapiens

<400> SEQUENCE: 2

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350
```

-continued

```
Lys Leu Pro Val Lys Leu Ala Ala Tyr Pro Pro Glu Phe Gln Trp
        355                 360                 365
Tyr Lys Asp Gly Lys Ala Leu Ser Gly Arg His Ser Pro His Ala Leu
    370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Pro Gln Ile His Glu Lys Glu Ala Ser Ser Pro
                420                 425                 430
Ser Ile Tyr Ser Arg His Ser Arg Gln Ala Leu Thr Cys Thr Ala Tyr
            435                 440                 445
Gly Val Pro Leu Pro Leu Ser Ile Gln Trp His Trp Arg Pro Trp Thr
        450                 455                 460
Pro Cys Lys Met Phe Ala Gln Arg Ser Leu Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
                500                 505                 510
Gly Lys Asn Lys Thr Val Ser Lys Leu Val Ile Gln Asn Ala Asn Val
            515                 520                 525
Ser Ala Met Tyr Lys Cys Val Val Ser Asn Lys Val Gly Gln Asp Glu
    530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
            580                 585                 590
Leu Asn Leu Ser Thr Leu His Asp Ala His Gly Asn Pro Leu Leu Leu
        595                 600                 605
Asp Cys Lys Asn Val His Leu Phe Ala Thr Pro Leu Ala Ala Ser Leu
    610                 615                 620
Glu Glu Val Ala Pro Gly Ala Arg His Ala Thr Leu Ser Leu Ser Ile
625                 630                 635                 640
Pro Arg Val Ala Pro Glu His Glu Gly His Tyr Val Cys Glu Val Gln
                645                 650                 655
Asp Arg Arg Ser His Asp Lys His Cys His Lys Lys Tyr Leu Ser Val
            660                 665                 670
Gln Ala Leu Glu Ala Pro Arg Leu Thr Gln Asn Leu Thr Asp Leu Leu
        675                 680                 685
Val Asn Val Ser Asp Ser Leu Glu Met Gln Cys Leu Val Ala Gly Ala
    690                 695                 700
His Ala Pro Ser Ile Val Trp Tyr Lys Asp Glu Arg Leu Leu Glu Glu
705                 710                 715                 720
Lys Ser Gly Val Asp Leu Ala Asp Ser Asn Gln Lys Leu Ser Ile Gln
                725                 730                 735
Arg Val Arg Glu Glu Asp Ala Gly Arg Tyr Leu Cys Ser Val Cys Asn
            740                 745                 750
Ala Lys Gly Cys Val Asn Ser Ser Ala Ser Val Ala Val Glu Gly Ser
        755                 760                 765
Glu Asp Lys Gly Ser Met Glu Ile Val Ile Leu Val Gly Thr Gly Val
    770                 775                 780
```

```
Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
        820                 825                 830

Tyr Asp Ala Ser Gln Trp Glu Phe Pro Arg Glu Arg Leu His Leu Gly
        835                 840                 845

Arg Val Leu Gly Tyr Gly Ala Phe Gly Lys Val Val Glu Ala Ser Ala
    850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
            995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Val Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140

Ile Arg Arg Ile Met Leu Asn Cys Trp Ser Gly Asp Pro Lys Ala
    1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Glu Val Cys Met Ala Pro
    1175                1180                1185
```

```
Arg Ser  Ser Gln Ser Ser  Glu Glu Gly Ser  Phe Ser Gln Val Ser
    1190         1195              1200

Thr Met  Ala Leu His Ile  Ala Gln Ala Asp  Ala Glu Asp Ser Pro
    1205         1210              1215

Pro Ser  Leu Gln Arg His  Ser Leu Ala Ala  Arg Tyr Tyr Asn Trp
    1220         1225              1230

Val Ser  Phe Pro Gly Cys  Leu Ala Arg Gly  Ala Glu Thr Arg Gly
    1235         1240              1245

Ser Ser  Arg Met Lys Thr  Phe Glu Glu Phe  Pro Met Thr Pro Thr
    1250         1255              1260

Thr Tyr  Lys Gly Ser Val  Asp Asn Gln Thr  Asp Ser Gly Met Val
    1265         1270              1275

Leu Ala  Ser Glu Glu Phe  Glu Gln Ile Glu  Ser Arg His Arg Gln
    1280         1285              1290

Glu Ser  Gly Phe Ser Cys  Lys Gly Pro Gly  Gln Asn Val Ala Val
    1295         1300              1305

Thr Arg  Ala His Pro Asp  Ser Gln Gly Arg  Arg Arg Arg Pro Glu
    1310         1315              1320

Arg Gly  Ala Arg Gly Gly  Gln Val Phe Tyr  Asn Ser Glu Tyr Gly
    1325         1330              1335

Glu Leu  Ser Glu Pro Ser  Glu Glu Asp His  Cys Ser Pro Ser Ala
    1340         1345              1350

Arg Val  Thr Phe Phe Thr  Asp Asn Ser Tyr
    1355         1360
```

<210> SEQ ID NO 3
<211> LENGTH: 1997
<212> TYPE: DNA
<213> ORGANISM: Homo sapiens
<220> FEATURE:
<221> NAME/KEY: misc_feature
<223> OTHER INFORMATION: Human cDNA for prepro-VEGF-C
<220> FEATURE:
<221> NAME/KEY: CDS
<222> LOCATION: (352)..(1611)

<400> SEQUENCE: 3

```
cccgccccgc ctctccaaaa agctacaccg acgcggaccg cggcggcgtc ctccctcgcc    60
ctcgcttcac ctcgcgggct ccgaatgcgg ggagctcgga tgtccggttt cctgtgaggc   120
ttttacctga cacccgccgc ctttccccgg cactggctgg gagggcgccc tgcaaagttg   180
ggaacgcgga gccccggacc cgctcccgcc gcctccggct cgcccagggg gggtcgccgg   240
gaggagcccg ggggagaggg accaggaggg gcccgcggcc tcgcaggggc gcccgcgccc   300 ccaccctgc  ccccgccagc ggaccggtcc cccacccccg gtccttccac c atg cac   357
                                                         Met His
                                                           1 ttg ctg ggc ttc ttc tct gtg gcg tgt tct ctg ctc gcc gct gcg ctg    405
Leu Leu Gly Phe Phe Ser Val Ala Cys Ser Leu Leu Ala Ala Ala Leu
          5                  10                  15 ctc ccg ggt cct cgc gag gcg ccc gcc gcc gcc gcc gcc ttc gag tcc    453
Leu Pro Gly Pro Arg Glu Ala Pro Ala Ala Ala Ala Ala Phe Glu Ser
 20                  25                  30 gga ctc gac ctc tcg gac gcg gag ccc gac gcg ggc gag gcc acg gct    501
Gly Leu Asp Leu Ser Asp Ala Glu Pro Asp Ala Gly Glu Ala Thr Ala
 35                  40                  45                  50 tat gca agc aaa gat ctg gag gag cag tta cgg tct gtg tcc agt gta    549
Tyr Ala Ser Lys Asp Leu Glu Glu Gln Leu Arg Ser Val Ser Ser Val
              55                  60                  65
```

```
gat gaa ctc atg act gta ctc tac cca gaa tat tgg aaa atg tac aag        597
Asp Glu Leu Met Thr Val Leu Tyr Pro Glu Tyr Trp Lys Met Tyr Lys
         70              75              80 tgt cag cta agg aaa gga ggc tgg caa cat aac aga gaa cag gcc aac        645
Cys Gln Leu Arg Lys Gly Gly Trp Gln His Asn Arg Glu Gln Ala Asn
     85              90              95 ctc aac tca agg aca gaa gag act ata aaa ttt gct gca gca cat tat        693
Leu Asn Ser Arg Thr Glu Glu Thr Ile Lys Phe Ala Ala Ala His Tyr
100             105             110 aat aca gag atc ttg aaa agt att gat aat gag tgg aga aag act caa        741
Asn Thr Glu Ile Leu Lys Ser Ile Asp Asn Glu Trp Arg Lys Thr Gln
115             120             125             130 tgc atg cca cgg gag gtg tgt ata gat gtg ggg aag gag ttt gga gtc        789
Cys Met Pro Arg Glu Val Cys Ile Asp Val Gly Lys Glu Phe Gly Val
             135             140             145 gcg aca aac acc ttc ttt aaa cct cca tgt gtg tcc gtc tac aga tgt        837
Ala Thr Asn Thr Phe Phe Lys Pro Pro Cys Val Ser Val Tyr Arg Cys
         150             155             160 ggg ggt tgc tgc aat agt gag ggg ctg cag tgc atg aac acc agc acg        885
Gly Gly Cys Cys Asn Ser Glu Gly Leu Gln Cys Met Asn Thr Ser Thr
         165             170             175 agc tac ctc agc aag acg tta ttt gaa att aca gtg cct ctc tct caa        933
Ser Tyr Leu Ser Lys Thr Leu Phe Glu Ile Thr Val Pro Leu Ser Gln
180             185             190 ggc ccc aaa cca gta aca atc agt ttt gcc aat cac act tcc tgc cga        981
Gly Pro Lys Pro Val Thr Ile Ser Phe Ala Asn His Thr Ser Cys Arg
195             200             205             210 tgc atg tct aaa ctg gat gtt tac aga caa gtt cat tcc att att aga       1029
Cys Met Ser Lys Leu Asp Val Tyr Arg Gln Val His Ser Ile Ile Arg
             215             220             225 cgt tcc ctg cca gca aca cta cca cag tgt cag gca gcg aac aag acc       1077
Arg Ser Leu Pro Ala Thr Leu Pro Gln Cys Gln Ala Ala Asn Lys Thr
         230             235             240 tgc ccc acc aat tac atg tgg aat aat cac atc tgc aga tgc ctg gct       1125
Cys Pro Thr Asn Tyr Met Trp Asn Asn His Ile Cys Arg Cys Leu Ala
         245             250             255 cag gaa gat ttt atg ttt tcc tcg gat gct gga gat gac tca aca gat       1173
Gln Glu Asp Phe Met Phe Ser Ser Asp Ala Gly Asp Asp Ser Thr Asp
260             265             270 gga ttc cat gac atc tgt gga cca aac aag gag ctg gat gaa gag acc       1221
Gly Phe His Asp Ile Cys Gly Pro Asn Lys Glu Leu Asp Glu Glu Thr
275             280             285             290 tgt cag tgt gtc tgc aga gcg ggg ctt cgg cct gcc agc tgt gga ccc       1269
Cys Gln Cys Val Cys Arg Ala Gly Leu Arg Pro Ala Ser Cys Gly Pro
             295             300             305 cac aaa gaa cta gac aga aac tca tgc cag tgt gtc tgt aaa aac aaa       1317
His Lys Glu Leu Asp Arg Asn Ser Cys Gln Cys Val Cys Lys Asn Lys
         310             315             320 ctc ttc ccc agc caa tgt ggg gcc aac cga gaa ttt gat gaa aac aca       1365
Leu Phe Pro Ser Gln Cys Gly Ala Asn Arg Glu Phe Asp Glu Asn Thr
         325             330             335 tgc cag tgt gta tgt aaa aga acc tgc ccc aga aat caa ccc cta aat       1413
Cys Gln Cys Val Cys Lys Arg Thr Cys Pro Arg Asn Gln Pro Leu Asn
340             345             350 cct gga aaa tgt gcc tgt gaa tgt aca gaa agt cca cag aaa tgc ttg       1461
Pro Gly Lys Cys Ala Cys Glu Cys Thr Glu Ser Pro Gln Lys Cys Leu
355             360             365             370 tta aaa gga aag aag ttc cac cac caa aca tgc agc tgt tac aga cgg       1509
Leu Lys Gly Lys Lys Phe His His Gln Thr Cys Ser Cys Tyr Arg Arg
             375             380             385
```

```
cca tgt acg aac cgc cag aag gct tgt gag cca gga ttt tca tat agt    1557
Pro Cys Thr Asn Arg Gln Lys Ala Cys Glu Pro Gly Phe Ser Tyr Ser
            390                 395                 400 gaa gaa gtg tgt cgt tgt gtc cct tca tat tgg aaa aga cca caa atg    1605
Glu Glu Val Cys Arg Cys Val Pro Ser Tyr Trp Lys Arg Pro Gln Met
        405                 410                 415 agc taa gattgtactg ttttccagtt catcgatttt ctattatgga aaactgtgtt    1661
Ser gccacagtag aactgtctgt gaacagagag acccttgtgg gtccatgcta acaaagacaa    1721
aagtctgtct ttcctgaacc atgtggataa ctttacagaa atggactgga gctcatctgc    1781
aaaaggcctc ttgtaaagac tggttttctg ccaatgacca aacagccaag attttcctct    1841
tgtgatttct ttaaaagaat gactatataa tttatttcca ctaaaaatat tgtttctgca    1901 ttcatttta tagcaacaac aattggtaaa actcactgtg atcaatattt ttatatcatg    1961
caaaatatgt ttaaaataaa atgaaaattg tattat    1997

<210> SEQ ID NO 4
<211> LENGTH: 419
<212> TYPE: PRT
<213> ORGANISM: Homo sapiens

<400> SEQUENCE: 4

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
        35                  40                  45

Thr Ala Tyr Ala Ser Lys Asp Leu Glu Glu Gln Leu Arg Ser Val Ser
    50                  55                  60

Ser Val Asp Glu Leu Met Thr Val Leu Tyr Pro Glu Tyr Trp Lys Met
65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255
```

```
Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
                275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
    340                 345                 350

Leu Asn Pro Gly Lys Cys Ala Cys Glu Cys Thr Glu Ser Pro Gln Lys
                355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 5
<211> LENGTH: 2029
<212> TYPE: DNA
<213> ORGANISM: Homo sapiens
<220> FEATURE:
<221> NAME/KEY: misc_feature
<223> OTHER INFORMATION: Human prepro-VEGF-C cDNA
<220> FEATURE:
<221> NAME/KEY: CDS
<222> LOCATION: (411)..(1475)

<400> SEQUENCE: 5
gttgggttcc agctttctgt agctgtaagc attggtggcc acaccacctc cttacaaagc      60
aactagaacc tgcggcatac attggagaga ttttttttaat tttctggaca tgaagtaaat    120
ttagagtgct ttctaatttc aggtagaaga catgtccacc ttctgattat ttttggagaa    180
cattttgatt tttttcatct ctctctcccc accctaagaa ttgtgcaaaa aaagcgtacc    240
ttgcctaatt gaataatttt cattggattt tgatcagaac tgattatttg gttttctgtg    300
tgaagttttg aggtttcaaa cttccttcct ggagaatgcc ttttgaaaca attttctcta    360
gctgcctgat gtcaactgct tagtaatcag tggatattga atattcaaa atg tac        416
                                                       Met Tyr
                                                         1 aga gag tgg gta gtg gtg aat gtt ttc atg atg ttg tac gtc cag ctg      464
Arg Glu Trp Val Val Val Asn Val Phe Met Met Leu Tyr Val Gln Leu
       5                  10                  15 gtg cag ggc tcc agt aat gaa cat gga cca gtg aag cga tca tct cag      512
Val Gln Gly Ser Ser Asn Glu His Gly Pro Val Lys Arg Ser Ser Gln
    20                  25                  30 tcc aca ttg gaa cga tct gaa cag cag atc agg gct gct tct agt ttg      560
Ser Thr Leu Glu Arg Ser Glu Gln Gln Ile Arg Ala Ala Ser Ser Leu
35                  40                  45                  50 gag gaa cta ctt cga att act cac tct gag gac tgg aag ctg tgg aga      608
Glu Glu Leu Leu Arg Ile Thr His Ser Glu Asp Trp Lys Leu Trp Arg
                55                  60                  65
```

| | |
|---|---|
| tgc agg ctg agg ctc aaa agt ttt acc agt atg gac tct cgc tca gca<br>Cys Arg Leu Arg Leu Lys Ser Phe Thr Ser Met Asp Ser Arg Ser Ala<br>          70                  75                       80 | 656 |
| tcc cat cgg tcc act agg ttt gcg gca act ttc tat gac att gaa aca<br>Ser His Arg Ser Thr Arg Phe Ala Ala Thr Phe Tyr Asp Ile Glu Thr<br>        85                    90                      95 | 704 |
| cta aaa gtt ata gat gaa gaa tgg caa aga act cag tgc agc cct aga<br>Leu Lys Val Ile Asp Glu Glu Trp Gln Arg Thr Gln Cys Ser Pro Arg<br>      100                    105                   110 | 752 |
| gaa acg tgc gtg gag gtg gcc agt gag ctg ggg aag agt acc aac aca<br>Glu Thr Cys Val Glu Val Ala Ser Glu Leu Gly Lys Ser Thr Asn Thr<br>115                      120                   125                130 | 800 |
| ttc ttc aag ccc cct tgt gtg aac gtg ttc cga tgt ggt ggc tgt tgc<br>Phe Phe Lys Pro Pro Cys Val Asn Val Phe Arg Cys Gly Gly Cys Cys<br>                  135                   140                145 | 848 |
| aat gaa gag agc ctt atc tgt atg aac acc agc acc tcg tac att tcc<br>Asn Glu Glu Ser Leu Ile Cys Met Asn Thr Ser Thr Ser Tyr Ile Ser<br>              150                   155                 160 | 896 |
| aaa cag ctc ttt gag ata tca gtg cct ttg aca tca gta cct gaa tta<br>Lys Gln Leu Phe Glu Ile Ser Val Pro Leu Thr Ser Val Pro Glu Leu<br>           165                  170                 175 | 944 |
| gtg cct gtt aaa gtt gcc aat cat aca ggt tgt aag tgc ttg cca aca<br>Val Pro Val Lys Val Ala Asn His Thr Gly Cys Lys Cys Leu Pro Thr<br>180                      185                   190 | 992 |
| gcc ccc cgc cat cca tac tca att atc aga aga tcc atc cag atc cct<br>Ala Pro Arg His Pro Tyr Ser Ile Ile Arg Arg Ser Ile Gln Ile Pro<br>195                      200                   205                210 | 1040 |
| gaa gaa gat cgc tgt tcc cat tcc aag aaa ctc tgt cct att gac atg<br>Glu Glu Asp Arg Cys Ser His Ser Lys Lys Leu Cys Pro Ile Asp Met<br>                215                   220                 225 | 1088 |
| cta tgg gat agc aac aaa tgt aaa tgt gtt ttg cag gag gaa aat cca<br>Leu Trp Asp Ser Asn Lys Cys Lys Cys Val Leu Gln Glu Glu Asn Pro<br>              230                   235                 240 | 1136 |
| ctt gct gga aca gaa gac cac tct cat ctc cag gaa cca gct ctc tgt<br>Leu Ala Gly Thr Glu Asp His Ser His Leu Gln Glu Pro Ala Leu Cys<br>            245                   250                 255 | 1184 |
| ggg cca cac atg atg ttt gac gaa gat cgt tgc gag tgt gtc tgt aaa<br>Gly Pro His Met Met Phe Asp Glu Asp Arg Cys Glu Cys Val Cys Lys<br>260                      265                   270 | 1232 |
| aca cca tgt ccc aaa gat cta atc cag cac ccc aaa aac tgc agt tgc<br>Thr Pro Cys Pro Lys Asp Leu Ile Gln His Pro Lys Asn Cys Ser Cys<br>275                      280                   285                290 | 1280 |
| ttt gag tgc aaa gaa agt ctg gag acc tgc tgc cag aag cac aag cta<br>Phe Glu Cys Lys Glu Ser Leu Glu Thr Cys Cys Gln Lys His Lys Leu<br>                295                   300                 305 | 1328 |
| ttt cac cca gac acc tgc agc tgt gag gac aga tgc ccc ttt cat acc<br>Phe His Pro Asp Thr Cys Ser Cys Glu Asp Arg Cys Pro Phe His Thr<br>              310                   315                 320 | 1376 |
| aga cca tgt gca agt ggc aaa aca gca tgt gca aag cat tgc cgc ttt<br>Arg Pro Cys Ala Ser Gly Lys Thr Ala Cys Ala Lys His Cys Arg Phe<br>            325                   330                 335 | 1424 |
| cca aag gag aaa agg gct gcc cag ggg ccc cac agc cga aag aat cct<br>Pro Lys Glu Lys Arg Ala Ala Gln Gly Pro His Ser Arg Lys Asn Pro<br>340                      345                   350 | 1472 |
| tga ttcagcgttc caagttcccc atccctgtca tttttaacag catgctgctt | 1525 |
| tgccaagttg ctgtcactgt ttttttccca ggtgttaaaa aaaaaatcca ttttacacag | 1585 |
| caccacagtg aatccagacc aaccttccat tcacaccagc taaggagtcc ctggttcatt | 1645 |
| gatggatgtc ttctagctgc agatgcctct gcgcaccaag gaatggagag gaggggaccc | 1705 |

-continued

```
atgtaatcct tttgtttagt tttgttttg ttttttggtg aatgagaaag gtgtgctggt    1765
catggaatgg caggtgtcat atgactgatt actcagagca gatgaggaaa actgtagtct    1825
ctgagtcctt tgctaatcgc aactcttgtg aattattctg attcttttt atgcagaatt    1885 tgattcgtat gatcagtact gactttctga ttactgtcca gcttatagtc ttccagttta    1945
atgaactacc atctgatgtt tcatatttaa gtgtatttaa agaaataaa caccattatt    2005 caagccaaaa aaaaaaaaaa aaaa                                            2029
```

<210> SEQ ID NO 6
<211> LENGTH: 354
<212> TYPE: PRT
<213> ORGANISM: Homo sapiens

<400> SEQUENCE: 6

```
Met Tyr Arg Glu Trp Val Val Asn Val Phe Met Met Leu Tyr Val
 1               5                  10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320
```

```
His Thr Arg Pro Cys Ala Ser Gly Lys Thr Ala Cys Ala Lys His Cys
            325                 330                 335

Arg Phe Pro Lys Glu Lys Arg Ala Ala Gln Gly Pro His Ser Arg Lys
            340                 345                 350

Asn Pro

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 7
tcaccatcga tccaagc                                                    17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 8
agttctgcgt gagccgag                                                   18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 9
caggacgggg tgacttga                                                   18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 10
gcccaggcct gtctactg                                                   18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 11
ccagctccta cgtgttcg                                                   18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 12
ggcaacagct ggatgtca                                                   18
```

```
<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 13
ctgtgagggc gtgggagt                                                 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 14
gtcctttgag ccactgga                                                 18

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 15
cacacgtcat cgacaccggt g                                             21

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 16
ggcaacagct ggatgtca                                                 18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
cctgagtatc tcccgcgtcg c                                             21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
ggtgcctccc tgtaccctgg g                                             21

<210> SEQ ID NO 19
<211> LENGTH: 1363
<212> TYPE: PRT
<213> ORGANISM: Mus musculus
```

<400> SEQUENCE: 19

```
Met Gln Pro Gly Ala Ala Leu Asn Leu Arg Leu Trp Leu Cys Leu Gly
1               5                   10                  15
Leu Leu Gln Gly Leu Ala Asn Gly Tyr Ser Met Thr Pro Pro Thr Leu
            20                  25                  30
Asn Ile Thr Glu Asp Ser Tyr Val Ile Asp Thr Gly Asp Ser Leu Ser
        35                  40                  45
Ile Ser Cys Arg Gly Gln His Pro Leu Glu Trp Thr Trp Pro Gly Ala
    50                  55                  60
Gln Glu Val Leu Thr Thr Gly Gly Lys Asp Ser Glu Asp Thr Arg Val
65                  70                  75                  80
Val His Asp Cys Glu Gly Thr Glu Ala Arg Pro Tyr Cys Lys Val Leu
                85                  90                  95
Leu Leu Ala Gln Thr His Ala Asn Asn Thr Gly Ser Tyr His Cys Tyr
            100                 105                 110
Tyr Lys Tyr Ile Lys Ala Arg Ile Glu Gly Thr Thr Ala Ala Ser Thr
        115                 120                 125
Tyr Val Phe Val Arg Asp Phe Lys His Pro Phe Ile Asn Lys Pro Asp
    130                 135                 140
Thr Leu Leu Val Asn Arg Lys Asp Ser Met Trp Val Pro Cys Leu Val
145                 150                 155                 160
Ser Ile Pro Gly Leu Asn Ile Thr Leu Arg Ser Gln Ser Ser Ala Leu
                165                 170                 175
His Pro Asp Gly Gln Glu Val Leu Trp Asp Asp Arg Arg Gly Met Arg
            180                 185                 190
Val Pro Thr Gln Leu Leu Arg Asp Ala Leu Tyr Leu Gln Cys Glu Thr
        195                 200                 205
Thr Trp Gly Asp Gln Asn Phe Leu Ser Asn Leu Phe Val Val His Ile
    210                 215                 220
Thr Gly Asn Glu Leu Tyr Asp Ile Gln Leu Tyr Pro Lys Lys Ser Met
225                 230                 235                 240
Glu Leu Leu Val Gly Glu Lys Leu Val Leu Asn Cys Thr Val Trp Ala
                245                 250                 255
Glu Phe Asp Ser Gly Val Thr Phe Asp Trp Asp Tyr Pro Gly Lys Gln
            260                 265                 270
Ala Glu Arg Ala Lys Trp Val Pro Glu Arg Arg Ser Gln Gln Thr His
        275                 280                 285
Thr Glu Leu Ser Ser Ile Leu Thr Ile His Asn Val Ser Gln Asn Asp
    290                 295                 300
Leu Gly Pro Tyr Val Cys Glu Ala Asn Asn Gly Ile Gln Arg Phe Arg
305                 310                 315                 320
Glu Ser Thr Glu Val Ile Val His Glu Lys Pro Phe Ile Ser Val Glu
                325                 330                 335
Trp Leu Lys Gly Pro Val Leu Glu Ala Thr Ala Gly Asp Glu Leu Val
            340                 345                 350
Lys Leu Pro Val Lys Leu Ala Ala Tyr Pro Pro Pro Glu Phe Gln Trp
        355                 360                 365
Tyr Lys Asp Arg Lys Ala Val Thr Gly Arg His Asn Pro His Ala Leu
    370                 375                 380
Val Leu Lys Glu Val Thr Glu Ala Ser Ala Gly Val Tyr Thr Leu Ala
385                 390                 395                 400
Leu Trp Asn Ser Ala Ala Gly Leu Arg Gln Asn Ile Ser Leu Glu Leu
                405                 410                 415
```

-continued

Val Val Asn Val Pro Pro His Ile His Glu Lys Glu Ala Ser Ser Pro
            420                 425                 430

Ser Ile Tyr Ser Arg His Ser Arg Gln Thr Leu Thr Cys Thr Ala Tyr
            435                 440                 445

Gly Val Pro Gln Pro Leu Ser Val Gln Trp His Trp Arg Pro Trp Thr
        450                 455                 460

Pro Cys Lys Thr Phe Ala Gln Arg Ser Leu Arg Arg Gln Gln Arg
465                 470                 475                 480

Asp Gly Met Pro Gln Cys Arg Asp Trp Lys Glu Val Thr Thr Gln Asp
                485                 490                 495

Ala Val Asn Pro Ile Glu Ser Leu Asp Ser Trp Thr Glu Phe Val Glu
            500                 505                 510

Gly Lys Asn Lys Thr Val Ser Lys Leu Val Ile Gln Asp Ala Asn Val
            515                 520                 525

Ser Ala Met Tyr Lys Cys Val Val Asn Lys Val Gly Gln Asp Glu
            530                 535                 540

Arg Leu Ile Tyr Phe Tyr Val Thr Thr Ile Pro Asp Gly Phe Ser Ile
545                 550                 555                 560

Glu Ser Glu Pro Ser Glu Asp Pro Leu Glu Gly Gln Ser Val Arg Leu
                565                 570                 575

Ser Cys Arg Ala Asp Asn Tyr Thr Tyr Glu His Leu Arg Trp Tyr Arg
            580                 585                 590

Leu Asn Leu Ser Thr Leu His Asp Ala Gln Gly Asn Pro Leu Leu Leu
            595                 600                 605

Asp Cys Lys Asn Val His Leu Phe Ala Thr Pro Leu Glu Ala Asn Leu
            610                 615                 620

Glu Glu Ala Glu Pro Gly Ala Arg His Ala Thr Leu Ser Leu Asn Ile
625                 630                 635                 640

Pro Arg Val Ala Pro Glu Asp Glu Gly Asp Tyr Val Cys Glu Val Gln
                645                 650                 655

Asp Arg Arg Ser Gln Asp Lys His Cys His Lys Lys Tyr Leu Ser Val
            660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Arg Cys Pro Val Ala Gly Ala
            690                 695                 700

His Val Pro Ser Ile Val Trp Tyr Lys Asp Glu Arg Leu Leu Glu Lys
705                 710                 715                 720

Glu Ser Gly Ile Asp Leu Ala Asp Ser Asn Gln Arg Leu Ser Ile Gln
                725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
            755                 760                 765

Glu Asp Lys Gly Ser Met Glu Ile Val Ile Leu Ile Gly Thr Gly Val
            770                 775                 780

Ile Ala Val Phe Phe Trp Val Leu Leu Leu Ile Phe Cys Asn Met
785                 790                 795                 800

Lys Arg Pro Ala His Ala Asp Ile Lys Thr Gly Tyr Leu Ser Ile Ile
                805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
            835                 840                 845

-continued

Arg Val Leu Gly His Gly Ala Phe Gly Lys Val Val Glu Ala Ser Ala
    850                 855                 860

Phe Gly Ile Asn Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
                900                 905                 910

Leu Gly Ala Cys Thr Lys Pro Asn Gly Pro Leu Met Val Ile Val Glu
                915                 920                 925

Phe Cys Lys Tyr Gly Asn Leu Ser Asn Phe Leu Arg Val Lys Arg Asp
    930                 935                 940

Thr Phe Asn Pro Tyr Ala Glu Lys Ser Pro Glu Gln Arg Arg Arg Phe
945                 950                 955                 960

Arg Ala Met Val Glu Gly Ala Lys Ala Asp Arg Arg Arg Pro Gly Ser
                965                 970                 975

Ser Asp Arg Ala Leu Phe Thr Arg Phe Leu Met Gly Lys Gly Ser Ala
                980                 985                 990

Arg Arg Ala Pro Leu Val Gln Glu Ala Glu Asp Leu Trp Leu Ser Pro
                995                 1000                1005

Leu Thr Met Glu Asp Leu Val Cys Tyr Ser Phe Gln Val Ala Arg
    1010                1015                1020

Gly Met Glu Phe Leu Ala Ser Arg Lys Cys Ile His Arg Asp Leu
    1025                1030                1035

Ala Ala Arg Asn Ile Leu Leu Ser Glu Ser Asp Ile Val Lys Ile
    1040                1045                1050

Cys Asp Phe Gly Leu Ala Arg Asp Ile Tyr Lys Asp Pro Asp Tyr
    1055                1060                1065

Val Arg Lys Gly Ser Ala Arg Leu Pro Leu Lys Trp Met Ala Pro
    1070                1075                1080

Glu Ser Ile Phe Asp Lys Val Tyr Thr Thr Gln Ser Asp Val Trp
    1085                1090                1095

Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Lys Asp Gly Thr Arg Met Arg Ala Pro Glu Leu Ala Thr Pro Ala
    1130                1135                1140

Ile Arg His Ile Met Gln Ser Cys Trp Ser Gly Asp Pro Lys Ala
    1145                1150                1155

Arg Pro Ala Phe Ser Asp Leu Val Glu Ile Leu Gly Asp Leu Leu
    1160                1165                1170

Gln Gly Gly Gly Trp Gln Glu Glu Glu Glu Arg Met Ala Leu
    1175                1180                1185

His Ser Ser Gln Ser Ser Glu Glu Asp Gly Phe Met Gln Ala Ser
    1190                1195                1200

Thr Thr Ala Leu His Ile Thr Glu Ala Asp Ala Asp Asp Ser Pro
    1205                1210                1215

Pro Ser Met His Cys His Ser Leu Ala Ala Arg Tyr Tyr Asn Cys
    1220                1225                1230

Val Ser Phe Pro Gly Arg Leu Ala Arg Gly Thr Lys Thr Pro Gly
    1235                1240                1245

-continued

| Ser | Ser | Arg | Met | Lys | Thr | Phe | Glu | Glu | Leu | Pro | Met | Thr | Pro | Thr |
| --- | --- | --- | --- | --- | --- | --- | --- | --- | --- | --- | --- | --- | --- | --- |
| | 1250 | | | | 1255 | | | | 1260 | | | | | |

| Thr | Tyr | Lys | Ala | Ser | Met | Asp | Asn | Gln | Thr | Asp | Ser | Gly | Met | Val |
| --- | --- | --- | --- | --- | --- | --- | --- | --- | --- | --- | --- | --- | --- | --- |
| 1265 | | | | | 1270 | | | | | 1275 | | | | |

| Leu | Ala | Ser | Glu | Glu | Phe | Glu | Glu | Leu | Glu | Ser | Arg | His | Arg | Pro |
| --- | --- | --- | --- | --- | --- | --- | --- | --- | --- | --- | --- | --- | --- | --- |
| 1280 | | | | | 1285 | | | | | 1290 | | | | |

| Glu | Gly | Ser | Phe | Ser | Cys | Lys | Gly | Pro | Gly | Gln | His | Met | Asp | Ile |
| --- | --- | --- | --- | --- | --- | --- | --- | --- | --- | --- | --- | --- | --- | --- |
| 1295 | | | | | 1300 | | | | | 1305 | | | | |

| Pro | Arg | Gly | His | Pro | Asp | Pro | Gln | Gly | Arg | Arg | Arg | Arg | Pro | Thr |
| --- | --- | --- | --- | --- | --- | --- | --- | --- | --- | --- | --- | --- | --- | --- |
| 1310 | | | | | 1315 | | | | | 1320 | | | | |

| Gln | Gly | Ala | Gln | Gly | Gly | Lys | Val | Phe | Tyr | Asn | Asn | Glu | Tyr | Gly |
| --- | --- | --- | --- | --- | --- | --- | --- | --- | --- | --- | --- | --- | --- | --- |
| 1325 | | | | | 1330 | | | | | 1335 | | | | |

| Glu | Val | Ser | Gln | Pro | Cys | Thr | Glu | Gly | Asp | Cys | Cys | Pro | Ser | Ala |
| --- | --- | --- | --- | --- | --- | --- | --- | --- | --- | --- | --- | --- | --- | --- |
| 1340 | | | | | 1345 | | | | | 1350 | | | | |

| Gly | Ser | Thr | Phe | Phe | Ala | Asp | Ser | Ser | Tyr |
| --- | --- | --- | --- | --- | --- | --- | --- | --- | --- |
| 1355 | | | | | 1360 | | | | |

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
cggcgccttc aggaaggtgg t                                           21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
cggaacattc cgctgtcgga a                                           21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
gtcggaaagc aacgtggtga a                                           21

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 23
catcaagacg ggctacct                                               18

<210> SEQ ID NO 24
<211> LENGTH: 18
<212> TYPE: DNA
<213> ORGANISM: Artificial Sequence

```
<220> FEATURE:
<223> OTHER INFORMATION: Description of Artificial Sequence: primer

<400> SEQUENCE: 24
ccgctgaccc cacacctt                                                   18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 25
gagttgacct cccaaggt                                                   18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 26
tctcctggac aggcagtc                                                   18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 27
gagttgacct cccaaggt                                                   18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 28
tctcctggac aggcagtc                                                   18

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (5)..(7)
<223> OTHER INFORMATION: Xaa can be any amino acid
<220> FEATURE:
<221> NAME/KEY: misc_feature
<222> LOCATION: (10)..(10)
<223> OTHER INFORMATION: Xaa can be any amino acid

<400> SEQUENCE: 29

Pro Xaa Cys Val Xaa Xaa Xaa Arg Cys Xaa Gly Cys Cys
1               5                   10
```

<210> SEQ ID NO 30
<211> LENGTH: 191
<212> TYPE: PRT
<213> ORGANISM: Homo sapiens

<400> SEQUENCE: 30

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```

<210> SEQ ID NO 31
<211> LENGTH: 207
<212> TYPE: PRT
<213> ORGANISM: Homo sapiens

<400> SEQUENCE: 31

```
Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Arg Ala Ala Thr Pro His His Arg
    130                 135                 140
```

```
Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
                180                 185                 190

Ala Ala Ala Asp Ala Ala Ala Ser Ser Val Ala Lys Gly Gly Ala
            195                 200                 205

<210> SEQ ID NO 32
<211> LENGTH: 149
<212> TYPE: PRT
<213> ORGANISM: Homo sapiens

<400> SEQUENCE: 32

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
                20                  25                  30

Asn Gly Ser Ser Glu Val Glu Val Val Pro Phe Gln Glu Val Trp Gly
            35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
                100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Cys Gly Asp
    130                 135                 140

Ala Val Pro Arg Arg
145
```